(12) United States Patent
Ohtaki et al.

(10) Patent No.: US 7,045,299 B2
(45) Date of Patent: May 16, 2006

(54) PHYSIOLOGICALLY ACTIVE PEPTIDE AND USE THEREOF

(75) Inventors: Tetsuya Ohtaki, Tsukuba (JP); Yasushi Masuda, Tsukuba (JP); Yoshihiro Takatsu, Tsukuba (JP); Takuya Watanabe, Osaka (JP); Yasuko Terao, Kobe (JP); Yasushi Shintani, Toyonaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 31 days.

(21) Appl. No.: 10/333,192

(22) PCT Filed: Jul. 17, 2001

(86) PCT No.: PCT/JP01/06162

§ 371 (c)(1),
(2), (4) Date: Sep. 29, 2003

(87) PCT Pub. No.: WO02/06483

PCT Pub. Date: Jan. 24, 2002

(65) Prior Publication Data

US 2004/0077535 A1    Apr. 22, 2004

(30) Foreign Application Priority Data

Jul. 18, 2000  (JP) .............................. 2000-217442
Feb. 2, 2001   (JP) .............................. 2001-026779

(51) Int. Cl.
*G01N 33/53*   (2006.01)
*C12P 2/06*    (2006.01)
*C07K 14/00*   (2006.01)
*C07K 2/00*    (2006.01)

(52) U.S. Cl. .................. 435/7.1; 435/7.93; 435/69.1; 530/350; 530/300

(58) Field of Classification Search ............... 530/350, 530/300, 326; 435/69.1, 7.93, 6, 7.95, 7.1
See application file for complete search history.

(56) References Cited

FOREIGN PATENT DOCUMENTS

| WO | WO 98/46620      | 10/1998 |
|----|------------------|---------|
| WO | WO 99/06550      | 2/1999  |
| WO | WO 9906550 A2 *  | 2/1999  |
| WO | WO 99/63088      | 12/1999 |
| WO | WO 00/34334      | 6/2000  |
| WO | WO 00/52022      | 9/2000  |
| WO | WO 00/53753      | 9/2000  |
| WO | WO 00/70049      | 11/2000 |
| WO | WO 00/73454      | 12/2000 |
| WO | WO 00/75327      | 12/2000 |
| WO | WO 01/16309      | 3/2001  |
| WO | WO 01/36465      | 5/2001  |

OTHER PUBLICATIONS

Bowie et al., Science 247: 1306-1310, 1990.*
Wells, Biochemistry 29:8509-8517, 1990.*
Wechselberger et al. "The mammalian homologues of frog Bv8 are mainly expressed in spermatocytes" FEBS Letters 462 (1999): 177-181.
Parker et al. "Y-receptor-like genes GPR72 and GPR73: molecular cloning, genomic organization and assignment to human chromosome 11q21.1 and 2p14 and mouse chromosome 9 and 6" Biochem et Biophys Acta 1491 (2000): 369-375.
Schweitz et al. "MIT1, a black mamba toxin with a new and highly potent activity on intestinal contraction" FEBS Letters 461 (1999): 183-188.
Tatemoto et al. "Isolation and characterization of a novel endogenous peptide ligand for the human APJ receptor" Biochemical and Biophysical research communications 251: 471-476 (1998).
Osinski et al. "Cloning, expression and functional role of a nociceptin/orphanin FQ receptor in the porcine gastrointestinal tract" Eur. J. Pharmacology 365 (1999): 281-289.
Fujii et al. "Identification of Neuromedin U as the Cognate Ligand of the Orphan G Protein-coupled receptor FM-3" Jour. Biol. Chem. 275(28): 21068-21074 (2000).

* cited by examiner

*Primary Examiner*—Janet L. Andres
*Assistant Examiner*—Gyan Chandra
(74) *Attorney, Agent, or Firm*—Elaine M. Ramesh; Mark Chao

(57) ABSTRACT

The present invention intends to provide a novel peptide and use thereof. More particularly, the present invention provides a novel peptide and a DNA encoding the same, a drug comprising the peptide or DNA, a screening method/screening kit for a compound or its salt that promotes or inhibits the activity of the peptide, a compound or its salt obtained by the screening, a drug comprising the compound or its salt, etc.

The peptide of the invention and the DNA encoding the same are usable, e.g., for the diagnosis, treatment, prevention, etc. of digestive diseases, etc. Moreover, the peptide of the invention is useful as a reagent for screening a compound or its salt that promotes or inhibits the activity of the protein of the invention.

2 Claims, 16 Drawing Sheets

Fig.1

```
         10         20         30         40         50         60
ATGGAGACCACCATGGGGTTCATGGATGACAATGCCACCAACACTTCCACCAGCTTCCTT
 M  E  T  T  M  G  F  M  D  D  N  A  T  N  T  S  T  S  F  L 70         80         90        100        110        120
TCTGTGCTCAACCCTCATGGAGCCCATGCCACTTCCTTCCCATTCAACTTCAGCTACAGC
 S  V  L  N  P  H  G  A  H  A  T  S  F  P  F  N  F  S  Y  S 130        140        150        160        170        180
GACTATGATATGCCTTTGGATGAAGATGAGGATGTGACCAATTCCAGGACGTTCTTTGCT
 D  Y  D  M  P  L  D  E  D  E  D  V  T  N  S  R  T  F  F  A 190        200        210        220        230        240
GCCAAGATTGTCATTGGGATGGCCCTGGTGGGCATCATGCTGGTCTGCGGCATTGGAAAC
 A  K  I  V  I  G  M  A  L  V  G  I  M  L  V  C  G  I  G  N 250        260        270        280        290        300
TTCATCTTTATCGCTGCCCTGGTCCGCTACAAGAAACTGCGCAACCTCACCAACCTGCTC
 F  I  F  I  A  A  L  V  R  Y  K  K  L  R  N  L  T  N  L  L 310        320        330        340        350        360
ATCGCCAACCTGGCCATCTCTGACTTCCTGGTGGCCATTGTCTGCTGCCCCTTTGAGATG
 I  A  N  L  A  I  S  D  F  L  V  A  I  V  C  C  P  F  E  M 370        380        390        400        410        420
GACTACTATGTGGTGCGCCAGCTCTCCTGGGAGCACGGCCACGTCCTGTGCACCTCTGTC
 D  Y  Y  V  V  R  Q  L  S  W  E  H  G  H  V  L  C  T  S  V
```

Fig.2

```
            430       440       450       460       470       480
       AACTACCTGCGCACTGTCTCTCTCTATGTCTCCACCAATGCCCTGCTGGCCATCGCCATT
        N  Y  L  R  T  V  S  L  Y  V  S  T  N  A  L  L  A  I  A  I 490       500       510       520       530       540
       GACAGGTATCTGGCTATTGTCCATCCGCTGAGACCACGGATGAAGTGCCAAACAGCCACT
        D  R  Y  L  A  I  V  H  P  L  R  P  R  M  K  C  Q  T  A  T 550       560       570       580       590       600
       GGCCTGATTGCCTTGGTGTGGACGGTGTCCATCCTGATCGCCATCCCTTCCGCCTACTTC
        G  L  I  A  L  V  W  T  V  S  I  L  I  A  I  P  S  A  Y  F 610       620       630       640       650       660
       ACCACCGAGACGGTCCTCGTCATTGTCAAGAGCCAGGAAAAGATCTTCTGCGGCCAGATC
        T  T  E  T  V  L  V  I  V  K  S  Q  E  K  I  F  C  G  Q  I 670       680       690       700       710       720
       TGGCCTGTGGACCAGCAGCTCTACTACAAGTCCTACTTCCTCTTTATCTTTGGCATAGAA
        W  P  V  D  Q  Q  L  Y  Y  K  S  Y  F  L  F  I  F  G  I  E 730       740       750       760       770       780
       TTCGTGGGCCCCGTGGTCACCATGACCCTGTGCTATGCCAGGATCTCCCGGGAGCTCTGG
        F  V  G  P  V  V  T  M  T  L  C  Y  A  R  I  S  R  E  L  W 790       800       810       820       830       840
       TTCAAGGCGGTCCCTGGATTCCAGACAGAGCAGATCCGCAAGAGGCTGCGCTGCCGCAGG
        F  K  A  V  P  G  F  Q  T  E  Q  I  R  K  R  L  R  C  R  R 850       860       870       880       890       900
       AAGACGGTCCTGGTGCTCATGTGCATCCTCACCGCCTACGTGCTATGCTGGGCGCCCTTC
        K  T  V  L  V  L  M  C  I  L  T  A  Y  V  L  C  W  A  P  F
```

Fig. 3

```
          910       920       930       940       950       960
TACGGCTTCACCATCGTGCGCGACTTCTTCCCCACCGTGTTCGTGAAGGAGAAGCACTAC
 Y  G  F  T  I  V  R  D  F  F  P  T  V  F  V  K  E  K  H  Y 970       980       990      1000      1010      1020
CTCACTGCCTTCTACATCGTCGAGTGCATCGCCATGAGCAACAGCATGATCAACACTCTG
 L  T  A  F  Y  I  V  E  C  I  A  M  S  N  S  M  I  N  T  L 1030      1040      1050      1060      1070      1080
TGCTTCGTGACCGTCAAGAACGACACCGTCAAGTACTTCAAAAAGATCATGTTGCTCCAC
 C  F  V  T  V  K  N  D  T  V  K  Y  F  K  K  I  M  L  L  H 1090      1100      1110      1120      1130      1140
TGGAAGGCTTCTTACAATGGCGGTAAGTCCAGTGCAGACCTGGACCTCAAGACAATTGGG
 W  K  A  S  Y  N  G  G  K  S  S  A  D  L  D  L  K  T  I  G 1150      1160      1170      1180      1190
ATGCCTGCCACCGAAGAGGTGGACTGCATCAGACTAAAATAA
 M  P  A  T  E  E  V  D  C  I  R  L  K  *
```

Fig. 4

```
          10        20        30        40        50        60
ATGGAGACCACCATGGGGTTCATGGATGACAATGCCACCAACACTTCCACCAGCTTCCTT
 M  E  T  T  M  G  F  M  D  D  N  A  T  N  T  S  T  S  F  L 70        80        90       100       110       120
TCTGTGCTCAACCCTCATGGAGCCCATGCCACTTCCTTCCCATTCAACTTCAGCTACAGC
 S  V  L  N  P  H  G  A  H  A  T  S  F  P  F  N  F  S  Y  S 130       140       150       160       170       180
GACTATGATATGCCTTTGGATGAAGATGAGGATGTGACCAATTCCAGGACGTTCTTTGCT
 D  Y  D  M  P  L  D  E  D  E  D  V  T  N  S  R  T  F  F  A 190       200       210       220       230       240
GCCAAGATTGTCATTGGGATGGCCCTGGTGGGCATCATGCTGGTCTGCGGCATTGGAAAC
 A  K  I  V  I  G  M  A  L  V  G  I  M  L  V  C  G  I  G  N 250       260       270       280       290       300
TTCATCTTTATCGCTGCCCTGGTCCGCTACAAGAAACTGCGCAACCTCACCAACCTGCTC
 F  I  F  I  A  A  L  V  R  Y  K  K  L  R  N  L  T  N  L  L 310       320       330       340       350       360
ATCGCCAACCTGGCCATCTCTGACTTCCTGGTGGCCATTGTCTGCTGCCCCTTTGAGATG
 I  A  N  L  A  I  S  D  F  L  V  A  I  V  C  C  P  F  E  M 370       380       390       400       410       420
GACTACTATGTGGTGCGCCAGCTCTCCTGGGAGCACGGCCACGTCCTGTGCACCTCTGTC
 D  Y  Y  V  V  R  Q  L  S  W  E  H  G  H  V  L  C  T  S  V
```

Fig.5

```
          430       440       450       460       470       480
AACTACCTGCGCACTGTCTCTCTCTATGTCTCCACCAATGCCCTGCTGGCCATCGCCATT
 N  Y  L  R  T  V  S  L  Y  V  S  T  N  A  L  L  A  I  A  I 490       500       510       520       530       540
GACAGGTATCTGGCTATTGTCCATCCGCTGAGACCACGGATGAAGTGCCAAACAGCCACT
 D  R  Y  L  A  I  V  H  P  L  R  P  R  M  K  C  Q  T  A  T 550       560       570       580       590       600
GGCCTGATTGCCTTGGTGTGGACGGTGTCCATCCTGATCGCCATCCCTTCCGCCTACTTC
 G  L  I  A  L  V  W  T  V  S  I  L  I  A  I  P  S  A  Y  F 610       620       630       640       650       660
ACCACCGAGACGGTCCTCGTCATTGTCAAGAGCCAGGAAAAGATCTTCTGCGGCCAGATC
 T  T  E  T  V  L  V  I  V  K  S  Q  E  K  I  F  C  G  Q  I 670       680       690       700       710       720
TGGCCTGTGGACCAGCAGCTCTACTACAAGTCCTACTTCCTCTTTATCTTTGGCATAGAA
 W  P  V  D  Q  Q  L  Y  Y  K  S  Y  F  L  F  I  F  G  I  E 730       740       750       760       770       780
TTCGTGGGCCCCGTGGTCACCATGACCCTGTGCTATGCCAGGATCTCCCGGGAGCTCTGG
 F  V  G  P  V  V  T  M  T  L  C  Y  A  R  I  S  R  E  L  W 790       800       810       820       830       840
TTCAAGGCGGTCCCTGGATTCCAGACAGAGCAGATCCGCAAGAGGCTGCGCTGCCGCAGG
 F  K  A  V  P  G  F  Q  T  E  Q  I  R  K  R  L  R  C  R  R 850       860       870       880       890       900
AAGACGGTCCTGGTGCTCATGTGCATCCTCACCGCCTACGTGCTATGCTGGGCGCCCTTC
 K  T  V  L  V  L  M  C  I  L  T  A  Y  V  L  C  W  A  P  F
```

Fig.6

```
       910       920       930       940       950       960
TACGGCTTCACCATCGTGCGCGACTTCTTCCCCACCGTGTTTGTGAAGGAGAAGCACTAC
 Y  G  F  T  I  V  R  D  F  F  P  T  V  F  V  K  E  K  H  Y 970       980       990      1000      1010      1020
CTCACTGCCTTCTACATCGTCGAGTGCATCGCCATGAGCAACAGCATGATCAACACTCTG
 L  T  A  F  Y  I  V  E  C  I  A  M  S  N  S  M  I  N  T  L 1030      1040      1050      1060      1070      1080
TGCTTCGTGACCGTCAAGAACGACACCGTCAAGTACTTCAAAAAGATCATGTTGCTCCAC
 C  F  V  T  V  K  N  D  T  V  K  Y  F  K  K  I  M  L  L  H 1090      1100      1110      1120      1130      1140
TGGAAGGCTTCTTACAATGGCGGTAAGTCCAGTGCAGACCTGGACCTCAAGACAATTGGG
 W  K  A  S  Y  N  G  G  K  S  S  A  D  L  D  L  K  T  I  G 1150      1160      1170      1180      1190
ATGCCTGCCACCGAAGAGGTGGACTGCATCAGACTAAAATAA
 M  P  A  T  E  E  V  D  C  I  R  L  K  *
```

Fig.9

| | |
|---|---|
| MIT1 | AVITGACERD LQCGKGTCCA VSLWIKSVRV CTPVGTSGED CHPASHKIPF |
| Human (A type) | AVITGACERD VQCGAGTCCA ISLWLRGLRM CTPLGREGEE CHPGSHKIPF |
| Human (G type) | AVITGACERD VQCGAGTCCA ISLWLRGLRM CTPLGREGEE CHPGSHKVPF |

| | |
|---|---|
| MIT1 | SGQRMHHTCP CAPNLACVQT SPKKFKCLSK |
| Human (A type) | FRKRKHHTCP CLPNLLCSRF PDGRYRCSMD LKNINF |
| Human (G type) | FRKRKHHTCP CLPNLLCSRF PDGRYRCSMD LKNINF |

SEQUENCE LISTING

<160> NUMBER OF SEQ ID NOS: 58

<210> SEQ ID NO 1
<211> LENGTH: 393
<212> TYPE: PRT
<213> ORGANISM: Human

<400> SEQUENCE: 1

Met Glu Thr Thr Met Gly Phe Met Asp Asp Asn Ala Thr Asn Thr Ser
 1               5                  10                  15

Thr Ser Phe Leu Ser Val Leu Asn Pro His Gly Ala His Ala Thr Ser
            20                  25                  30

Phe Pro Phe Asn Phe Ser Tyr Ser Asp Tyr Asp Met Pro Leu Asp Glu
        35                  40                  45

Asp Glu Asp Val Thr Asn Ser Arg Thr Phe Phe Ala Ala Lys Ile Val
    50                  55                  60

Ile Gly Met Ala Leu Val Gly Ile Met Leu Val Cys Gly Ile Gly Asn
65                  70                  75                  80

Phe Ile Phe Ile Ala Ala Leu Val Arg Tyr Lys Lys Leu Arg Asn Leu
                85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
        115                 120                 125

Ser Trp Glu His Gly His Val Leu Cys Thr Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Thr Gly Leu Ile Ala Leu Val Trp Thr Val Ser Ile Leu
            180                 185                 190

Ile Ala Ile Pro Ser Ala Tyr Phe Thr Thr Glu Thr Val Leu Val Ile
        195                 200                 205

Val Lys Ser Gln Glu Lys Ile Phe Cys Gly Gln Ile Trp Pro Val Asp
    210                 215                 220

Gln Gln Leu Tyr Tyr Lys Ser Tyr Phe Leu Phe Ile Phe Gly Ile Glu
225                 230                 235                 240

Phe Val Gly Pro Val Val Thr Met Thr Leu Cys Tyr Ala Arg Ile Ser
                245                 250                 255

Arg Glu Leu Trp Phe Lys Ala Val Pro Gly Phe Gln Thr Glu Gln Ile
            260                 265                 270

Arg Lys Arg Leu Arg Cys Arg Arg Lys Thr Val Leu Val Leu Met Cys
    275                 280                 285

Ile Leu Thr Ala Tyr Val Leu Cys Trp Ala Pro Phe Tyr Gly Phe Thr
290                 295                 300

Ile Val Arg Asp Phe Phe Pro Thr Val Phe Val Lys Glu Lys His Tyr
305                 310                 315                 320

Leu Thr Ala Phe Tyr Ile Val Glu Cys Ile Ala Met Ser Asn Ser Met
                325                 330                 335

Ile Asn Thr Leu Cys Phe Val Thr Val Lys Asn Asp Thr Val Lys Tyr
            340                 345                 350

Phe Lys Lys Ile Met Leu Leu His Trp Lys Ala Ser Tyr Asn Gly Gly

|   |   |   | 355 |   |   |   |   | 360 |   |   |   |   | 365 |   |   |
|---|---|---|---|---|---|---|---|---|---|---|---|---|---|---|---|

Lys Ser Ser Ala Asp Leu Asp Leu Lys Thr Ile Gly Met Pro Ala Thr
    370               375               380

Glu Glu Val Asp Cys Ile Arg Leu Lys
385               390

<210> SEQ ID NO 2
<211> LENGTH: 1179
<212> TYPE: DNA
<213> ORGANISM: Human

<400> SEQUENCE: 2

| | | | | | |
|---|---|---|---|---|---|
| atggagacca | ccatggggtt | catggatgac | aatgccacca | acacttccac | cagcttcctt | 60 |
| tctgtgctca | accctcatgg | agcccatgcc | acttccttcc | cattcaactt | cagctacagc | 120 |
| gactatgata | tgcctttgga | tgaagatgag | gatgtgacca | attccaggac | gttctttgct | 180 |
| gccaagattg | tcattgggat | ggccctggtg | gcatcatgc | tggtctgcgg | cattggaaac | 240 |
| ttcatcttta | tcgctgccct | ggtccgctac | aagaaactgc | gcaacctcac | caacctgctc | 300 |
| atcgccaacc | tggccatctc | tgacttcctg | gtggccattg | tctgctgccc | ctttgagatg | 360 |
| gactactatg | tggtgcgcca | gctctcctgg | gagcacggcc | acgtcctgtg | cacctctgtc | 420 |
| aactacctgc | gcactgtctc | tctctatgtc | tccaccaatg | ccctgctggc | catcgccatt | 480 |
| gacaggtatc | tggctattgt | ccatccgctg | agaccacgga | tgaagtgcca | aacagccact | 540 |
| ggcctgattg | ccttggtgtg | gacggtgtcc | atcctgatcg | ccatcccttc | cgcctacttc | 600 |
| accaccgaga | cggtcctcgt | cattgtcaag | agccaggaaa | agatcttctg | cggccagatc | 660 |
| tggcctgtgg | accagcagct | ctactacaag | tcctacttcc | tctttatctt | tggcatagaa | 720 |
| ttcgtgggcc | ccgtggtcac | catgacccctg | tgctatgcca | ggatctcccg | ggagctctgg | 780 |
| ttcaaggcgg | tccctggatt | ccagacagag | cagatccgca | agaggctgcg | ctgccgcagg | 840 |
| aagacggtcc | tggtgctcat | gtgcatcctc | accgcctacg | tgctatgctg | ggcgcccttc | 900 |
| tacggcttca | ccatcgtgcg | cgacttcttc | cccaccgtgt | tcgtgaagga | gaagcactac | 960 |
| ctcactgcct | tctacatcgt | cgagtgcatc | gccatgagca | acagcatgat | caacactctg | 1020 |
| tgcttcgtga | ccgtcaagaa | cgacaccgtc | aagtacttca | aaaagatcat | gttgctccac | 1080 |
| tggaaggctt | cttacaatgg | cggtaagtcc | agtgcagacc | tggacctcaa | gacaattggg | 1140 |
| atgcctgcca | ccgaagaggt | ggactgcatc | agactaaaa | | | 1179 |

<210> SEQ ID NO 3
<211> LENGTH: 1179
<212> TYPE: DNA
<213> ORGANISM: Human

<400> SEQUENCE: 3

| | | | | | |
|---|---|---|---|---|---|
| atggagacca | ccatggggtt | catggatgac | aatgccacca | acacttccac | cagcttcctt | 60 |
| tctgtgctca | accctcatgg | agcccatgcc | acttccttcc | cattcaactt | cagctacagc | 120 |
| gactatgata | tgcctttgga | tgaagatgag | gatgtgacca | attccaggac | gttctttgct | 180 |
| gccaagattg | tcattgggat | ggccctggtg | gcatcatgc | tggtctgcgg | cattggaaac | 240 |
| ttcatcttta | tcgctgccct | ggtccgctac | aagaaactgc | gcaacctcac | caacctgctc | 300 |
| atcgccaacc | tggccatctc | tgacttcctg | gtggccattg | tctgctgccc | ctttgagatg | 360 |
| gactactatg | tggtgcgcca | gctctcctgg | gagcacggcc | acgtcctgtg | cacctctgtc | 420 |
| aactacctgc | gcactgtctc | tctctatgtc | tccaccaatg | ccctgctggc | catcgccatt | 480 |

```
gacaggtatc tggctattgt ccatccgctg agaccacgga tgaagtgcca aacagccact    540
ggcctgattg ccttggtgtg gacggtgtcc atcctgatcg ccatcccttc cgcctacttc    600
accaccgaga cggtcctcgt cattgtcaag agccaggaaa agatcttctg cggccagatc    660
tggcctgtgg accagcagct ctactacaag tcctacttcc tctttatctt tggcatagaa    720
ttcgtgggcc ccgtggtcac catgaccctg tgctatgcca ggatctcccg ggagctctgg    780
ttcaaggcgg tccctggatt ccagacagag cagatccgca gaggctgcg ctgccgcagg     840 aagacggtcc tggtgctcat gtgcatcctc accgcctacg tgctatgctg ggcgcccttc    900
tacggcttca ccatcgtgcg cgacttcttc cccaccgtgt ttgtgaagga gaagcactac    960
ctcactgcct tctacatcgt cgagtgcatc gccatgagca acagcatgat caacactctg    1020
tgcttcgtga ccgtcaagaa cgacaccgtc aagtacttca aaaagatcat gttgctccac    1080
tggaaggctt cttacaatgg cggtaagtcc agtgcagacc tggacctcaa gacaattggg    1140
atgcctgcca ccgaagaggt ggactgcatc agactaaaa                           1179

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
gtcgacatgg agaccaccat ggggttcatg g                                   31

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
actagtttat tttagtctga tgcagtccac ctcttc                              36

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tcatgttgct ccactggaag g                                              21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ccaattgtct tgaggtccag g                                              21

<210> SEQ ID NO 8
<211> LENGTH: 29
<212> TYPE: DNA
<213> ORGANISM: Artificial Sequence
<220> FEATURE:
```

```
<223> OTHER INFORMATION: probe

<400> SEQUENCE: 8
ttcttacaat ggcggtaagt ccagtgcag                                              29

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
gtcgacatgg agaccaccat ggggttcatg g                                           31

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
actagtttat tttagtctga tgcagtccac ctcttc                                      36

<210> SEQ ID NO 11
<211> LENGTH: 16
<212> TYPE: PRT
<213> ORGANISM: Bovine
<220> FEATURE:
<221> NAME/KEY: UNSURE
<222> LOCATION: (7)
<223> OTHER INFORMATION: Xaa is an unidentified residue.
<220> FEATURE:
<221> NAME/KEY: UNSURE
<222> LOCATION: (13)
<223> OTHER INFORMATION: Xaa is an unidentified residue.

<400> SEQUENCE: 11

Ala Val Ile Thr Gly Ala Xaa Glu Arg Asp Val Gln Xaa Arg Ala Gly
                5                  10                  15

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
ggtgccacgc gagtctcaat catgctcc                                               28

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
ggggcctgtg agcgggatgt ccagtgtg                                               28

<210> SEQ ID NO 14
<211> LENGTH: 28
<212> TYPE: DNA
<213> ORGANISM: Artificial Sequence
<220> FEATURE:
```

<223> OTHER INFORMATION: primer

<400> SEQUENCE: 14
cttcttcagg aaacgcaagc accacacc                                          28

<210> SEQ ID NO 15
<211> LENGTH: 409
<212> TYPE: DNA
<213> ORGANISM: Human

<400> SEQUENCE: 15
cttcttcagg aaacgcaagc accacacctg tccttgcttg cccaacctgc tgtgctccag        60
gttcccggac ggcaggtacc gctgctccat ggacttgaag aacatcaatt tttaggcgct      120
tgcctggtct caggataccc accatccttt tcctgagcac agcctggatt tttatttctg      180
ccatgaaacc cagctcccat gactctccca gtccctacac tgactaccct gatctctctt      240
gtctagtacg cacatatgca cacaggcaga catacctccc atcatgacat ggtccccagg      300
ctggcctgag gatgtcacag cttgaggctg tggtgtgaaa ggtggccagc ctggttctct      360
tccctgctca ggctgccaga gaggtggtaa atggcagaaa ggacattcc                 409

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ccaccatgag aggtgccacg                                                   20

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
ctcgagctca ggaaaaggat ggtg                                              24

<210> SEQ ID NO 18
<211> LENGTH: 371
<212> TYPE: DNA
<213> ORGANISM: Human

<400> SEQUENCE: 18
ccaccatgag aggtgccacg cgagtctcaa tcatgctcct cctagtaact gtgtctgact        60
gtgctgtgat cacaggggcc tgtgagcggg atgtccagtg tggggcaggc acctgctgtg      120
ccatcagcct gtggcttcga gggctgcgga tgtgcacccc gctggggcgg aaggcgagg       180 agtgccaccc cggcagccac aagatcccct tcttcaggaa acgcaagcac cacacctgtc      240
cttgcttgcc caacctgctg tgctccaggt tcccggacgg caggtaccgc tgctccatgg      300
acttgaagaa catcaatttt taggcgcttg cctggtctca ggatacccac catccttttc      360
ctgagctcga g                                                          371

<210> SEQ ID NO 19
<211> LENGTH: 371
<212> TYPE: DNA
<213> ORGANISM: Human

<400> SEQUENCE: 19

```
ccaccatgag aggtgccacg cgagtctcaa tcatgctcct cctagtaact gtgtctgact      60
gtgctgtgat cacaggggcc tgtgagcggg atgtccagtg tggggcaggc acctgctgtg     120
ccatcagcct gtggcttcga gggctgcgga tgtgcacccc gctggggcgg aaggcgagg      180
agtgccaccc cggcagccac aaggtccccct tcttcaggaa acgcaagcac acacctgtc     240
cttgcttgcc caacctgctg tgctccaggt tcccggacgg caggtaccgc tgctccatgg     300
acttgaagaa catcaatttt taggcgcttg cctggtctca ggatacccac catccttttc     360
ctgagctcga g                                                          371
```

<210> SEQ ID NO 20
<211> LENGTH: 86
<212> TYPE: PRT
<213> ORGANISM: Human

<400> SEQUENCE: 20

```
Ala Val Ile Thr Gly Ala Cys Glu Arg Asp Val Gln Cys Gly Ala Gly
                5                  10                  15
Thr Cys Cys Ala Ile Ser Leu Trp Leu Arg Gly Leu Arg Met Cys Thr
            20                  25                  30
Pro Leu Gly Arg Glu Gly Glu Cys His Pro Gly Ser His Lys Ile
        35                  40                  45
Pro Phe Phe Arg Lys Arg Lys His Thr Cys Pro Cys Leu Pro Asn
    50                  55                  60
Leu Leu Cys Ser Arg Phe Pro Asp Gly Arg Tyr Arg Cys Ser Met Asp
65                  70                  75                  80
Leu Lys Asn Ile Asn Phe
                85
```

<210> SEQ ID NO 21
<211> LENGTH: 86
<212> TYPE: PRT
<213> ORGANISM: Human

<400> SEQUENCE: 21

```
Ala Val Ile Thr Gly Ala Cys Glu Arg Asp Val Gln Cys Gly Ala Gly
                5                  10                  15
Thr Cys Cys Ala Ile Ser Leu Trp Leu Arg Gly Leu Arg Met Cys Thr
            20                  25                  30
Pro Leu Gly Arg Glu Gly Glu Cys His Pro Gly Ser His Lys Val
        35                  40                  45
Pro Phe Phe Arg Lys Arg Lys His Thr Cys Pro Cys Leu Pro Asn
    50                  55                  60
Leu Leu Cys Ser Arg Phe Pro Asp Gly Arg Tyr Arg Cys Ser Met Asp
65                  70                  75                  80
Leu Lys Asn Ile Asn Phe
                85
```

<210> SEQ ID NO 22
<211> LENGTH: 105
<212> TYPE: PRT
<213> ORGANISM: Human

<400> SEQUENCE: 22

```
Met Arg Gly Ala Thr Arg Val Ser Ile Met Leu Leu Leu Val Thr Val
                5                  10                  15
```

```
Ser Asp Cys Ala Val Ile Thr Gly Ala cys Glu Arg Asp Val Gln Cys
        20                  25                  30

Gly Ala Gly Thr Cys Cys Ala Ile Ser Leu Trp Leu Arg Gly Leu Arg
            35                  40                  45

Met Cys Thr Pro Leu Gly Arg Glu Gly Glu Glu Cys His Pro Gly Ser
 50                      55                  60

His Lys Ile Pro Phe Phe Arg Lys Arg Lys His His Thr Cys Pro Cys
 65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105

<210> SEQ ID NO 23
<211> LENGTH: 105
<212> TYPE: PRT
<213> ORGANISM: Human

<400> SEQUENCE: 23

Met Arg Gly Ala Thr Arg Val Ser Ile Met Leu Leu Leu Val Thr Val
                 5                  10                  15

Ser Asp Cys Ala Val Ile Thr Gly Ala cys Glu Arg Asp Val Gln Cys
            20                  25                  30

Gly Ala Gly Thr Cys Cys Ala Ile Ser Leu Trp Leu Arg Gly Leu Arg
        35                  40                  45

Met Cys Thr Pro Leu Gly Arg Glu Gly Glu Glu Cys His Pro Gly Ser
 50                      55                  60

His Lys Val Pro Phe Phe Arg Lys Arg Lys His His Thr Cys Pro Cys
 65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105

<210> SEQ ID NO 24
<211> LENGTH: 678
<212> TYPE: DNA
<213> ORGANISM: Human

<400> SEQUENCE: 24
aaggctgagc gggaggaagc gagaggcatc taagcaggca gtgttttgcc ttcacccaa       60 gtgaccatga gaggtgccac gcgagtctca atcatgctcc tcctagtaac tgtgtctgac    120
tgtgctgtga tcacagggc  ctgtgagcgg gatgtccagt gtggggcagg cacctgctgt    180
gccatcagcc tgtggcttcg agggctgcgg atgtgcaccc cgctggggcg ggaaggcgag    240
gagtgccacc ccggcagcca caagatcccc ttcttcagga acgcaagca ccacacctgt    300 ccttgcttgc ccaacctgct gtgctccagg ttcccggacg gcaggtaccg ctgctccatg    360
gacttgaaga acatcaattt ttaggcgctt gcctggtctc aggatacca ccatccttt    420 cctgagcaca gcctggattt ttatttctgc catgaaaccc agctcccatg actctcccag    480
tccctacact gactaccctg atctctcttg tctagtacgc acatatgcac acaggcagac    540
atacctccca tcatgacatg gtccccaggc tggcctgagg atgtcacagc ttgaggctgt    600
ggtgtgaaag gtggccagcc tggttctctt ccctgctcag gctgccagag aggtggtaaa    660
tggcagaaag gacattcc                                                   678
```

<210> SEQ ID NO 25
<211> LENGTH: 678
<212> TYPE: DNA
<213> ORGANISM: Human

<400> SEQUENCE: 25

```
aaggctgagc gggaggaagc gagaggcatc taagcaggca gtgttttgcc ttcacccaa      60
gtgaccatga gaggtgccac gcgagtctca atcatgctcc tcctagtaac tgtgtctgac    120
tgtgctgtga tcacagggc ctgtgagcgg gatgtccagt gtgggcagg cacctgctgt      180
gccatcagcc tgtggcttcg agggctgcgg atgtgcaccc cgctggggcg ggaaggcgag    240
gagtgccacc ccggcagcca caaggtcccc ttcttcagga acgcaagca ccacacctgt    300
ccttgcttgc caacctgct gtgctccagg ttcccggacg gcaggtaccg ctgctccatg    360
gacttgaaga acatcaattt ttaggcgctt gcctggtctc aggatacca ccatccttt     420
cctgagcaca gcctggattt ttatttctgc catgaaaccc agctcccatg actctcccag    480
tccctacact gactaccctg atctctcttg tctagtacgc acatatgcac acaggcagac    540
atacctccca tcatgacatg gtcccaggc tggcctgagg atgtcacagc ttgaggctgt     600
ggtgtgaaag gtggccagcc tggttctctt ccctgctcag gctgccagag aggtggtaaa    660
tggcagaaag gacattcc                                                  678
```

<210> SEQ ID NO 26
<211> LENGTH: 258
<212> TYPE: DNA
<213> ORGANISM: Human

<400> SEQUENCE: 26

```
gctgtgatca caggggcctg tgagcgggat gtccagtgtg gggcaggcac ctgctgtgcc     60
atcagcctgt ggcttcgagg gctgcggatg tgcaccccgc tggggcggga aggcgaggag    120
tgccaccccg cagccacaa gatcccttc ttcaggaaac gcaagcacca cacctgtcct     180
tgcttgccca acctgctgtg ctccaggttc ccggacggca ggtaccgctg ctccatggac    240
ttgaagaaca tcaattt                                                  258
```

<210> SEQ ID NO 27
<211> LENGTH: 258
<212> TYPE: DNA
<213> ORGANISM: Human

<400> SEQUENCE: 27

```
gctgtgatca caggggcctg tgagcgggat gtccagtgtg gggcaggcac ctgctgtgcc     60
atcagcctgt ggcttcgagg gctgcggatg tgcaccccgc tggggcggga aggcgaggag    120
tgccaccccg cagccacaa ggtcccttc ttcaggaaac gcaagcacca cacctgtcct    180
tgcttgccca acctgctgtg ctccaggttc ccggacggca ggtaccgctg ctccatggac    240
ttgaagaaca tcaattt                                                  258
```

<210> SEQ ID NO 28
<211> LENGTH: 315
<212> TYPE: DNA
<213> ORGANISM: Human

<400> SEQUENCE: 28

```
atgagaggtg ccacgcgagt ctcaatcatg ctcctcctag taactgtgtc tgactgtgct     60
```

```
gtgatcacag gggcctgtga gcgggatgtc cagtgtgggg caggcacctg ctgtgccatc    120
agcctgtggc ttcgagggct gcggatgtgc accccgctgg ggcgggaagg cgaggagtgc    180
caccccggca gccacaagat ccccttcttc aggaaacgca agcaccacac ctgtccttgc    240
ttgcccaacc tgctgtgctc caggttcccg gacggcaggt accgctgctc catggacttg    300
aagaacatca atttt                                                    315

<210> SEQ ID NO 29
<211> LENGTH: 315
<212> TYPE: DNA
<213> ORGANISM: Human

<400> SEQUENCE: 29
atgagaggtg ccacgcgagt ctcaatcatg ctcctcctag taactgtgtc tgactgtgct     60
gtgatcacag gggcctgtga gcgggatgtc cagtgtgggg caggcacctg ctgtgccatc    120
agcctgtggc ttcgagggct gcggatgtgc accccgctgg ggcgggaagg cgaggagtgc    180
caccccggca gccacaaggt ccccttcttc aggaaacgca agcaccacac ctgtccttgc    240
ttgcccaacc tgctgtgctc caggttcccg gacggcaggt accgctgctc catggacttg    300
aagaacatca atttt                                                    315

<210> SEQ ID NO 30
<211> LENGTH: 382
<212> TYPE: DNA
<213> ORGANISM: Human

<400> SEQUENCE: 30
gaattcgccc ttccaccatg agaggtgcca cgcgagtctc aatcatgctc ctcctagtaa     60
ctgtgtctga ctgtgctgtg atcacagggg cctgtgagcg ggatgtccag tgtggggcag    120
gcacctgctg tgccatcagc ctgtggcttc gagggctgcg gatgtgcacc ccgctggggc    180
gggaaggcga ggagtgccac cccggcagcc acaaggtccc cttcttcagg aaacgcaagc    240
accacacctg tccttgcttg cccaacctgc tgtgctccag gttcccggac ggcaggtacc    300
gctgctccat ggacttgaag aacatcaatt tttaggcgct tgcctggtct caggataccc    360
accatccttt cctgagctcg ag                                            382

<210> SEQ ID NO 31
<211> LENGTH: 10
<212> TYPE: PRT
<213> ORGANISM: Human
<220> FEATURE:
<221> NAME/KEY: UNSURE
<222> LOCATION: (7)
<223> OTHER INFORMATION: Xaa is an unidentified residue.

<400> SEQUENCE: 31

Ala Val Ile Thr Gly Ala Xaa Glu Arg Asp
                5                   10

<210> SEQ ID NO 32
<211> LENGTH: 26
<212> TYPE: DNA
<213> ORGANISM: Artificial Sequence
<220> FEATURE:
<223> OTHER INFORMATION: primer

<400> SEQUENCE: 32
gtcgaccacc atgagaggtg ccacgc                                         26
```

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
actagtcgca gaactggtag gtatgg                                           26

<210> SEQ ID NO 34
<211> LENGTH: 80
<212> TYPE: PRT
<213> ORGANISM: Dendroaspis polylepis

<400> SEQUENCE: 34

Ala Val Ile Thr Gly Ala Cys Glu Arg Asp Leu Gln Cys Gly Lys Gly
                  5                  10                  15
Thr Cys Cys Ala Val Ser Leu Trp Ile Lys Ser Val Arg Val Cys Thr
              20                  25                  30
Pro Val Gly Thr Ser Gly Glu Asp Cys His Pro Ala Ser His Lys Ile
          35                  40                  45
Pro Phe Ser Gly Gln Arg Met His His Thr Cys Pro Cys Ala Pro Asn
      50                  55                  60
Leu Ala Cys Val Gln Thr Ser Pro Lys Lys Phe Lys Cys Leu Ser Lys
 65                  70                  75                  80

<210> SEQ ID NO 35
<211> LENGTH: 1152
<212> TYPE: DNA
<213> ORGANISM: Human

<400> SEQUENCE: 35
atggcagccc agaatggaaa caccagtttc acacccaact ttaatccacc ccaagaccat      60
gcctcctccc tctcctttaa cttcagttat ggtgattatg acctccctat ggatgaggat     120
gaggacatga ccaagacccg gaccttcttc gcagccaaga tcgtcattgg cattgcactg     180
gcaggcatca tgctggtctg cggcatcggt aactttgtct ttatcgctgc cctcacccgc     240
tataagaagt tgcgcaacct caccaatctg ctcattgcca acctggccat ctccgacttc     300
ctggtggcca tcatctgctg ccccttcgag atggactact acgtggtacg gcagctctcc     360
tgggagcatg gccacgtgct ctgtgcctcc gtcaactacc tgcgcaccgt ctccctctac     420
gtctccacca atgccttgct ggccattgcc attgacagat atctcgccat cgttcacccc     480
ttgaaaccac ggatgaatta tcaaacggcc tccttcctga tcgccttggt ctggatggtg     540
tccattctca ttgccatccc atcggcttac tttgcaacag aaaccgtcct ctttattgtc     600
aagagccagg agaagatctt ctgtggccag atctggcctg tggatcagca gctctactac     660
aagtcctact tcctcttcat ctttggtgtc gagttcgtgg gccctgtggt caccatgacc     720
ctgtgctatg ccaggatctc ccgggagctc tggttcaagg cagtccctgg gttccagacg     780
gagcagattc gcaagcggct gcgctgccgc aggaagacgg tcctggtgct catgtgcatt     840
ctcacggcct atgtgctgtg ctgggcaccc ttctacggtt tcaccatcgt tcgtgacttc     900
ttccccactg tgttcgtgaa ggaaaagcac tacctcactg ccttctacgt ggtcgagtgc     960
atcgccatga gcaacagcat gatcaacacc gtgtgcttcg tgacggtcaa gaacaacacc    1020
atgaagtact tcaagaagat gatgctgctg cactggcgtc cctcccagcg ggggagcaag    1080

```
tccagtgctg accttgacct cagaaccaac ggggtgccca ccacagaaga agtggactgt    1140
atcaggctga ag                                                        1152
```

<210> SEQ ID NO 36
<211> LENGTH: 384
<212> TYPE: PRT
<213> ORGANISM: Human

<400> SEQUENCE: 36

```
Met Ala Ala Gln Asn Gly Asn Thr Ser Phe Thr Pro Asn Phe Asn Pro
                 5                  10                  15

Pro Gln Asp His Ala Ser Ser Leu Ser Phe Asn Phe Ser Tyr Gly Asp
            20                  25                  30

Tyr Asp Leu Pro Met Asp Glu Asp Glu Asp Met Thr Lys Thr Arg Thr
        35                  40                  45

Phe Phe Ala Ala Lys Ile Val Ile Gly Ile Ala Leu Ala Gly Ile Met
    50                  55                  60

Leu Val Cys Gly Ile Gly Asn Phe Val Phe Ile Ala Ala Leu Thr Arg
65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
            100                 105                 110

Tyr Tyr Val Val Arg Gln Leu Ser Trp Glu His Gly His Val Leu Cys
        115                 120                 125

Ala Ser Val Asn Tyr Leu Arg Thr Val Ser Leu Tyr Val Ser Thr Asn
    130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
            180                 185                 190

Thr Glu Thr Val Leu Phe Ile Val Lys Ser Gln Glu Lys Ile Phe Cys
        195                 200                 205

Gly Gln Ile Trp Pro Val Asp Gln Gln Leu Tyr Tyr Lys Ser Tyr Phe
    210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
            260                 265                 270

Thr Val Leu Val Leu Met Cys Ile Leu Thr Ala Tyr Val Leu Cys Trp
        275                 280                 285

Ala Pro Phe Tyr Gly Phe Thr Ile Val Arg Asp Phe Phe Pro Thr Val
    290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
            340                 345                 350

Arg Pro Ser Gln Arg Gly Ser Lys Ser Ser Ala Asp Leu Asp Leu Arg
```

```
                    355                 360                 365
Thr Asn Gly Val Pro Thr Thr Glu Glu Val Asp Cys Ile Arg Leu Lys
                370                 375                 380      384
```

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
gtcgacatgg agaccactgt ggggaccctg                                    30

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
actagtttat ttcagtcgga tgcagtccac                                    30

<210> SEQ ID NO 39
<211> LENGTH: 1179
<212> TYPE: DNA
<213> ORGANISM: Rat

<400> SEQUENCE: 39
atggagacca ctgtggggac cctgggcgag aataccacaa acactttcac cgacttcttt     60
tctgcacgtg atggcagtgg agccgaaacc tccccttgc cattcacttt cagctatggt    120
gactatgaca tgccctcgga tgaagaggag gatgtgacca actctcggac tttctttgct    180
gccaagattg tcattggcat ggctttggtg ggcatcatgc tggtgtgtgg catcggcaac    240
ttcatcttca tcactgcgct ggcccgctac aaaaagcttc gcaacctcac caacctgctt    300
atcgccaacc tggccatttc ggacttcctg gtagccatcg tgctgccc ctttgagatg     360
gactactatg tggtacgcca gctctcctgg gagcacggcc atgtcctgtg cgcctccgtc    420
aactacttgc gcaccgtctc cctctacgtg tccactaacg ccctactggc cattgccatt    480
gacaggtatc tggccattgt gcacccgctg agaccgcgga tgaagtgtca acggctgca    540
ggcctgatct tcctggtgtg gtctgtgtcc atcctcatcg ccatcccagc cgcctacttc    600
accactgaga cggtgttggt catcgtggaa agccaggaga gatcttctg cggccagatc    660
tggccggtgg atcagcagtt ctactacagg tcctatttcc ttttggtctt cggcctcgag    720
ttcgtgggtc ctgtaatcgc catgaccctg tgctatgcca gggtgtcccg agagctctgg    780
ttcaaggcgg tgcccggctt ccagacagag cagatccgcc ggaggctgcg ctgtcgccga    840
cggacggtac tggggctcgt gtgcgtcctt tccgcctatg tgctgtgctg gctcccttc     900
tatggcttca ccatcgtgcg tgacttcttc ccctccgtgt tgtgaaaga aagcactac     960
ctcaccgcct tttatgtggt ggagtgcatc gccatgagca cagtatgat caatacgctg    1020
tgctttgtga ctgtcaggaa taacaccagt aagtacctca agaggatcct gcggctccag    1080
tggagggcct ctcctagcgg gagcaaggcc agcgctgacc tcgacctcag gaccacgggg    1140
attcctgcca cggaggaggt ggactgcatc cgactgaaa                           1179

<210> SEQ ID NO 40

<211> LENGTH: 393
<212> TYPE: PRT
<213> ORGANISM: Rat

<400> SEQUENCE: 40

```
Met Glu Thr Thr Val Gly Thr Leu Gly Glu Asn Thr Thr Asn Thr Phe
                 5                   10                  15

Thr Asp Phe Phe Ser Ala Arg Asp Gly Ser Gly Ala Glu Thr Ser Pro
             20                  25                  30

Leu Pro Phe Thr Phe Ser Tyr Gly Asp Tyr Asp Met Pro Ser Asp Glu
         35                  40                  45

Glu Glu Asp Val Thr Asn Ser Arg Thr Phe Phe Ala Ala Lys Ile Val
     50                  55                  60

Ile Gly Met Ala Leu Val Gly Ile Met Leu Val Cys Gly Ile Gly Asn
65                  70                  75                  80

Phe Ile Phe Ile Thr Ala Leu Ala Arg Tyr Lys Lys Leu Arg Asn Leu
                 85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
        115                 120                 125

Ser Trp Glu His Gly His Val Leu Cys Ala Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Ala Gly Leu Ile Phe Leu Val Trp Ser Val Ser Ile Leu
            180                 185                 190

Ile Ala Ile Pro Ala Ala Tyr Phe Thr Thr Glu Thr Val Leu Val Ile
        195                 200                 205

Val Glu Ser Gln Glu Lys Ile Phe Cys Gly Gln Ile Trp Pro Val Asp
    210                 215                 220

Gln Gln Phe Tyr Tyr Arg Ser Tyr Phe Leu Leu Val Phe Gly Leu Glu
225                 230                 235                 240

Phe Val Gly Pro Val Ile Ala Met Thr Leu Cys Tyr Ala Arg Val Ser
                245                 250                 255

Arg Glu Leu Trp Phe Lys Ala Val Pro Gly Phe Gln Thr Glu Gln Ile
            260                 265                 270

Arg Arg Arg Leu Arg Cys Arg Arg Thr Val Leu Gly Leu Val Cys
        275                 280                 285

Val Leu Ser Ala Tyr Val Leu Cys Trp Ala Pro Phe Tyr Gly Phe Thr
    290                 295                 300

Ile Val Arg Asp Phe Phe Pro Ser Val Phe Val Lys Glu Lys His Tyr
305                 310                 315                 320

Leu Thr Ala Phe Tyr Val Val Glu Cys Ile Ala Met Ser Asn Ser Met
                325                 330                 335

Ile Asn Thr Leu Cys Phe Val Thr Val Arg Asn Asn Thr Ser Lys Tyr
            340                 345                 350

Leu Lys Arg Ile Leu Arg Leu Gln Trp Arg Ala Ser Pro Ser Gly Ser
        355                 360                 365

Lys Ala Ser Ala Asp Leu Asp Leu Arg Thr Thr Gly Ile Pro Ala Thr
    370                 375                 380

Glu Glu Val Asp Cys Ile Arg Leu Lys
```

<210> SEQ ID NO 41
<211> LENGTH: 31
<212> TYPE: DNA
<213> ORGANISM: Artificial Sequence
<220> FEATURE:
<223> OTHER INFORMATION: primer

<400> SEQUENCE: 41
cctcaccaay ctgctyatyg ccaacctggc c                            31

<210> SEQ ID NO 42
<211> LENGTH: 26
<212> TYPE: DNA
<213> ORGANISM: Artificial Sequence
<220> FEATURE:
<223> OTHER INFORMATION: primer

<400> SEQUENCE: 42
gtggtrcgsc agctctcctg ggagca                                  26

<210> SEQ ID NO 43
<211> LENGTH: 23
<212> TYPE: DNA
<213> ORGANISM: Artificial Sequence
<220> FEATURE:
<223> OTHER INFORMATION: primer

<400> SEQUENCE: 43
tcccgggagc tctggttcaa ggc                                     23

<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
gagtgcatcg ccatgagcaa cagcatg                                 27

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
ggcttgaacc agagctcccg gga                                     23

<210> SEQ ID NO 46
<211> LENGTH: 1266
<212> TYPE: DNA
<213> ORGANISM: Rat

<400> SEQUENCE: 46
atggtatcag ttctgtccaa cagggacctc cacacactgg ccccagctga agtgctgaac      60
tccacgtggg cctatctccc tgacacatac cagcctacct gccacatcat caacatggga     120
gaccagaacg gaaacacaag cttttgcacca gacttgaacc caccccaaga ccacgtctcc     180
ttgctcccct taaactacag ttatggagat tatgacatcc ccctggatga cgatgaggat     240
gtgaccaaga cacagacctt cttttgcagcc aaaatcgtca ttggcgtagc cctggcaggc     300

```
atcatgctag tctgcggcgt tggcaacttt gtcttcattg ctgccctcgc ccgctacaag      360
aagctgcgca accttaccaa cctcctcatc gctaacctgg ccatctctga cttcctggtg      420
gcgatcgtct gctgcccctt tgagatggac tactacgtag tacgtcagct ttcctgggag      480
catggtcacg tgctttgtgc ctccgtcaac taccttcgta cagtctccct gtacgtctcc      540
accaatgctc tgctggccat cgctattgac agatatctcg ctattgtcca ccccttaaaa      600
cggatgaatt accagaccgc ctccttcctg atcgctttgg tctggatggt ctccatcctc      660
atcgccatcc catctgccta cttcaccaca gaaaccatcc ttgttatcgt caagaatcag      720
gaaaagctct tctgtggtca gatctggccc gtggaccagc agctctacta caaatcctac      780
ttcctcttcg tcttcgggct tgagttcgtg ggtcccgtgg tcactatgac cctgtgctat      840
gccaggatct cccaggagct ctggttcaag gctgtacctg gtttccagac ggagcagatc      900
cgcaagcgac tgcgctgccg ccgaaagaca gtgctattgc tcatgggtat cctcacagcc      960
tacgtgctgt gctgggcgcc tttctatggc tttaccatag tgcgagactt cttccccacg     1020
ctggttgtga aggagaagca ctacctcacc gccttctatg tcgtcgagtg catcgccatg     1080
agcaacagca tgatcaatac tatatgcttc gtgacggtca agaacaacac catgaaatac     1140
ttcaagaaga tgctgctgct gcactggcgg ccctctcact acgggagtaa gtccagcgcg     1200
gacctcgacc tcaaaaccag tggggttcct gccaccgaag aggtggactg tatcaggcta     1260
aagtag                                                                1266
```

<210> SEQ ID NO 47
<211> LENGTH: 421
<212> TYPE: PRT
<213> ORGANISM: Rat

<400> SEQUENCE: 47

```
Met Val Ser Val Leu Ser Asn Arg Asp Leu His Thr Leu Ala Pro Ala
              5                  10                  15

Glu Val Leu Asn Ser Thr Trp Ala Tyr Leu Pro Asp Thr Tyr Gln Pro
         20                  25                  30

Thr Cys His Ile Ile Asn Met Gly Asp Gln Asn Gly Asn Thr Ser Phe
     35                  40                  45

Ala Pro Asp Leu Asn Pro Pro Gln Asp His Val Ser Leu Leu Pro Leu
 50                  55                  60

Asn Tyr Ser Tyr Gly Asp Tyr Asp Ile Pro Leu Asp Asp Asp Glu Asp
 65                  70                  75                  80

Val Thr Lys Thr Gln Thr Phe Phe Ala Ala Lys Ile Val Ile Gly Val
                 85                  90                  95

Ala Leu Ala Gly Ile Met Leu Val Cys Gly Val Gly Asn Phe Val Phe
            100                 105                 110

Ile Ala Ala Leu Ala Arg Tyr Lys Lys Leu Arg Asn Leu Thr Asn Leu
        115                 120                 125

Leu Ile Ala Asn Leu Ala Ile Ser Asp Phe Leu Val Ala Ile Val Cys
    130                 135                 140

Cys Pro Phe Glu Met Asp Tyr Tyr Val Val Arg Gln Leu Ser Trp Glu
145                 150                 155                 160

His Gly His Val Leu Cys Ala Ser Val Asn Tyr Leu Arg Thr Val Ser
                165                 170                 175

Leu Tyr Val Ser Thr Asn Ala Leu Leu Ala Ile Ala Ile Asp Arg Tyr
            180                 185                 190
```

-continued

```
Leu Ala Ile Val His Pro Leu Lys Arg Met Asn Tyr Gln Thr Ala Ser
        195                 200                 205

Phe Leu Ile Ala Leu Val Trp Met Val Ser Ile Leu Ile Ala Ile Pro
    210                 215                 220

Ser Ala Tyr Phe Thr Thr Glu Thr Ile Leu Val Ile Val Lys Asn Gln
225                 230                 235                 240

Glu Lys Leu Phe Cys Gly Gln Ile Trp Pro Val Asp Gln Gln Leu Tyr
                245                 250                 255

Tyr Lys Ser Tyr Phe Leu Phe Val Phe Gly Leu Glu Phe Val Gly Pro
                260                 265                 270

Val Val Thr Met Thr Leu Cys Tyr Ala Arg Ile Ser Gln Glu Leu Trp
                275                 280                 285

Phe Lys Ala Val Pro Gly Phe Gln Thr Glu Gln Ile Arg Lys Arg Leu
    290                 295                 300

Arg Cys Arg Arg Lys Thr Val Leu Leu Leu Met Gly Ile Leu Thr Ala
305                 310                 315                 320

Tyr Val Leu Cys Trp Ala Pro Phe Tyr Gly Phe Thr Ile Val Arg Asp
                325                 330                 335

Phe Phe Pro Thr Leu Val Val Lys Glu Lys His Tyr Leu Thr Ala Phe
                340                 345                 350

Tyr Val Val Glu Cys Ile Ala Met Ser Asn Ser Met Ile Asn Thr Ile
                355                 360                 365

Cys Phe Val Thr Val Lys Asn Asn Thr Met Lys Tyr Phe Lys Lys Met
                370                 375                 380

Leu Leu Leu His Trp Arg Pro Ser His Tyr Gly Ser Lys Ser Ser Ala
385                 390                 395                 400

Asp Leu Asp Leu Lys Thr Ser Gly Val Pro Ala Thr Glu Glu Val Asp
                405                 410                 415

Cys Ile Arg Leu Lys
                420

<210> SEQ ID NO 48
<211> LENGTH: 393
<212> TYPE: PRT
<213> ORGANISM: Mouse

<400> SEQUENCE: 48

Met Glu Thr Thr Val Gly Ala Leu Gly Glu Asn Thr Asp Thr Phe
                5                   10                  15

Thr Asp Phe Phe Ser Ala Leu Asp Gly His Glu Ala Gln Thr Gly Ser
            20                  25                  30

Leu Pro Phe Thr Phe Ser Tyr Gly Asp Tyr Asp Met Pro Leu Asp Glu
        35                  40                  45

Glu Glu Asp Val Thr Asn Ser Arg Thr Phe Phe Ala Ala Lys Ile Val
    50                  55                  60

Ile Gly Met Ala Leu Val Gly Ile Met Leu Val Cys Gly Ile Gly Asn
65                  70                  75                  80

Phe Ile Phe Ile Thr Ala Leu Ala Arg Tyr Lys Lys Leu Arg Asn Leu
                85                  90                  95

Thr Asn Leu Leu Ile Ala Asn Leu Ala Ile Ser Asp Phe Leu Val Ala
                100                 105                 110

Ile Val Cys Cys Pro Phe Glu Met Asp Tyr Tyr Val Val Arg Gln Leu
            115                 120                 125

Ser Trp Glu His Gly His Val Leu Cys Ala Ser Val Asn Tyr Leu Arg
    130                 135                 140
```

-continued

```
Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
            165                 170                 175

Gln Thr Ala Ala Gly Leu Ile Phe Leu Val Trp Ser Val Ser Ile Leu
        180                 185                 190

Ile Ala Ile Pro Ala Ala Tyr Phe Thr Thr Glu Thr Val Leu Val Ile
    195                 200                 205

Val Glu Arg Gln Glu Lys Ile Phe Cys Gly Gln Ile Trp Pro Val Asp
210                 215                 220

Gln Gln Phe Tyr Tyr Arg Ser Tyr Phe Leu Leu Val Phe Gly Leu Glu
225                 230                 235                 240

Phe Val Gly Pro Val Val Ala Met Thr Leu Cys Tyr Ala Arg Val Ser
            245                 250                 255

Arg Glu Leu Trp Phe Lys Ala Val Pro Gly Phe Gln Thr Glu Gln Ile
        260                 265                 270

Arg Arg Thr Val Arg Cys Arg Arg Thr Val Leu Gly Leu Val Cys
    275                 280                 285

Val Leu Ser Ala Tyr Val Leu Cys Trp Ala Pro Phe Tyr Gly Phe Thr
290                 295                 300

Ile Val Arg Asp Phe Phe Pro Ser Val Phe Val Lys Glu Lys His Tyr
305                 310                 315                 320

Leu Thr Ala Phe Tyr Val Val Glu Cys Ile Ala Met Ser Asn Ser Met
            325                 330                 335

Ile Asn Thr Leu Cys Phe Val Thr Val Arg Asn Asn Thr Ser Lys Tyr
        340                 345                 350

Leu Lys Arg Ile Leu Arg Leu Gln Trp Arg Ala Ser Pro Ser Gly Ser
    355                 360                 365

Lys Ala Ser Ala Asp Leu Asp Leu Arg Thr Thr Gly Ile Pro Ala Thr
370                 375                 380

Glu Glu Val Asp Cys Ile Arg Leu Lys
385                 390

<210> SEQ ID NO 49
<211> LENGTH: 381
<212> TYPE: PRT
<213> ORGANISM: Mouse

<400> SEQUENCE: 49

Met Gly Pro Gln Asn Arg Asn Thr Ser Phe Ala Pro Asp Leu Asn Pro
                5                   10                  15

Pro Gln Asp His Val Ser Leu Asn Tyr Ser Tyr Gly Asp Tyr Asp Leu
            20                  25                  30

Pro Leu Gly Glu Asp Glu Asp Val Thr Lys Thr Gln Thr Phe Phe Ala
        35                  40                  45

Ala Lys Ile Val Ile Gly Val Ala Leu Ala Gly Ile Met Leu Val Cys
    50                  55                  60

Gly Ile Gly Asn Phe Val Phe Ile Ala Ala Leu Ala Arg Tyr Lys Lys
65                  70                  75                  80

Leu Arg Asn Leu Thr Asn Leu Leu Ile Ala Asn Leu Ala Ile Ser Asp
            85                  90                  95

Phe Leu Val Ala Ile Val Cys Cys Pro Phe Glu Met Asp Tyr Tyr Val
        100                 105                 110

Val Arg Gln Leu Ser Trp Ala His Gly His Val Leu Cys Ala Ser Val
```

```
                115                 120                 125
Asn Tyr Leu Arg Thr Val Ser Leu Tyr Val Ser Thr Asn Ala Leu Leu
        130                 135                 140

Ala Ile Ala Ile Asp Arg Tyr Leu Ala Ile Val His Pro Leu Lys Pro
145                 150                 155                 160

Arg Met Asn Tyr Gln Thr Ala Ser Phe Leu Ile Ala Leu Val Trp Met
                165                 170                 175

Val Ser Ile Leu Ile Ala Val Pro Ser Ala Tyr Phe Thr Thr Glu Thr
            180                 185                 190

Ile Leu Val Ile Val Lys Asn Gln Glu Lys Ile Phe Cys Gly Gln Ile
        195                 200                 205

Trp Ser Val Asp Gln Gln Leu Tyr Tyr Lys Ser Tyr Phe Leu Phe Val
    210                 215                 220

Phe Gly Leu Glu Phe Val Gly Pro Val Val Thr Met Thr Leu Cys Tyr
225                 230                 235                 240

Ala Arg Ile Ser Gln Glu Leu Trp Phe Lys Ala Val Pro Gly Phe Gln
                245                 250                 255

Thr Glu Gln Ile Arg Lys Arg Leu Arg Cys Arg Arg Lys Thr Val Leu
            260                 265                 270

Leu Leu Met Gly Ile Leu Thr Ala Tyr Val Leu Cys Trp Ala Pro Phe
        275                 280                 285

Tyr Gly Phe Thr Ile Val Arg Asp Phe Phe Pro Thr Val Val Val Lys
    290                 295                 300

Glu Lys His Tyr Leu Thr Ala Phe Tyr Val Val Glu Cys Ile Ala Met
305                 310                 315                 320

Ser Asn Ser Met Ile Asn Thr Ile Cys Phe Val Thr Val Lys Asn Asn
                325                 330                 335

Thr Met Lys Tyr Phe Lys Lys Met Leu Arg Leu His Trp Arg Pro Ser
            340                 345                 350

His Tyr Gly Ser Lys Ser Ser Ala Asp Leu Asp Leu Lys Thr Ser Gly
        355                 360                 365

Val Pro Ala Thr Glu Glu Val Asp Cys Ile Arg Leu Lys
370                 375                 380

<210> SEQ ID NO 50
<211> LENGTH: 1179
<212> TYPE: DNA
<213> ORGANISM: Mouse

<400> SEQUENCE: 50
atggagacca ctgtcggggc tctgggtgag aataccacag acaccttcac cgacttcttt      60
tctgcactcg atggccatga agcccaaacc ggctcgttac cattcacttt cagctacggt     120
gactatgaca tgccectgga tgaagaggaa gatgtgacca attctcggac tttctttgct     180
gccaagattg tcattggcat ggctttggtg gtatcatgc tagtgtgtgg catcggcaac      240
ttcatcttta tcactgccct ggcccgctac aaaaagctcc gcaacctcac caacctgctt     300
atcgccaacc tggccatttc agacttcctc gtggccatcg tgctgccc ctttgagatg       360 gactactatg tggtgcgcca gctctcctgg gagcatggtc atgtcctgtg cgcctctgtc     420
aactacttgc gtaccgtctc cctctacgtc tccactaacg ccctactggc cattgccatt     480
gacaggtatc tggccattgt gcacccgctg agaccgcgga tgaagtgtca acagccgcc      540 ggcctgatct tcctggtgtg gtcagtatcc atcctcatcg ccattccagc tgcctacttc     600
accactgaga ccgtgctggt catcgtggag agacaggaga agatcttctg tggtcagatc     660
```

```
tggccggtgg atcagcagtt ctactacagg tcctatttcc ttttggtttt cggcctcgag    720
ttcgtgggcc ccgtagtcgc catgaccttg tgctatgcca gggtgtcccg ggagctctgg    780
ttcaaggcgg tgccaggctt ccagacagag cagatccgcc ggacggtgcg ctgccgccgc    840
aggacggtgc tggggctcgt gtgcgtcctc tctgcctatg tgctgtgctg ggctcccttc    900
tatggcttca ctatcgtgcg tgacttcttc ccctccgtgt tgtgaagga aagcactac     960 ctcaccgcct tctatgtggt ggagtgcatc gccatgagca acagcatgat caatacgctc   1020
tgctttgtga ctgtcaggaa taacaccagt aagtacctca agaggatcct gcggcttcag   1080
tggagggcct ctcccagcgg gagcaaggcc agcgctgacc tcgacctcag gaccacggga   1140
atacctgcca ccgaggaggt ggactgcatc cgactgaaa                          1179

<210> SEQ ID NO 51
<211> LENGTH: 1143
<212> TYPE: DNA
<213> ORGANISM: Mouse

<400> SEQUENCE: 51
atgggacccc agaacagaaa cactagcttt gcaccagact tgaatccacc ccaagaccat     60
gtctccttaa actacagtta tggtgattat gacctccccc tgggtgagga tgaggatgtg    120
accaagacac agaccttctt tgcagccaaa attgtcattg gcgtggcact ggcaggcatc    180
atgctggtct gcggcattgg caactttgtc ttcattgctg ccctcgcccg ctacaagaag    240
ctgcgcaacc ttaccaacct cctcattgct aacctggcca tctctgactt cctggtggcg    300
atcgtctgct gccccttga gatggactat tatgtagtac ggcagctttc ctgggcgcat    360
ggtcacgtgc tttgtgcctc cgtcaactac cttcgtacgg tctccctgta cgtctccacc    420
aacgctctgc tggccatcgc tattgacaga tacctgcta ttgtccaccc tttgaaacca    480
cggatgaatt atcagaccgc ttccttcctg atcgctttgg tctggatggt ctccatcctc    540
atcgctgtcc catctgccta cttcaccaca gaaaccatcc tcgttatcgt caagaatcaa    600
gaaaaaatct tctgtggtca gatctggtcg gtggaccagc agctctacta caaatcctac    660
ttcctcttcg tcttcgggct tgagttcgtg gtcccgtgg tcactatgac cctgtgctat    720
gccaggatcc cccaagagct ctggttcaag gctgtacctg gcttccagac ggagcaaatc    780
cgcaagcggc tgcgttgccg ccgcaagaca gtgctactgc tcatgggcat cctcacagcc    840
tacgtgctgt gctgggcgcc gttctatggc tttaccatag tgcgagactt cttccccacg    900
gtagttgtga aggagaagca ctacctcacc gccttctacg tcgtggagtg cattgccatg    960
agcaacagca tgatcaatac tatatgcttc gtgacggtca gaacaacac catgaaatac   1020 ttcaagaaga tgctgcggct ccactggcgg ccctctcact acgggagtaa gtccagcgct   1080
gacctcgacc tcaaaaccag cggggtgcct gccactgaag aggtggattg tatcagacta   1140
aag                                                                1143

<210> SEQ ID NO 52
<211> LENGTH: 88
<212> TYPE: DNA
<213> ORGANISM: Artificial Sequence
<220> FEATURE:
<223> OTHER INFORMATION: Primer

<400> SEQUENCE: 52
tatggcggtg attaccggtg cgtgcgaacg tgatgtgcag tgcggtgcgg gtacctgctg     60
```
cgcgattagc ctgtggctgc gtggtctg         88

<210> SEQ ID NO 53
<211> LENGTH: 92
<212> TYPE: DNA
<213> ORGANISM: Artificial Sequence
<220> FEATURE:
<223> OTHER INFORMATION: Primer

<400> SEQUENCE: 53
cgtatgtgca ccccgctggg tcgtgaaggt gaagaatgcc atccgggtag ccataaagtg    60
ccgttcttcc gtaaacgtaa acatcatacc tg    92

<210> SEQ ID NO 54
<211> LENGTH: 86
<212> TYPE: DNA
<213> ORGANISM: Artificial Sequence
<220> FEATURE:
<223> OTHER INFORMATION: Primer

<400> SEQUENCE: 54
cccgtgcctg ccgaacctgc tgtgcagccg tttcccggat ggtcgttatc gttgcagcat    60
ggatctgaaa aacattaact tttagg    86

<210> SEQ ID NO 55
<211> LENGTH: 94
<212> TYPE: DNA
<213> ORGANISM: Artificial Sequence
<220> FEATURE:
<223> OTHER INFORMATION: Primer

<400> SEQUENCE: 55
cacatacgca gaccacgcag ccacaggcta atcgcgcagc aggtacccgc accgcactgc    60
acatcacgtt cgcacgcacc ggtaatcacc gcca    94

<210> SEQ ID NO 56
<211> LENGTH: 93
<212> TYPE: DNA
<213> ORGANISM: Artificial Sequence
<220> FEATURE:
<223> OTHER INFORMATION: Primer

<400> SEQUENCE: 56
aggcacgggc aggtatgatg tttacgttta cggaagaacg gcactttatg gctacccgga    60
tggcattctt caccttcacg acccagcggg gtg    93

<210> SEQ ID NO 57
<211> LENGTH: 81
<212> TYPE: DNA
<213> ORGANISM: Artificial Sequence
<220> FEATURE:
<223> OTHER INFORMATION: Primer

<400> SEQUENCE: 57
gatccctaaa agttaatgtt tttcagatcc atgctgcaac gataacgacc atccgggaaa    60
cggctgcaca gcaggttcgg c    81

<210> SEQ ID NO 58
<211> LENGTH: 258
<212> TYPE: DNA
<213> ORGANISM: Artificial Sequence
<220> FEATURE:
<223> OTHER INFORMATION: synthetic DNA -continued

```
<400> SEQUENCE: 58
gcggtgatta ccggtgcgtg cgaacgtgat gtgcagtgcg gtgcgggtac ctgctgcgcg      60
attagcctgt ggctgcgtgg tctgcgtatg tgcaccccgc tgggtcgtga aggtgaagaa     120
tgccatccgg gtagccataa agtgccgttc ttccgtaaac gtaaacatca tacctgcccg     180
tgcctgccga acctgctgtg cagccgtttc ccggatggtc gttatcgttg cagcatggat     240
ctgaaaaaca ttaactttt                                                   258
```

PHYSIOLOGICALLY ACTIVE PEPTIDE AND USE THEREOF

This application is the National Phase filing of International Patent Application No. PCT/JP01/06162, filed 17 Jul. 2001.

1. Field of the Invention

The present invention relates to (1) a peptide characterized by containing the same or substantially the same amino acid sequence as the amino acid sequence represented by SEQ ID NO: 20 or SEQ ID NO: 21, or a salt thereof, and (2) a method of screening a compound or its salt useful as a preventive/therapeutic agent for digestive diseases, which comprises using a protein containing the same or substantially the same amino acid sequence as the amino acid sequence represented by SEQ ID NO: 1 or SEQ ID NO:36, which is an orphan receptor protein, or a salt thereof, and a peptide containing the same or substantially the same amino acid sequence as the amino acid sequence represented by SEQ ID NO: 20 or SEQ ID NO: 21, or a salt thereof; or the like.

2. Background Art

Important biological functions including maintenance of homeostasis in the living body, reproduction, development of individuals, metabolism, growth, control of the nervous, circulatory, immune, digestive or metabolic system, sensory adaptation, etc. are regulated by cells that receive endogenous factors such as various hormones and neurotransmitters or sensory stimulation such as light or odor, via specific receptors present on cell membranes reserved for these factors or stimulation and interact with them. Many of these receptors for hormones or neurotransmitters by such functional regulation are coupled to guanine nucleotide-binding proteins (hereinafter, sometimes merely referred to as G proteins), and are characterized by developing a variety of functions through intracellular signal transduction via activation of the G proteins. In addition, these receptor proteins possess common seven transmembrane domains. For the reasons above, these receptors are therefore collectively referred to as G protein-coupled receptors or seven transmembrane receptors. As stated above, it is known that various hormones or neurotransmitters and their receptor proteins are present and interact with each other to play important roles for regulating the biological functions. However, it is even now poorly understood if any other unknown substances (hormones, neurotransmitters, etc.) and receptors to these substances are present.

In recent years, the human gene has been clarified at an accelerating pace by accumulated sequence information through sequencing of human genomic DNA or various human tissue-derived cDNA at random and rapid progress in gene analysis technology. Based on the foregoing, it is manifested that there are many genes supposed to encode proteins with unknown functions. G protein-coupled receptors not only have seven transmembrane domains but many common sequences are present in their nucleic acids or amino acids, and can thus be clearly identified to be G protein-coupled receptors in such proteins. On the other hand, such G protein-coupled receptor genes are obtained by polymerase chain reaction (hereinafter abbreviated as PCR) utilizing such a similarity in structure (Nature Cell Biology, 2, 703–708 (2000)). In these G protein-coupled receptors thus obtained so far, ligands to some receptors that are subtypes having high homology in structure to known receptors may be readily predictable but in most cases, their endogenous ligands are unpredictable so that no ligands corresponding to these receptors are found. For this reason, these receptors are called orphan receptors. It is likely that unidentified endogenous ligands to such orphan receptors would take part in the biological phenomena poorly analyzed, because the ligands were unknown. And when such ligands are associated with important physiological effects or pathologic conditions, it is expected that development of these receptor agonists or antagonists will result in breakthrough of new drugs (Stadel, J. et al., TiPS, 18, 430–437, 1997; Marchese, A. et al., TiPS, 20, 370–375, 1999; Civelli, O. et al., Brain Res., 848, 63–65, 1999). Until now, however, there are few examples to actually identify ligands to orphan G protein-coupled receptors.

Recently, some groups attempted to investigate ligands to these orphan receptors and reported isolation of ligands, which are novel physiologically active peptides, and determination of their structures. Reinsheid et al. and Meunier et al. independently introduced cDNA encoding orphan G protein-coupled receptor LC132 or ORL1 into animal cells to express a receptor, isolated a novel peptide from porcine brain or rat brain extract using response of the receptor as an indicator, which was named orphanin FQ or nociceptin with reference to its response, and determined its sequence (Reinsheid, R. K. et al., Science, 270, 792–794, 1995; Meunier, J.-C. et al., Nature, 377, 532–535, 1995). This peptide was reported to be associated with a sense of pain. Further investigations on the receptor in knockout mouse revealed that the peptide was involved in memory (Manabe, T. et al., Nature, 394, 577–581, 1998).

Subsequently, novel peptides including PrRP (prolactin releasing peptide), orexin, apelin, ghrelin and GALP (galanin-like peptide), etc. were isolated as ligands to orphan G protein-coupled receptors (Hinuma, S. et al., Nature, 393, 272–276, 1998; Sakurai, T. et al., Cell, 92, 573–585, 1998; Tatemoto, K. et al., Bichem. Biophys. Res. Commun., 251, 471–476, 1998; Kojima, M. et al., Nature, 402, 656–660, 1999; Ohtaki, T. et al., J. Biol. Chem., 274, 37041–37045, 1999).

On the other hand, some receptors to physiologically active peptides hitherto unknown are unraveled by similar methods. It was unraveled that a receptor to motilin associated with contraction of intestinal tracts was GPR38 (Feighner, S. D. et al., Science, 284, 2184–2188, 1999). In addition, SLC-1 was identified to be a receptor to melanin-concentrating hormone (MCH) (Chambers, J. et al., Nature, 400, 261–265, 1999; Saito, Y. et al., Nature, 400, 265–269, 1999; Shimomura, Y. et al., Biochem. Biophys. Res. Commun., 261, 622–626, 1999; Lembo, P. M. C. et al., Nature Cell Biol., 1, 267–271, 1999; Bachner, D. et al., FEBS Lett., 457, 522–524, 1999). Also, GPR14 (SENR) was reported to be a receptor to urotensin II (Ames, R. S. et al., Nature, 401, 282–286, 1999; Mori, M. et al., Biochem. Biophys. Res. Commun., 265, 123–129, 1999; Nothacker, H. -P. et al., Nature Cell Biol., 1, 383–385, 1999, Liu, Q. et al., Biochem. Biophys. Res. Commun., 266, 174–178, 1999). It was shown that MCH took part in obesity since its knockout mice showed hypophagic and lean phenotype (Shimada, M. et al., Nature, 396, 670–674, 1998), and because its receptor was unraveled, it became possible to explore a receptor antagonist likely to be useful as an anti-obesity agent. It is further reported that urotensin II shows a potent action on the cardiocirculatory system, since it induces heart ischemia by intravenous injection to monkey (Ames, R. S. et al., Nature, 401, 282–286, 1999).

As described above, orphan receptors and ligands thereto are often engaged in a new physiological activity, elucidation of which will lead to development of novel drugs.

However, investigations of ligands to orphan receptors are accompanied by many difficulties. While the presence of many orphan receptors was unraveled to date, only a very few ligands were discovered for these receptors.

The present inventors found a novel receptor ZAQ, which is an orphan G protein-coupled receptor (a protein containing the same or substantially the same amino acid sequence as the amino acid sequence represented by SEQ ID NO: 1 of the specification: hereinafter sometimes simply referred to as ZAQ in the specification). However, it was heretofore unknown what the ligand was.

It has been the problem to find a ligand to the orphan receptor protein ZAQ and establish a method of screening a compound characterized by using ZAQ and a ligand thereto.

DISCLOSURE OF THE INVENTION

The present inventors found out a substance having a ligand activity specific to ZAQ, which was present in a milk extract, isolated the substance and determined its structure. The inventors also found a gene encoding a human type peptide of this active component, caused to express the gene in animal cells, and confirmed that a peptide-like substance capable of activating the ZAQ-expressed cells was secreted in the culture supernatant.

Based on these findings, the present inventors have found that drugs for the treatment of diseases mediated by ZAQ (ZAQ antagonists or agonists, etc., specifically agents for the prevention/treatment of digestive diseases, etc.) can be screened by the screening system using ZAQ and a ZAQ ligand peptide.

That is, the present invention relates to the following features:

(1) A peptide containing the same or substantially the same amino acid sequence as the amino acid sequence represented by SEQ ID NO: 20 or SEQ ID NO: 21, or a salt thereof;

(2) The peptide or its salt according to (1), which contains the same or substantially the same amino acid sequence as the amino acid sequence represented by SEQ ID NO: 21;

(3) The peptide or its salt according to (1), which contains the amino acid sequence represented by SEQ ID NO: 20;

(4) The peptide or its salt according to (1), which contains the amino acid sequence represented by SEQ ID NO: 21;

(5) The peptide or its salt according to (1), which is characterized by containing the same or substantially the same amino acid sequence as the amino acid sequence represented by SEQ ID NO: 22 or SEQ ID NO: 23;

(6) A polynucleotide comprising a polynucleotide encoding the peptide according to (1);

(7) The polynucleotide according to (6), which is a DNA;

(8) The DNA according to (7) containing the base sequence represented by SEQ ID NO: 26 or SEQ ID NO: 27;

(9) The DNA according to (7) containing the base sequence represented by SEQ ID NO: 28 or SEQ ID NO: 29;

(10) A recombinant vector containing the polynucleotide according to (6);

(11) A transformant transformed with the recombinant vector according to (10);

(12) A method of manufacturing the peptide or its salt according to (1), which comprises culturing the transformant of (11) and producing/accumulating the peptide according to (1);

(13) An antibody to the peptide or its salt according to (1);

(14) A method of screening a compound or its salt that alters the binding property between the peptide or its salt according to (1) and a protein containing the same or substantially the same amino acid sequence as the amino acid sequence represented by SEQ ID NO: 1 or its salt, which comprises using the peptide or its salt according to (1) and a protein containing the same or substantially the same amino acid sequence as the amino acid sequence represented by SEQ ID NO: 1, its partial peptide, or a salt thereof;

(15) A method of screening a compound or its salt that alters the binding property between the peptide or its salt according to (1) and a protein containing the same or substantially the same amino acid sequence as the amino acid sequence represented by SEQ ID NO: 36 or its salt, which comprises using the peptide or its salt according to (1) and a protein containing the same or substantially the same amino acid sequence as the amino acid sequence represented by SEQ ID NO: 36, its partial peptide, or a salt thereof;

(16) A kit for screening a compound or its salt that alters the binding property between the peptide or its salt according to (1) and a protein containing the same or substantially the same amino acid sequence as the amino acid sequence represented by SEQ ID NO: 1 or its salt, comprising the peptide or its salt according to (1) and a protein containing the same or substantially the same amino acid sequence as the amino acid sequence represented by SEQ ID NO: 1, its partial peptide, or a salt thereof;

(17) A kit for screening a compound or its salt that alters the binding property between the peptide or its salt according to (1) and a protein containing the same or substantially the same amino acid sequence as the amino acid sequence represented by SEQ ID NO: 36 or its salt, comprising the peptide or its salt according to (1) and a protein containing the same or substantially the same amino acid sequence as the amino acid sequence represented by SEQ ID NO: 36, its partial peptide, or a salt thereof;

(18) A compound or its salt that alters the binding property between the peptide or its salt according to (1) and a protein containing the same or substantially the same amino acid sequence as the amino acid sequence represented by SEQ ID NO: 1 or its salt, wherein the compound is obtainable using the screening method according to (14) or the screening kit according to (16);

(19) A compound or its salt that alters the binding property between the peptide or its salt according to (1) and a protein containing the same or substantially the same amino acid sequence as the amino acid sequence represented by SEQ ID NO: 36 or its salt, wherein the compound is obtainable using the screening method according to (15) or the screening kit according to (17);

(20) A pharmaceutical comprising the compound or its salts according to (18) or (19);

(21) The pharmaceutical according to (20), which is an agent for the prevention/treatment of digestive diseases;

(22) A pharmaceutical comprising the peptide or its salt according to (1);

(23) The pharmaceutical according to (22), which is an agent for the prevention/treatment of digestive diseases;

(24) A method for prevention/treatment of digestive diseases characterized by administering to a mammal an effective dose of the compound obtainable by using the method according to (14) or the kit according to (16), or a salt thereof, wherein the compound alters a binding property between the peptide or its salt according to (1) and the protein containing the same or substantially the same amino acid sequence as the amino acid sequence represented by SEQ ID NO: 1, or a salt thereof;

(25) A method for prevention/treatment of digestive diseases characterized by administering to a mammal an effective dose of the compound obtainable by using the method according to (15) or the kit according to (17), or a salt thereof, wherein the compound alters a binding property between the peptide or its salt according to (1) and the protein containing the same or substantially the same amino acid sequence as the amino acid sequence represented by SEQ ID NO: 36, or a salt thereof;

(26) Use of a compound or its salt for manufacturing an agent for the prevention/treatment of digestive diseases that alters the binding property between the peptide or its salt according to (1) and a protein containing the same or substantially the same amino acid sequence as the amino acid sequence represented by SEQ ID NO: 1 or its salt, wherein the compound is obtainable using the screening method according to (14) or the screening kit according to (16);

(27) Use of a compound or its salt for manufacturing an agent for the prevention/treatment of digestive diseases that alters the binding property between the peptide or its salt according to (1) and a protein containing the same or substantially the same amino acid sequence as the amino acid sequence represented by SEQ ID NO: 36 or its salt, wherein the compound is obtainable using the screening method according to (15) or the screening kit according to (17); etc.

The present invention further provides the following:

(28) The peptide or its salt according to (1), wherein substantially the same amino acid sequence as the amino acid sequence represented by SEQ ID NO: 20 or SEQ ID NO: 21 is an amino acid sequence having homology of at least about 60% (preferably at least about 70%, more preferably at least about 80%, much more preferably at least about 85%, further much more preferably at least about 90% and most preferably at least about 95%), to the amino acid sequence represented by SEQ ID NO: 20 or SEQ ID NO: 21;

(29) The peptide or its salt according to (1), wherein substantially the same amino acid sequence as the amino acid sequence represented by SEQ ID NO: 20 or SEQ ID NO: 21 is (i) an amino acid sequence represented by SEQ ID NO: 20 or SEQ ID NO: 21, of which 1 or 2 more (preferably approximately 1 to 30 and more preferably approximately 1 to 20) amino acids are deleted; (ii) an amino acid sequence represented by SEQ ID NO: 20 or SEQ ID NO: 21, to which 1 or 2 more (preferably approximately 1 to 40, more preferably approximately 1 to 30 and most preferably approximately 1 to 20) amino acids are added; (iii) an amino acid sequence represented by NO: 20 or SEQ ID NO: 21, in which 1 or 2 more (preferably approximately 1 to 30 and more preferably approximately 1 to 20) amino acids are substituted by other amino acids; and (iv) a combination of the above amino acid sequences;

(30) The method of screening according to (14), which comprises comparing (i) when the peptide or its salt according to (1) is brought in contact with a protein containing the same or substantially the same amino acid sequence as the amino acid sequence represented by SEQ ID NO: 1 or its partial peptide, or a salt thereof and (ii) when the peptide or its salt according to (1) and a test compound are brought in contact with a protein containing the same or substantially the same amino acid sequence as the amino acid sequence represented by SEQ ID NO: 1 or its partial peptide, or a salt thereof;

(31) A method of screening a compound or its salt that alters the binding property between the peptide or its salt according to (1) and a protein containing the same or substantially the same amino acid sequence as the amino acid sequence represented by SEQ ID NO: 1 or its salt, which comprises determining and comparing the binding amount of a labeled form of the peptide or its salt according to (1) to a protein containing the same or substantially the same amino acid sequence as the amino acid sequence represented by SEQ ID NO: 1, its partial peptide, or a salt thereof, (i) when the labeled form of the peptide or its salt according to (1) is brought in contact with a protein containing the same or substantially the same amino acid sequence as the amino acid sequence represented by SEQ ID NO: 1 or its partial peptide, or a salt thereof and (ii) when the labeled form of the peptide or its salt according to (1) and a test compound are brought in contact with a protein containing the same or substantially the same amino acid sequence as the amino acid sequence represented by SEQ ID NO: 1 or its partial peptide; or a salt thereof;

(32) A method of screening a compound or its salt that alters the binding property between the peptide or its salt according to (1) and a protein containing the same or substantially the same amino acid sequence as the amino acid sequence represented by SEQ ID NO: 1 or its salt, which comprises determining and comparing the binding amount of a labeled form of the peptide or its salt as set forth in (1) to the cell defined below, in cases (i) where a labeled form of the peptide or its salt according to (1) is brought in contact with the cell containing a protein having the same or substantially the same amino acid sequence as the amino acid sequence represented by SEQ ID NO: 1 and (ii) where a labeled form of the peptide or its salt according to (1) and a test compound are brought in contact with the cell containing a protein having the same or substantially the same amino acid sequence as the amino acid sequence represented by SEQ ID NO: 1;

(33) A method of screening a compound or its salt that alters the binding property between the peptide or its salt according to (1) and a protein containing the same or substantially the same amino acid sequence as the amino acid sequence represented by SEQ ID NO: 1 or its salt, which comprises determining and comparing the binding amount of a labeled form of the peptide or its salt as set forth in (1) to the cell membrane fraction defined below, in cases (i) when a labeled form of the peptide or its salt according to (1) is brought in contact with a cell membrane fraction containing a protein having the same or substantially the same amino acid sequence as the amino acid sequence represented by SEQ ID NO: 1 and (ii) when a labeled form of the peptide or its salt according to (1) and a test compound are brought in contact with the cell membrane fraction containing a protein having the same or substantially the same amino acid sequence as the amino acid sequence represented by SEQ ID NO: 1;

(34) A method of screening a compound or its salt that alters the binding property between the peptide or its salt according to (1) and a protein containing the same or substantially the same amino acid sequence as the amino acid sequence represented by SEQ ID NO: 1 or its salt, which comprises determining and comparing the binding amount of a labeled form of the peptide or its salt as set forth in (1) to the protein defined below, in cases (i) when a labeled form of the peptide or its salt according to (1) is brought in contact with a protein expressed in a cell membrane of a transformant by culturing the transformant transformed with a recombinant vector bearing a DNA containing a DNA encoding a protein containing the same or substantially the same amino acid sequence as the amino acid sequence represented by SEQ ID NO: 1, and (ii) when a labeled form of the peptide or its salt according to (1) and a test compound are brought in contact with a protein expressed in a cell membrane of a transformant by culturing the transformant transformed with a recombinant vector bearing a DNA containing a DNA encoding a protein containing the same or substantially the same amino acid sequence as the amino acid sequence represented by SEQ ID NO: 1;

(35) The screening method according to (15), wherein comparison is made between (i) when the peptide or its salt according to (1) is brought in contact with a protein containing the same or substantially the same amino acid sequence as the amino acid sequence represented by SEQ ID NO: 36 and (ii) when the peptide or its salt according to (1) and a test compound are brought in contact with a protein containing the same or substantially the same amino acid sequence as the amino acid sequence represented by SEQ ID NO: 36;

(36) A method of screening a compound or its salt that alters the binding property between the peptide or its salt according to (1) and a protein containing the same or substantially the same amino acid sequence as the amino acid sequence represented by SEQ ID NO: 36 or its salt, which comprises determining and comparing the binding amount of a labeled form of the peptide or its salt according to (1) to a protein containing the same or substantially the same amino acid sequence as the amino acid sequence represented by SEQ ID NO: 36, its partial peptide, or a salt thereof, (i) when the labeled form of the peptide or its salt according to (1) is brought in contact with a protein containing the same or substantially the same amino acid sequence as the amino acid sequence represented by SEQ ID NO: 36 or its partial peptide, or a salt thereof and (ii) when the labeled form of the peptide or its salt according to (1) and a test compound are brought in contact with a protein containing the same or substantially the same amino acid sequence as the amino acid sequence represented by SEQ ID NO: 36 or its partial peptide, or a salt thereof;

(37) A method of screening a compound or its salt that alters the binding property between the peptide or its salt according to (1) and a protein containing the same or substantially the same amino acid sequence as the amino acid sequence represented by SEQ ID NO: 36 or its salt, which comprises determining and comparing the binding amount of a labeled form of the peptide or its salt as set forth in (1) to the cell defined below, in cases (i) where a labeled form of the peptide or its salt according to (1) is brought in contact with the cell containing a protein having the same or substantially the same amino acid sequence as the amino acid sequence represented by SEQ ID NO: 36 and (ii) where a labeled form of the peptide or its salt according to (1) and a test compound are brought in contact with the cell containing a protein having the same or substantially the same amino acid sequence as the amino acid sequence represented by SEQ ID NO: 36;

(38) A method of screening a compound or its salt that alters the binding property between the peptide or its salt according to (1) and a protein containing the same or substantially the same amino acid sequence as the amino acid sequence represented by SEQ ID NO: 36 or its salt, which comprises determining and comparing the binding amount of a labeled form of the peptide or its salt as set forth in (1) to the cell membrane fraction defined below, in cases (i) when a labeled form of the peptide or its salt according to (1) is brought in contact with a cell membrane fraction containing a protein having the same or substantially the same amino acid sequence as the amino acid sequence represented by SEQ ID NO: 36 and (ii) when a labeled form of the peptide or its salt according to (1) and a test compound are brought in contact with the cell membrane fraction containing a protein having the same or substantially the same amino acid sequence as the amino acid sequence represented by SEQ ID NO: 36;

(39) A method of screening a compound or its salt that alters the binding property between the peptide or its salt according to (1) and a protein containing the same or substantially the same amino acid sequence as the amino acid sequence represented by SEQ ID NO: 36 or its salt, which comprises determining and comparing the binding amount of a labeled form of the peptide or its salt as set forth in (1) to the protein defined below, in cases (i) when a labeled form of the peptide or its salt according to (1) is brought in contact with a protein expressed in a cell membrane of a transformant by culturing the transformant transformed with a recombinant vector bearing a DNA containing a DNA encoding a protein containing the same or substantially the same amino acid sequence as the amino acid sequence represented by SEQ ID NO: 36, and (ii) when a labeled form of the peptide or its salt according to (1) and a test compound are brought in contact with a protein expressed in a cell membrane of a transformant by culturing the transformant transformed with a recombinant vector bearing a DNA containing a DNA encoding a protein containing the same or substantially the same amino acid sequence as the amino acid sequence represented by SEQ ID NO: 36;

(40) A compound or its salt that alters the binding property between (i) the peptide or its salt according to (1) and a protein containing the same or substantially the same amino acid sequence as the amino acid sequence represented by SEQ ID NO: 1 or a salt thereof, which is obtainable by the screening method according to (30) through (34);

(41) A compound or its salt that alters the binding property between (i) the peptide or its salt according to (1) and a protein containing the same or substantially the same amino acid sequence as the amino acid sequence represented by SEQ ID NO: 36 or a salt thereof, which is obtainable by the screening method according to (35) through (39);

(42) A pharmaceutical comprising the compound or its salt according to (40) or (41);

(43) The screening kit according to (16), comprising a cell containing a protein having the same or substantially the same amino acid sequence as the amino acid sequence represented by SEQ ID NO: 1;

(44) The screening kit according to (16), comprising a cell membrane fraction containing a protein having the same or substantially the same amino acid sequence as the amino acid sequence represented by SEQ ID NO: 1;

(45) The screening kit according to (16), comprising a protein expressed in a cell membrane of a transformant by culturing the transformant transformed with a recombinant vector bearing a DNA containing a DNA encoding a protein containing the same or substantially the same amino acid sequence as the amino acid sequence represented by SEQ ID NO: 1;

(46) The screening kit according to (17), comprising a cell containing a protein having the same or substantially the same amino acid sequence as the amino acid sequence represented by SEQ ID NO: 36;

(47) The screening kit according to (17), comprising a cell membrane fraction containing a protein having the same or substantially the same amino acid sequence as the amino acid sequence represented by SEQ ID NO: 36;

(48) The screening kit according to (17), comprising a protein expressed in a cell membrane of a transformant by culturing the transformant transformed with a recombinant vector bearing a DNA containing a DNA encoding a protein containing the same or substantially the same amino acid sequence as the amino acid sequence represented by SEQ ID NO: 36;

(49) A compound or its salt that alters the binding property between the peptide or its salt according to (1) and a protein containing the same or substantially the same amino acid sequence as the amino acid sequence represented by SEQ ID NO: 1 or a salt thereof, which is obtainable by the screening method according to (43) through (45);

(50) A compound or its salt that alters the binding property between the peptide or its salt according to (1) and a protein containing the same or substantially the same amino acid sequence as the amino acid sequence represented by SEQ ID NO: 36 or a salt thereof, which is obtainable by the screening method according to (46) through (48);

(51) A pharmaceutical comprising the compound or its salt according to (49) or (50);

(52) The pharmaceutical according to (42) or (51), which is an agent for the prevention/treatment of digestive diseases;

(53) A method of quantifying the peptide or its salt according to (1), which comprises contacting the antibody according to (13) with the peptide or its salt according to (1);

(54) A method of quantifying the peptide or its salt according to (1) in a sample fluid, which comprises competitively reacting the antibody according to (13) with a sample fluid and a labeled form of the peptide or its salt according to (1), and measuring the ratio of the labeled form of the peptide or its salt according to (1) in the sample fluid;

(54) A method of quantifying the peptide or its salt according to (1) in a sample fluid, which comprises reacting a sample fluid simultaneously or sequentially with the antibody of (13) immobilized on a carrier and a labeled form of the antibody according to (13) and then measuring the activity of a labeling agent on the immobilized carrier;

(55) A polynucleotide that is hybridizable with the DNA according to (7) under highly stringent conditions;

(56) A polynucleotide comprising a base sequence complementary to the base sequence of DNA according to (7), or a part thereof;

(57) The polynucleotide according to (56) comprising a base sequence complementary to the base sequence represented by SEQ ID NO: 28 or SEQ ID NO: 29, or a part thereof;

(58) A method of screening a compound or its salt that alters the binding property between the peptide or its salt according to (1) and a protein containing the same or substantially the same amino acid sequence as the amino acid sequence represented by SEQ ID NO: 40, SEQ ID NO: 47, SEQ ID NO: 48 or SEQ ID NO: 49, or a salt thereof, which comprises using the peptide or its salt according to (1) and a protein containing the same or substantially the same amino acid sequence as the amino acid sequence represented by SEQ ID NO: 40, SEQ ID NO: 47, SEQ ID NO: 48 or SEQ ID NO: 49, its partial peptide or a salt thereof;

(59) A kit for screening a compound or its salt that alters the binding property between the peptide or its salt according to (1) and a protein containing the same or substantially the same amino acid sequence as the amino acid sequence represented by SEQ ID NO: 40, SEQ ID NO: 47, SEQ ID NO: 48 or SEQ ID NO: 49, or a salt thereof, comprising the peptide or its salt according to (1) and a protein containing the same or substantially the same amino acid sequence as the amino acid sequence represented by SEQ ID NO: 40, SEQ ID NO: 47, SEQ ID NO: 48 or SEQ ID NO: 49, its partial peptide or a salt thereof;

(60) A compound or its salt that alters the binding property between the peptide or its salt according to (1) and a protein containing the same or substantially the same amino acid sequence as the amino acid sequence represented by SEQ ID NO: 40, SEQ ID NO: 47, SEQ ID NO: 48 or SEQ ID NO: 49, or a salt thereof, which is obtainable using the screening method according to (58) or the screening kit according to (59);

(61) A pharmaceutical comprising the compound or its salt according to (60);

(62) The pharmaceutical according to (61), which is an agent for the prevention/treatment of digestive diseases;

(63) A method of screening a compound or its salt that alters the binding property between a peptide or its salt containing the same or substantially the same amino acid sequence as the amino acid sequence represented by. SEQ ID NO: 34 and a protein containing the same or substantially the same amino acid sequence as the amino acid sequence represented by SEQ ID NO: 1, SEQ ID NO: 36, SEQ ID NO: 40, SEQ ID NO: 47, SEQ ID NO:. 48 or SEQ ID NO: 49, or a salt thereof, which comprises using the peptide or its salt containing the same or substantially the same amino acid sequence as the amino acid sequence represented by SEQ ID NO: 34 and a protein containing the same or substantially the same amino acid sequence as the amino acid sequence represented by SEQ ID NO: 1, SEQ ID NO: 36, SEQ ID NO: 40, SEQ ID NO: 47, SEQ ID NO: 48 or SEQ ID NO: 49, its partial peptide or a salt thereof;

(64) A kit for screening a compound or its salt that alters the binding property between a peptide or its salt containing the same or substantially the same amino acid sequence as the amino acid sequence represented by SEQ ID NO: 34 and a protein containing the same or substantially the same amino acid sequence as the amino acid sequence represented by SEQ ID NO: 1, SEQ ID NO: 36, SEQ ID NO: 40, SEQ ID NO: 47, SEQ ID NO: 48 or SEQ ID NO: 49, or a salt thereof, which comprises using the peptide or its salt containing the same or substantially the same amino acid sequence as the amino acid sequence represented by SEQ ID NO: 34 and a protein containing the same or substantially the same amino acid sequence as the amino acid sequence represented by SEQ ID NO: 1, SEQ ID NO: 36, SEQ ID NO: 40, SEQ ID NO: 47, SEQ ID NO: 48 or SEQ ID NO: 49, its partial peptide or a salt thereof;

(65) A compound or its salt that alters the binding property between a peptide or its salt containing the same or substantially the same amino acid sequence represented by SEQ ID NO: 34 and a protein containing the same or substantially the same amino acid sequence as the amino acid sequence represented by SEQ ID NO: 1, SEQ ID NO: 36, SEQ ID NO: 40, SEQ ID NO: 47, SEQ ID NO: 48 or SEQ ID NO: 49, or a salt thereof, which is obtainable using the screening method according to (63) or the screening kit according to (64);

(66) A pharmaceutical comprising the compound or its salt according to (65);

(67) The pharmaceutical according to (66), which is an agent for the prevention/treatment of digestive diseases; and the like.

BRIEF DESCRIPTION OF THE DRAWINGS

FIG. 1 shows the base sequence of DNA encoding the human brain-derived protein of the invention obtained in EXAMPLE 1 (ZAQC), and the amino acid sequence deduced therefrom (continued to FIG. 2).

FIG. 2 shows the base sequence of DNA encoding the human brain-derived protein of the invention obtained in EXAMPLE 1 (ZAQC), and the amino acid sequence deduced therefrom (continued from FIG. 2 to FIG. 3).

FIG. 3 shows the base sequence of DNA encoding the human brain-derived protein of the invention obtained in EXAMPLE 1 (ZAQC), and the amino acid sequence deduced therefrom (continued from FIG. 2).

FIG. 4 shows the base sequence of DNA encoding the human brain-derived protein of the invention obtained in EXAMPLE 1 (ZAQT), and the amino acid sequence deduced therefrom (continued to FIG. 5).

FIG. 5 shows the base sequence of DNA encoding the human brain-derived protein of the invention obtained in EXAMPLE 1 (ZAQT), and the amino acid sequence deduced therefrom (continued from FIG. 4 to FIG. 6).

FIG. 6 shows the base sequence of DNA encoding the human brain-derived protein of the invention obtained in EXAMPLE 1 (ZAQT), and the amino acid sequence deduced therefrom (continued from FIG. 5).

FIG. 9 shows the amino acid sequences of MIT1, human type ZAQ ligand precursor peptide (A type) and human type ZAQ ligand precursor peptide (G type), wherein "MIT1," "Human (A type)" and "Human (G type)" indicate the amino acid sequences of MIT1, human type ZAQ ligand mature peptide (A type) and human type ZAQ ligand mature peptide (G type), respectively.

BEST MODE FOR CARRYING OUT THE INVENTION

Figure 7:
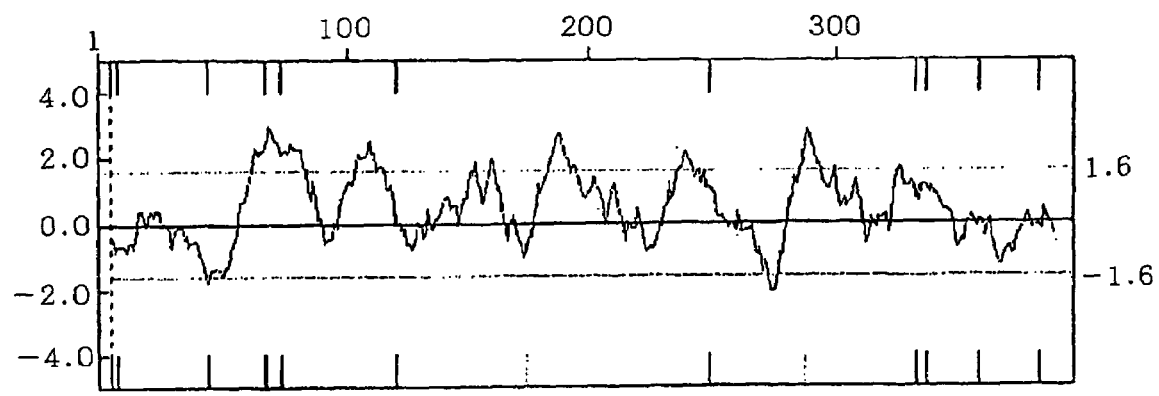
FIG. 7 shows a plot of hydrophobicity for the human brain-derived protein of the invention.

The peptide or its salt of the invention is a peptide or its salt is capable of binding to a protein containing the same or substantially the same amino acid sequence as the amino acid sequence represented by SEQ ID NO: 1, or a salt thereof (hereinafter sometime simply referred to as the protein of the invention), and is a peptide having the ability of binding to the protein of the invention to activate the same, or a salt thereof.

In addition, the peptide or its salt of the invention is a peptide or its salt capable of binding to a protein containing the same or substantially the same amino acid sequence as the amino acid sequence represented by SEQ ID NO: 36, 40, 47, 48 or 49, or a salt thereof, and is a peptide having the ability of binding to the protein of the invention to activate the same, or a salt thereof.

Among them, the peptide or its salt of the invention is preferably a peptide containing the same or substantially the same amino acid sequence as the amino acid sequence represented by SEQ ID NO: 20 or SEQ ID NO: 21 and having the ability of binding to the protein of the invention to activate the same, or a salt thereof.

The capability of the peptide or its salt of the invention binding to the protein of the invention and activating the protein of the invention can be assayed by the method later described.

Hereinafter the peptide or its salt of the invention is sometimes merely referred to as the peptide of the present invention.

The protein of the invention (G protein-coupled receptor protein) is a receptor protein containing the same or substantially the same amino acid sequence as the amino acid sequence (the amino acid sequence in FIGS. 1 to 3 or FIGS. 4 to 6) represented by SEQ ID NO: 1 (hereinafter the protein or its salt of the present invention is sometimes merely referred to as the protein of the invention).

The peptide of the present invention and the protein of the invention may be any peptide or protein derived from any cells of human and other mammals (e.g. guinea pig, rat, mouse, rabbit, swine, sheep, bovine, monkey, etc.) (e.g., spleen cell, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., the corresponding precursor cells, stem cells, cancer cells, etc.) and hemocyte type cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); or any tissues where such cells are present, such as brain or any of brain regions (e.g., olfactory bulb, amygdaloid nucleus, cerebral basal bulb, hippocampus, thalamus, hypothalamus, substhanlamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, pheripheral hemocyte, prostate, testicles, testis, ovary, placenta, uterus, bone, joint, skeletal muscle, etc. (especially, brain and brain region) etc.; the peptide or protein may also be a synthetic peptide or a synthetic protein.

When the peptide of the invention or the protein of the invention has a signal sequence, the peptide or protein can be efficiently secreted extracellularly.

The amino acid sequence which has substantially the same amino acid sequence as that represented by SEQ ID NO: 20 or SEQ ID NO:21 includes an amino acid sequence having at least about 60% homology, (preferably at least about 70% homology, more preferably at least about 80% homology, much more preferably at least about 85%, further much more preferably at least about 90% and most preferably at least about 95%), to the amino acid sequence represented by SEQ ID NO: 20 or SEQ ID NO: 21.

Preferred examples of the peptide having substantially the same amino acid sequence as that represented by SEQ ID NO: 20 or SEQ ID NO: 21 are peptides having substantially the same amino acid sequence as the amino acid sequence represented by SEQ ID NO: 20 or SEQ ID NO: 21 and having substantially equivalent activity to that of the amino acid sequence represented by SEQ ID NO: 20 or SEQ ID NO: 21, etc.

Hereinafter, the peptide containing the amino acid sequence represented by SEQ ID NO: 20 or SEQ ID NO: 21 is sometimes referred to as human type ZAQ ligand mature peptide.

Preferred examples of the peptides, which contain the same or substantially the same amino acid sequence as the amino acid sequence represented by SEQ ID NO: 20 or SEQ ID NO: 21, are peptides containing the same or substantially the same amino acid sequence as the amino acid sequence represented by SEQ ID NO: 20 or SEQ ID NO: 21 and having substantially equivalent activity to that of the amino acid sequence represented by SEQ ID NO: 20 or SEQ ID NO: 21. Particularly preferred are peptides containing the amino acid sequence represented by SEQ ID NO: 20, SEQ ID NO: 21, SEQ ID NO: 22 or SEQ ID NO: 23, and the like.

Hereinafter, the peptide containing the amino acid sequence represented by SEQ ID NO: 22 or SEQ ID NO: 23 is sometimes referred to as human type ZAQ ligand precursor peptide.

The substantially equivalent activity refers to, for example, a binding activity to the protein of the invention, a signal transduction activity mediated by the protein of the invention, an activity of contracting digestive tracts (e.g., intestinal tract), etc. The term substantially equivalent is used to mean that the nature of these activities is equivalent. Therefore, it is preferred that these activities such as a binding activity to the protein of the invention, a signal transduction activity mediated by the protein of the invention, an activity of contracting digestive tracts etc. are equivalent in potency (e.g., about 0.5 to about 2 times), and it is allowable that even differences among grades such as the strength of these activities and molecular weight of the peptide are present.

These activities can be assayed according to publicly known methods, and may also be assayed by, for example, the screening methods which will be later described.

The peptide of the present invention which can be employed includes peptides comprising (i) an amino acid sequence represented by SEQ ID NO: 20 or SEQ ID NO: 21, of which 1 or 2 more (preferably approximately 1 to 30 and more preferably approximately 1 to 20) amino acids are deleted; (ii) an amino acid sequence represented by SEQ ID NO: 20 or SEQ ID NO: 21, to which 1 or 2 more (preferably approximately 1 to 40, more preferably approximately 1 to 30 and most preferably approximately 1 to 20) amino acids are added; (iii) an amino acid sequence represented by NO: 20 or SEQ ID NO: 21, in which 1 or 2 more (preferably approximately 1 to 30 and more preferably approximately 1 to 20) amino acids are substituted by other amino acids; and (iv) a combination of the above amino acid sequences, etc.

The peptide of the invention includes peptides preferably derived from human or other mammals, more preferably derived from human.

Examples of the amino acid sequence which has substantially the same amino acid sequence as the amino acid sequence represented by SEQ ID NO: 1 include an amino acid sequence having at least about 90% homology, preferably at least about 95% homology, and more preferably at least about 98% homology, to the amino acid sequence represented by SEQ ID NO: 1.

Preferred examples of the proteins having substantially the same amino acid sequence as the amino acid sequence represented by SEQ ID NO: 1 are proteins having substantially the same amino acid sequence as the amino acid sequence represented by SEQ ID NO: 1 and having a property substantially equivalent to that of the amino acid sequence represented by SEQ ID NO: 1, etc.

Preferred examples of the protein of the invention, which contains the same or substantially the same amino acid sequence as the amino acid sequence represented by SEQ ID NO: 1 are proteins containing the same or substantially the same amino acid sequence as the amino acid sequence represented by SEQ ID NO: 1 and having an activity substantially equivalent to that of the amino acid sequence represented by SEQ ID NO: 1, etc.

The substantially equivalent activity refers to, for example, a ligand binding activity, a signal transduction activity, etc. The term substantially equivalent is used to mean that the nature of these activities is equivalent. Therefore, it is preferred that these activities such as a ligand binding activity, a signal transduction activity, etc. are equivalent in potency (e.g., about 0.5 to about 2 times), and it is allowable that even differences among grades such as the strength of these activities and molecular weight of the protein are present.

These activities such as a ligand binding activity, a signal transduction activity, etc. can be assayed according to publicly known methods, and may also be assayed by, for example, the assay methods or the screening methods, which will be later described.

Hereinafter, the protein containing the amino acid sequence represented by SEQ ID NO: 1 is sometimes referred to as ZAQ.

The protein of the invention which can be employed includes proteins comprising (i) an amino acid sequence represented by SEQ ID NO: 1, of which 1 or 2 more (preferably approximately 1 to 30, more preferably approximately 1 to 20 and most preferably several (1 or 2)) amino acids are deleted; (ii) an amino acid sequence represented by SEQ ID NO: 1, to which 1 or 2 more (preferably approximately 1 to 30, more preferably approximately 1 to 20 and most preferably several (1 or 2)) amino acids are added; (iii) an amino acid sequence represented by SEQ ID NO: 20 or SEQ ID NO: 21, in which 1 or 2 more (preferably approximately 1 to 30, more preferably approximately 1 to 20 and most preferably several (1 or 2)) amino acids are substituted by other amino acids; and (iv) a combination of the above amino acid sequences, etc.

Examples of the amino acid sequence which has substantially the same amino acid sequence as the amino acid sequence represented by SEQ ID NO: 36 include an amino acid sequence having at least about 90% homology, preferably at least about 95% homology, and more preferably at least about 98% homology, to the amino acid sequence represented by SEQ ID NO: 36.

Preferred examples of the proteins containing substantially the same amino acid sequence as the amino acid sequence represented by SEQ ID NO: 36 include proteins having substantially the same amino acid sequence as the amino acid sequence represented by SEQ ID NO: 36 and having a property substantially equivalent to that of the amino acid sequence represented by SEQ ID NO: 36, etc.

Preferred examples of the protein containing the same or substantially the same amino acid sequence as the amino acid sequence represented by SEQ ID NO: 36 include proteins containing the same or substantially the same amino acid sequence as the amino acid sequence represented by SEQ ID NO: 36 and having an activity substantially equivalent to that of the amino acid sequence represented by SEQ ID NO: 36, etc., in particular, proteins described in WO 98/46620, etc.

Examples of the amino acid sequence which has substantially the same amino acid sequence as the amino acid sequence represented by SEQ ID NO: 40 include an amino acid sequence having at least about 97% homology, preferably at least about 98% homology, more preferably at least about 99% homology, and most preferably at least about 99.5% homology, to the amino acid sequence represented by SEQ ID NO: 40, etc.

Preferred examples of the proteins containing substantially the same amino acid sequence as the amino acid sequence represented by SEQ ID NO: 40 are proteins containing substantially the same amino acid sequence as the amino acid sequence represented by SEQ ID NO: 40 and having a property substantially equivalent to that of the amino acid sequence represented by SEQ ID NO: 40, etc.

Preferred examples of the protein containing the same or substantially the same amino acid sequence as the amino acid sequence represented by SEQ ID NO: 40 include proteins containing the same or substantially the same amino acid sequence as the amino acid sequence represented by SEQ ID NO: 40 and having an activity substantially equivalent to that of the amino acid sequence represented by SEQ ID NO: 40, etc.

Examples of the amino acid sequence which has substantially the same amino acid sequence as the amino acid sequence represented by SEQ ID NO: 47 include an amino acid sequence having at least about 95% homology, preferably at least about 96% homology, and more preferably at least about 97% homology, and most preferably at least about 98% homology, to the amino acid sequence represented by SEQ ID NO: 47, etc.

Preferred examples of the proteins containing substantially the same amino acid sequence as the amino acid sequence represented by SEQ ID NO: 47 are proteins containing substantially the same amino acid sequence as the amino acid sequence represented by SEQ ID NO: 47 and having a property substantially equivalent to that of the amino acid sequence represented by SEQ ID NO: 47, etc.

Preferred examples of the protein containing the same or substantially the same amino acid sequence as the amino acid sequence represented by SEQ ID NO: 47 are proteins containing the same or substantially the same amino acid sequence as the amino acid sequence represented by SEQ ID NO: 47 and having an activity substantially equivalent to that of the amino acid sequence represented by SEQ ID NO: 47, etc.

Examples of the amino acid sequence which has substantially the same amino acid sequence as the amino acid sequence represented by SEQ ID NO: 48 include an amino acid sequence having at least about 95% homology, preferably at least about 96% homology, and more preferably at least about 97% homology, and most preferably at least about 98% homology, to the amino acid sequence represented by SEQ ID NO: 48, etc.

Preferred examples of the proteins containing substantially the same amino acid sequence as the amino acid sequence represented by SEQ ID NO: 48 are proteins containing substantially the same amino acid sequence as the amino acid sequence represented by SEQ ID NO: 48 and having a property substantially equivalent to that of the amino acid sequence represented by SEQ ID NO: 48, etc.

Preferred examples of the protein containing the same or substantially the same amino acid sequence as the amino acid sequence represented by SEQ ID NO: 48 are proteins containing the same or substantially the same amino acid sequence as the amino acid sequence represented by SEQ ID NO: 48 and having an activity substantially equivalent to that of the amino acid sequence represented by SEQ ID NO: 48, etc.; particularly preferred are proteins described in Biochem. Biophys. Acta, 1491, 369–375, 2000, etc.

Examples of the amino acid sequence which has substantially the same amino acid sequence as the amino acid sequence represented by SEQ ID NO: 49 include an amino acid sequence having at least about 95% homology, preferably at least about 96% homology, and more preferably at least about 97% homology, and most preferably at least about 98% homology, to the amino acid sequence represented by SEQ ID NO: 49.

Preferred examples of the proteins containing substantially the same amino acid sequence as the amino acid sequence represented by SEQ ID NO: 49 are proteins containing substantially the same amino acid sequence as the amino acid sequence represented by SEQ ID NO: 49 and having a property substantially equivalent to that of the amino acid sequence represented by SEQ ID NO: 49, etc.

Preferred examples of the protein containing the same or substantially the same amino acid sequence as the amino acid sequence represented by SEQ ID NO: 49 are proteins containing the same or substantially the same amino acid sequence as the amino acid sequence represented by SEQ ID NO: 49 and having an activity substantially equivalent to that of the amino acid sequence represented by SEQ ID NO: 49, etc.; particularly preferred are proteins described in WO 98/46620, etc.

The substantially equivalent activity refers to, for example, a ligand binding activity, a signal transduction activity, etc. The term substantially equivalent is used to mean that the nature of these activities is equivalent. Therefore, it is preferred that these activities such as a ligand binding activity, a signal transduction activity, etc. are equivalent in potency (e.g., about 0.5 to about 2 times), and it is allowable that even differences among grades such as the strength of these activities and molecular weight of the protein are present.

The activities such as a ligand binding activity, a signal transduction activity, etc. can be assayed according to publicly known methods.

Examples of the amino acid sequence which has substantially the same amino acid sequence as the amino acid sequence represented by SEQ ID NO: 34 include an amino acid sequence having at least about 60% homology, preferably at least about 70% homology, more preferably at least about 80% homology, and most preferably at least about 90% homology, to the amino acid sequence represented by SEQ ID NO: 34, etc.

Preferred examples of the peptide containing the same or substantially the same amino acid sequence as the amino acid sequence represented by SEQ ID NO: 34 are peptide containing the same or substantially the same amino acid sequence as the amino acid sequence represented by SEQ ID NO: 34 and having an activity substantially equivalent (e.g., a contractile activity in ileum, a contractile activity in distal colon, a relaxation activity in proximal colon, etc.) to that of the amino acid sequence represented by SEQ ID NO: 34, etc.; in particular, MIT1, which will be later described, and so on.

Throughout the present specification, the peptides and proteins are represented in accordance with the conventional way of describing peptides, that is, the N-terminus (amino terminus) at the left hand and the C-terminus (carboxyl terminus) at the right hand. In the proteins of the present invention including the proteins containing the amino acid sequence shown by SEQ ID NO: 1, the C-terminus may be any of a carboxyl group (—COOH), a carboxylate (—COO⁻), an amide (—CONH$_2$) and an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; an $C_{7-14}$ aralkyl group such as a phenyl-$C_{1-2}$ alkyl group, e.g., benzyl, phenethyl, etc.; a α-naphthyl-$C_{1-2}$ alkyl group such as α-naphthylmethyl, etc.; and the like. In addition, pivaloyloxymethyl or the like, which is used widely as an ester for oral administration, may also be used.

Where the peptide/protein of the invention contains a carboxyl group (or a carboxylate) at a position other than the C-terminus, it may be amidated or esterified and such an amide or ester is also included within the peptide/protein of the invention. The ester group may be the same group as that described with respect to the above C-terminal ester.

Furthermore, examples of the peptide/protein of the invention include variants of the above peptide/protein, wherein the amino group at the N-terminus (e.g., methionine residue) of the peptide is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated peptides/conjugated proteins such as glycopeptides/glycoproteins having sugar chains.

Specific examples of the peptide of the invention include human-derived (more preferably human brain-derived) peptides containing the amino acid sequence represented by SEQ ID NO: 20, human-derived (more preferably human brain-derived) peptides containing the amino acid sequence represented by SEQ ID NO: 21, etc. More preferably, there are human-derived peptides containing the amino acid sequence represented by SEQ ID NO: 21.

Specific examples of the protein of the invention include human-derived (preferably human brain-derived) proteins containing the amino acid sequence represented by SEQ ID NO: 1, etc.

Any partial peptide described for the protein of the invention can be used as the partial peptide of the protein of the invention (hereinafter sometimes merely referred to as the partial peptide of the invention). For example, a part of the protein molecule of the present invention, which is exposed to the outside of a cell membrane or the like, can be used so long as it has a substantially equivalent receptor binding activity.

Specifically, the partial peptide of the protein containing the amino acid sequence represented by SEQ ID NO: 1 is a peptide containing the parts, which have been analyzed to be extracellular domains (hydrophilic domains) in the hydrophobic plotting analysis as shown FIG. 7. A peptide containing a hydrophobic domain part can be used as well. In addition, the peptide containing each domain separately may be used but the peptide may contain plural domains together.

The number of amino acids in the partial peptide of the invention is at least 20, preferably at least 50 and more preferably at least 100 amino acids in the amino acid sequence, which constitutes the protein of the invention described above, and peptides having the amino acid sequence of such numbers of amino acids, etc. are preferred.

Substantially the same amino acid sequence includes an amino acid sequence having at least about 50% homology, preferably at least about 70% homology, more preferably at least about 80% homology, much more preferably at least about 90% homology and most preferably at least about 95% homology, to these amino acid sequences.

Herein, the term "substantially equivalent ligand binding activity" is used in the same significance as defined above. The "substantially equivalent ligand binding activity" can be assayed by a modification of publicly known methods.

In the partial peptide of the invention, at least 1 or 2 more (preferably approximately 1 to 10, more preferably several (1 or 2)) amino acids may be deleted; at least 1 or 2 more (preferably approximately 1 to 20, more preferably approximately 1 to 10 and most preferably several (1 or 2)) amino acids may be added; or at least 1 or 2 more (preferably approximately 1 to 10, more preferably approximately 1 to 5, and most preferably several (1 or 2)), amino acids may be substituted by other amino acids.

In the partial peptide of the invention, the C-terminus may be any of a carboxyl group (—COOH), a carboxylate (—COO⁻), an amide (—CONH$_2$) and an ester (—COOR). When the partial peptide of the invention has a carboxyl group (or carboxylate) at the position other than the C-terminus, the partial peptide wherein the carboxyl group is amidated or esterified is also included in the partial peptide of the invention. As such an ester, for example, the C-terminal esters described above, etc. are employed.

In addition, examples of the partial peptide of the invention further include peptide derivatives, as in the protein of the invention described above, wherein the amino group at the N-terminal methionine residue is protected with a protecting group, those wherein the N-terminal region is cleaved in vivo and the Gln formed is pyroglutaminated, those wherein a substituent on the side chain of an amino acid in the molecule is protected with a suitable protecting group, or conjugated peptides such as glycopeptides having sugar chains.

The partial peptide of the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49 may be any partial peptide, so long as it is the aforesaid partial peptide of the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, and in the protein molecules, e.g., those having a site extended outside the cell membrane and having substantially equivalent ligand binding activity are employed. The number of amino acids in the partial peptide is at least 20, preferably at least 50 and more preferably at least 100 amino acids in the amino acid sequence, which constitutes the protein described above, and peptides having the amino acid sequence of such numbers of amino acids, etc. are preferred. Substantially the same amino acid sequence includes an amino acid sequence having at least about 50% homology, preferably at least about 70% homology, more preferably at least about 80% homology, much more preferably at least about 90% homology and most preferably at least about 95% homology, to these amino acid sequences.

As the salts of the peptide of the invention and the protein of the invention or its partial peptide, etc., physiologically acceptable acid addition salts are particularly preferred. Examples of such salts are salts with inorganic acids (e.g., hydrochloric acid, phosphoric acid, hydrobromic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The peptide or protein of the invention or salts thereof as well as the proteins containing the amino acid sequence represented by SEQ ID NO: 36, SEQ ID NO: 40, SEQ ID NO: 47 or salts thereof may be manufactured by a publicly known method used to purify a peptide/protein from human or other mammalian cells or tissues described above. Alternatively, they can also be manufactured by culturing a transformant bearing a DNA encoding the peptide of the invention, the protein of the invention, or the protein containing the amino acid sequence represented by SEQ ID NO: 36, SEQ ID NO: 40, SEQ ID NO: 47, as will be later described. Also, they can be manufactured by the peptide/protein synthesis later described or by a modification thereof. Furthermore, the protein containing the amino acid sequence represented by SEQ ID NO: 48 or salts thereof may be manufactured by a modification of the method described in Biochem. Biophys. Acta, 1491, 369–375, 2000. The protein containing the amino acid sequence represented by SEQ ID NO: 49 or salts thereof may be manufactured by a modification of the method described in WO 98/46620.

Where the peptides/proteins or salts thereof are manufactured from human or mammalian tissues or cells, human or mammalian tissues or cells are homogenized and extracted with an acid or the like, and the extract is isolated and purified by a combination of chromatographic techniques such as reversed phase chromatography, ion exchange chromatography, and the like.

To synthesize the peptide of the invention, the protein of the invention, its partial peptide or its amides, or salts thereof, commercially available resins that are used for peptide/protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective peptide/protein according to various condensation methods publicly known in the art. At the end of the reaction, the peptide/protein is excised from the resin and at the same time, the protecting groups are removed. Then, intramolecular disulfide bond-forming reaction is performed in a highly diluted solution to obtain the objective peptide/protein or amides thereof.

For condensation of the protected amino acids described above, a variety of activation reagents for peptide/protein synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for peptide/protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, Cl$_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetate, or a mixture solution of these acids; a treatment with a base such as diisopropylethylamine, triethylamine, piperidine or piperazine; and reduction with sodium in liquid ammonia. The elimination by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group used as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution, dilute ammonia, etc.

Protection of functional groups that should not be involved in the reaction of the starting materials, elimination of the protecting groups and activation of functional groups involved in the reaction may be appropriately selected from publicly known groups and publicly known means.

In another method for obtaining the amides of the peptide/protein, for example, the α-carboxyl group of the carboxyl terminal amino acid is first protected by amidation; the peptide chain is then extended from the amino group side to a desired length. Thereafter, a peptide/protein in which only the protecting group of the N-terminal α-amino group has been eliminated from the peptide chain and a peptide/protein in which only the protecting group of the C-terminal carboxyl group has been eliminated are manufactured. The two peptides/two proteins are condensed in a mixture of the solvents described above. The details of the condensation reaction are the same as described above. After the protected peptide/protected protein obtained by the condensation is purified, all the protecting groups are eliminated by the method described above to give the desired crude peptide/crude protein. This crude peptide/crude protein is purified by various known purification means. Lyophilization of the major fraction gives the amide of the desired peptide/protein.

To prepare the esterified peptide/protein, for example, the α-carboxyl group of the carboxyl terminal amino acid is condensed with a desired alcohol to prepare the amino acid ester, which is followed by procedure similar to the preparation of the amidated protein above to give the desired esterified peptide/protein.

The peptide of the invention can be manufactured in accordance with publicly known peptide synthesis.

The partial peptide of the protein of the invention or salts thereof can be manufactured by publicly known methods for peptide synthesis, or by cleaving the protein of the invention with an appropriate peptidase.

For the methods for peptide synthesis, for example, either solid phase synthesis or liquid phase synthesis may be used. That is, the partial peptide or amino acids that can constitute the peptide of the invention or the protein of the invention are condensed with the remaining part. Where the product comprises protecting groups, these protecting groups are removed to give the desired peptide. Publicly known methods for condensation and elimination of the protecting groups are described in (1)–(5) below.

(1) M. Bodanszky & M. A. Ondetti: Peptide Synthesis, Interscience Publishers, New York (1966)

(2) Schroeder & Luebke: The Peptide, Academic Press, New York (1965)

(3) Nobuo Izumiya, et al.: *Peptide Gosei-no-Kiso to Jikken* (Basics and experiments of peptide synthesis), published by Maruzen Co. (1975)

(4) Haruaki Yajima & Shunpei Sakakibara: Seikagaku Jikken Koza (Biochemical Experiment) 1, *Tanpakushitsu no Kagaku* (Chemistry of Proteins) IV, 205 (1977)

(5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the peptide or the partial peptide of the invention. When the peptide or the partial peptide obtained by the above methods is in a free form, the peptide can be converted into an appropriate salt by a publicly known method; when the protein is obtained in a salt form, it can be converted into a free form by a publicly known method.

The DNA encoding the peptide/protein of the invention may be any DNA so long as it comprises the base sequence encoding the peptide/protein of the invention described above. Such a DNA may also be any one of genomic DNA, genomic DNA library, cDNA derived from the cells or tissues described above, cDNA library derived from the cells or tissues described above and synthetic DNA. The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or MRNA fraction prepared from the above-described cells or tissues.

Specifically, the DNA encoding the peptide of the invention may be any one of, for example, DNA having the base sequence represented by SEQ ID NO: 26 or SEQ ID NO: 27, or any DNA having a base sequence hybridizable to the base sequence represented by SEQ ID NO: 26 or SEQ ID NO: 27vunder high stringent conditions and encoding a peptide which has an activity substantially equivalent to that of the peptide of the invention (e.g., a binding activity to the protein of the invention, a signal transduction activity, a contractile activity in digestive tracts (e.g., intestinal tract), etc.).

The DNA containing the base sequence represented by SEQ ID NO: 26 includes a DNA containing the base sequence represented by SEQ ID NO: 28, etc.

Examples of the DNA that is hybridizable to the DNA containing the base sequence represented by SEQ ID NO: 26 under high stringent conditions include 10 DNAs having at least about 60% homology, preferably at least about 70% homology and more preferably at least about 80% homology, to the DNA containing the base sequence represented by SEQ ID NO: 26, etc.

The DNA containing the base sequence represented by SEQ ID NO: 27 includes a DNA containing the base sequence represented by SEQ ID NO: 29, etc.

Examples of the DNA that is hybridizable to the DNA containing the base sequence represented by SEQ ID NO: 27 under high stringent conditions include DNAs having at least about 60% homology, preferably at least about 70% homology and more preferably at least about 80% homology, to the DNA containing the base sequence represented by SEQ ID NO: 27, etc.

Also, the DNA encoding the protein of the invention may be any one of, for example, a DNA comprising a base sequence represented by SEQ ID NO: 2 or SEQ ID NO: 3, and a DNA containing a DNA that is hybridizable to a DNA containing the base sequence represented by SEQ ID NO: 2 or SEQ ID NO: 3 under highly stringent conditions and encoding a protein which has an activity (e.g., a ligand biding activity, a signal transduction activity, etc.) substantially equivalent to that of the protein of the invention.

Examples of the DNA that is hybridizable to a DNA containing the base sequence represented by SEQ ID NO: 2 or SEQ ID NO: 3 under high stringent conditions include DNAs having at least about 90% homology, preferably at least about 95% homology and more preferably at least about 98% homology, to the base sequence represented by SEQ ID NO: 2 or SEQ ID NO: 3, etc.

The hybridization can be carried out by publicly known methods or by modifications thereof, for example, in accordance with the method described in Molecular Cloning, 2nd. (J. Sambrook et al., Cold Spring Harbor Lab. Press, 1989), etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically, for the DNA encoding the peptide containing the amino acid sequence represented by SEQ ID NO:20, there is a DNA containing the base sequence represented by SEQ ID NO: 26; for the DNA encoding the peptide containing the amino acid sequence represented by SEQ ID NO:21, there is a DNA containing the base sequence represented by SEQ ID NO: 27; for the DNA encoding the peptide containing the amino acid sequence represented by SEQ ID NO:22, there is a DNA containing the base sequence represented by SEQ ID NO: 28; and for the DNA encoding the peptide containing the amino acid sequence represented by SEQ ID NO:23, there is a DNA containing the base sequence represented by SEQ ID NO: 29.

For the DNA encoding the protein containing the amino acid sequence represented by SEQ ID NO: 1, there is a DNA containing the base sequence represented by SEQ ID NO: 2 or SEQ ID NO: 3.

The nucleotides (oligonucleotide) comprising the base sequence or a part of the base sequence complementary to the DNA encoding the peptide of the invention is used to mean that not only the DNA encoding the peptide of the invention but also RNA are included.

According to the present invention, antisense (oligo) nucleotides (nucleic acid) that are capable of inhibiting the replication or expression of the gene for the peptide of the invention can be designed and synthesized based on the cloned or determined base sequence information of the DNA encoding the peptide. Such an (oligo) nucleotide (nucleic acid) is hybridizable to RNA of the gene for the peptide of the invention thereby to inhibit the synthesis or function of said RNA, or is capable of modulating or controlling the gene expression of the peptide of the invention via interaction with RNA associated with the peptide of the invention. (Oligo)nucleotides complementary to the selected sequences of RNA associated with the peptide of the invention and (oligo) nucleotides specifically hybridizable with the RNA associated with the peptide of the invention are useful in modulating or controlling the gene expression of the peptide of the invention in vivo and in vitro, and useful for the treatment or diagnosis of disease, etc.

The term "corresponding" is used to mean homologous to or complementary to a particular sequence of the nucleotide or base sequence or nucleic acid including gene. The term "corresponding" between nucleotides, base sequences or nucleic acids and peptides normally refers to amino acids of a peptide under instructions derived from the sequence of nucleotides (nucleic acids) or their complements. The 5' end hairpin loop, the 5' end 6-base-pair repeats, the 5' end untranslated region, the polypeptide translation initiation codon, the protein coding region, the ORF translation initiation codon, the 3' untranslated region, the 3' end palindrome region, and the 3' end hairpin loop may be selected as preferred target regions, though any other region may also be selected as a target in genes of the peptide of the invention.

The relationship between the targeted nucleic acids and the (oligo) nucleotides complementary to at least a part of the target, specifically the relationship between the target and the (oligo) nucleotides hybridizable to the target, can be denoted to be "antisense". Examples of the antisense (oligo) nucleotides include polydeoxynucleotides bearing 2-deoxy-D-ribose, polydeoxynucleotides bearing D-ribose, any other type of polynucleotides which are N-glycosides of a purine or pyrimidine base, or other polymers comprising non-nucleotide backbones (e.g., protein nucleic acids and synthetic sequence-specific nucleic acid polymers commercially available) or other polymers bearing nonstandard linkages (provided that the polymers contain nucleotides having such a configuration that allows base pairing or base stacking, as can be found in DNA or RNA), etc. The antisense polynucleotides may be double-stranded DNA, single-stranded DNA, double-stranded RNA, single-stranded RNA or a DNA:RNA hybrid, and may further include unmodified polynucleotides or unmodified oligo-nucleotides, those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-comprising linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those comprising chelators (e.g., metals, radioactive metals, boron, oxidative metals, etc.), those comprising alkylating agents, those with modified linkages (e.g., α anomeric nucleic acids, etc.), and the like. Herein, the terms "nucleoside", "nucleotide" and "nucleic acid" are used to mean moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense nucleic acid of the present invention is RNA, DNA or a modified nucleic acid. Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may comprise altered or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be supplied with the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the protein in vivo and in vitro. The nucleic acid can be applied to cells by a variety of publicly known methods.

The DNA encoding the partial peptide of the invention may be any DNA so long as it contains the base sequence encoding the partial peptide of the invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using MRNA fraction prepared from the cells and tissues described above.

Specifically, the DNA encoding the partial peptide of the invention may be any one of, for example, a DNA containing a partial base sequence of the DNA having the base sequence represented by SEQ ID NO: 2 or SEQ ID NO: 3, or (2) a DNA containing a partial base sequence of the DNA having a base sequence hybridizable to the base sequence represented by SEQ ID NO: 2 or SEQ ID NO: 3 under highly stringent conditions and encoding a protein which has an activity (e.g., a ligand biding activity, a signal transduction activity, etc.) substantially equivalent to that of the protein peptide of the invention.

Examples of the DNA that is hybridizable to a DNA containing the base sequence represented by SEQ ID NO: 2 or SEQ ID NO: 3 under highly stringent conditions include DNAs containing a base sequence having at least about 90% homology, preferably at least about 95% homology and more preferably at least about 98% homology, to the base sequence represented by SEQ ID NO: 2 or SEQ ID NO: 3, etc.

For cloning of the DNA that completely encodes the peptide of the invention, the DNA can be amplified by PCR using synthetic DNA primers containing a part of the base sequence of a DNA encoding the peptide of the invention, or the DNA inserted into an appropriate vector can be selected by hybridization with a labeled DNA fragment or synthetic DNA, which encodes a part or entire region of the peptide of the invention. The hybridization can be carried out, for example, according to the method described in Molecular Cloning, 2nd, (J. Sambrook et al., Cold Spring Harbor Lab. Press, 1989). The hybridization may also be performed using commercially available library in accordance with the protocol described in the attached instructions.

Cloning of the DNA that completely encodes the protein of the invention or its partial peptide (hereinafter merely referred to as the protein of the invention) can be performed in a manner similar to the cloning of the DNA that completely encodes the peptide of the invention.

Conversion of the base sequence of the DNA can be effected by publicly known methods such as the ODA-LA. PCR, the Gapped duplex method or the Kunkel method, etc., or modifications thereof, by PCR or using publicly known kits available as Mutan™-supper Express Km (manufactured by Takara Shuzo Co., Ltd.), Mutan™-K (manufactured by Takara Shuzo Co., Ltd.), or the like.

The cloned DNA encoding the peptide/protein can be used as it is, depending upon purpose or, if desired, after digestion with a restriction enzyme or after addition of a linker thereto. The DNA may bear ATG as a translation initiation codon at the 5' end thereof and may further bear TAA, TGA or TAG as a translation termination codon at the 3' end thereof. These translation initiation and termination codons may also be added by using an appropriate synthetic DNA adapter.

The expression vector for the peptide/protein of the invention can be manufactured, for example, by (a) excising the desired DNA fragment from the DNA encoding the peptide/protein of the invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λphage, etc., animal viruses such as retrovirus, vaccinia virus, baculovirus, etc. as well as pA1-11, pXT1, pRc/CMV, pRc/RSV, pcDNAI/Neo, pcDNA3.1, pRc/CMV2, pRc/RSV (Invitrogen), etc.

The promoter used in the present invention may be any promoter if it matches well with a host to be used for gene expression. In the case of using animal cells as the host, examples of the promoter include SRα promoter, SV40 promoter, HIV-LTR promoter, CMV promoter, HSV-TK promoter, etc.

Among them, CMV promoter or SRα promoter is preferably used. Where the host is bacteria of the genus *Escherichia*, preferred examples of the promoter include trp promoter, lac promoter, recA promoter, $\lambda P_L$ promoter, lpp promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally comprise an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in CHO (dhfr⁻) cells, selection can also be made on thymidine free media.

If necessary, a signal sequence that matches with a host is added to the N-terminus of the protein of the invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the peptide/protein of the invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)), C600 (Genetics, 39, 440 (1954)], etc.

Examples of the bacteria belonging to the genus *Bacillus* include *Bacillus subtilis* MI114 [Gene, 24, 255 (1983)), 207–21 (Journal of Biochemistry, 95, 87 (1984)], etc.

Examples of yeast include *Saccharomyces cerevisiae* AH22, AH22R⁻, NA87-11A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213–217 (1977), etc.

As the insect, for example, a larva of *Bombyx mori*, etc. can be used [Maeda, et al., Nature, 315, 592 (1985)].

Examples of animal cells include monkey cells COS-7, Vero, Chinese hamster cells CHO (hereinafter referred to as CHO cells), dhfr gene deficient Chinese hamster cells CHO (hereinafter simply referred to as CHO(dhfr⁻) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972) or Gene, 17, 107 (1982), etc.

Bacteria belonging to the genus *Bacillus* can be transformed, for example, by the method described in Molecular & General Genetics, 168 111 (1979), etc.

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263–267 (1995), (published by Shujunsha), or Virology, 52, 456 (1973).

Thus, the transformant transformed with the expression vector comprising the DNA encoding the G protein-coupled receptor protein can be obtained.

Where the host is bacteria belonging to the genus *Escherichia* or the genus *Bacillus*, the transformant can be appropriately incubated in a liquid medium which comprises materials required for growth of the transformant such as carbon sources, nitrogen sources, inorganic materials and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary, the culture may be aerated or agitated.

Where the bacteria belonging to the genus *Bacillus* are used as the host, the transformant is cultivated generally at about 30° C. to about 40° C. for about 6 hours to about 24 hours. If necessary, the culture can be aerated or agitated.

Where yeast is used as the host, the transformant is cultivated, for example, in Burkholder's minimal medium [Bostian, K. L. et al., (Proc. Natl. Acad. Sci. U.S.A.,) 77, 4505 (1980)] or in SD medium supplemented with 0.5% Casamino acids [Bitter, G. A. et al., (Proc. Natl. Acad. Sci. U.S.A.,) 81, 5330 (1984)]. Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium comprising about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the peptide/protein of the invention can be produced in the cell, cell membrane or the outside of the transformant, etc.

The peptide/protein of the invention can be separated and purified from the culture described above by the following procedures.

When the peptide/protein of the invention is extracted from the culture or cells, after cultivation the transformants or cells are collected by a publicly known method and suspended in an appropriate buffer. The transformants or cells are then disrupted by publicly known methods such as ultrasonication, a treatment with lysozyme and/or freeze-thaw cycling, followed by centrifugation, filtration, etc. Thus, the crude extract of the protein can be obtained. The buffer used for the procedures may comprise a protein modifier such as urea or guanidine hydrochloride, or a surfactant such as Triton X-100™, etc. When the peptide/protein is secreted in the culture, after completion of the cultivation the supernatant can be separated from the transformants or cells to collect the supernatant by a publicly known method.

The peptide/protein comprised in the culture supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the peptide/protein thus obtained is in a free form, it can be converted into the salt by publicly known methods or modifications thereof. On the other hand, when the protein is obtained in the form of a salt, it can be converted into the free form or in the form of a different salt by publicly known methods or modifications thereof.

The peptide/protein produced by the recombinant can be treated, prior to or after the purification, with an appropriate protein modifying enzyme so that the protein can be appropriately modified or partially removed. Examples of the protein modifying enzyme include trypsin, chymotrypsin, arginyl endopeptidase, protein kinase, glycosidase or the like.

The activity of the thus produced peptide of the invention can be determined by a binding test to a labeled form of the peptide of the invention and the protein of the invention, by an enzyme immunoassay, using a specific antibody, or the like.

The activity of the produced protein of the invention can be determined by the binding test to a labeled form of the peptide of the invention, by an enzyme immunoassay using a specific antibody, or the like.

Antibodies to the peptide of the invention, the protein of the invention, its partial peptides, or salts thereof may be any of polyclonal antibodies and monoclonal antibodies, as long as they are capable of recognizing the peptide of the invention, the protein of the invention, its partial peptides, or salts thereof.

The antibodies to the peptide of the invention, the protein of the invention, its partial peptides, or salts thereof (hereinafter sometimes merely referred to as the peptide/protein, etc. of the invention) may be manufactured by publicly known methods for manufacturing antibodies or antisera, using as antigens the peptide/protein, etc. of the invention.

[Preparation of Monoclonal Antibody]

(a) Preparation of Monoclonal Antibody-producing Cells

The peptide/protein, etc. of the invention is administered to mammalians either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable mammalians are monkeys, rabbits, dogs, guinea pigs, mice, rats, sheep and goats, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells comprised therein are fused with myeloma cells to give monoclonal antibody-producing hybridomas. Measurement of the antibody titer in antisera may be carried out, for example, by reacting a labeled peptide/protein, etc. of the invention, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to 40° C., preferably at 30 to 37° C. for about 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the peptide/protein, etc. of the invention as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the peptide/protein, etc. of the invention labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium comprising 1% to 20%, preferably 10% to 20% fetal bovine serum, GIT medium (Wako Pure Chemical Industries, Ltd.) comprising -1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by conventional methods as separation and purification methods of polyclonal antibody, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Preparation of Polyclonal Antibody]

The polyclonal antibody of the present invention can be manufactured by publicly known methods or modifications thereof. For example, mammal is immunized with an immunogen (the peptide/protein, etc. of the invention as an antigen) per se, or a complex of immunogen and a carrier protein is formed and a warm-blooded animal is immunized with the complex in a manner similar to the method described above for the manufacture of monoclonal antibodies. The product comprising the antibody to the peptide/protein, etc. of the invention is collected from the immunized animal followed by separation and purification of the antibody.

In the complex of immunogen and carrier protein used to immunize a mammal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or keyhole limpet hemocyanin, etc. is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents comprising thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every 2 to 6 weeks and 3 to 10 times in total.

The polyclonal antibody can be collected from the blood, ascites, etc., preferably from the blood of mammalian animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The peptide of the invention, the DNA encoding the peptide of the invention (hereinafter sometimes merely referred to as the DNA of the invention) and the antibody to the peptide of the invention (hereinafter sometimes merely referred to as the antibody of the invention) are useful for implementing (1) agents for the prevention/treatment of various diseases associated with the protein of the invention; (2) screening a compound or its salt that alters the binding property of the peptide of the invention to the protein of the invention; (3) quantification of the peptide of the invention or its salt; (4) gene diagnosis; (5) drugs comprising the antisense DNA; (6) drugs comprising the antibody of the invention; (7) preparing non-human animals bearing the DNA of the invention; (8) drug design based on comparison between ligands and receptors that are structurally analogous, etc.

In particular, by the use of the receptor binding assay system using the expression system of the recombinant protein of the invention, compounds (e.g., ZAQ agonists, ZAQ antagonists, etc.) that alter the binding property of human- or mammal-specific ligands to the protein of the invention can be screened, and the agonists or antagonists can be used as agents for the prevention/treatment, etc. of various diseases.

The peptide of the invention, the DNA of the present invention and the antibody of the invention are specifically described below, with respect to their applications.

(1) Therapeutic/preventive Agent for Diseases with which the Peptide of the Invention is Associated As will be described hereinafter, it has become clear that the peptide of the invention is a ligand to the protein of the invention (G protein-coupled receptor), since the peptide of the invention is present as a humoral factor in vivo and activates the protein of the invention to elevate the intracellular $Ca^{2+}$ ion concentration in the cell in which the protein of the invention has been expressed.

Also, the peptide of the invention is recognized to have about 56% homology to snake venom Mamba Intestinal Toxin 1 (sometimes abbreviated as MIT1; SEQ ID NO: 34; Toxicon, 28, 847–856, 1990; FEBS Letters, 461, 183–188, 1999) on an amino acid level.

It was reported that MIT1 induced contraction in ileum or distal large intestine, or relaxation in proximal large intestine and its degree was as potent as comparable to 40 mM potassium chloride (FEBS Letters, 461, 183–188, 1999). However, the site or mechanism of its action was not resolved. The present inventors clarified that the action of MIT1 was mediated by the protein of the invention as well.

In view of the foregoing, the peptide of the invention has an activity of inducing the contraction or relaxation of the entire intestinal tracts to control the intestinal tract motility (digestive activity), etc. (e.g., EXAMPLE 11 later described). Thus, when the DNA, etc. of the invention is lacking or when its expression level is abnormally reduced, various diseases such as digestive diseases (e.g., enteritis, constipation, malabsorption syndrome, etc.) are developed.

Accordingly, the peptide of the invention or the DNA of the invention can be used as drugs for the treatment or prevention, etc. of various diseases including digestive diseases (e.g., enteritis, constipation, malabsorption syndrome, etc.) or the like.

When a patient has a reduced level of, or deficient in the peptide of the invention in his or her body so that signal transduction is not fully or normally exerted in the cell wherein the protein of the invention has been expressed, the peptide of the invention can provide its role sufficiently or properly for the patient, (a) by administering the DNA of the present invention to the patient to express the peptide of the invention in the body, (b) by inserting the DNA of the present invention into a cell, expressing the peptide of the invention and then transplanting the cell to the patient, or (c) by administering the peptide of the invention to the patient, or the like.

When the DNA of the present invention is used as the preventive/therapeutic agents described above, the DNA itself is administered to human or other warm-blooded animal; or the DNA is inserted into an appropriate vector such as retrovirus vector, adenovirus vector, adenovirus-associated virus vector, etc. and then administered to human or other warm-blooded animal in a conventional manner. The DNA of the present invention may also be administered as an intact DNA; or the DNA may be prepared into a pharmaceutical composition with physiologically acceptable carriers such as adjuvants, etc. to accelerate its uptake and the composition may be administered by gene gun or through a catheter such as a catheter with a hydrogel.

When the peptide of the invention is used as the aforesaid therapeutic/preventive agents, the peptide is advantageously used on a purity level of at least 90%, preferably at least 95%, more preferably at least 98% and most preferably at least 99%.

The peptide of the invention can be used orally, for example, in the form of tablets which may be sugar coated if necessary, capsules, elixirs, macrocapsules etc., or parenterally in the form of injectable preparations such as a sterile solution and a suspension in water or with other pharmaceutically acceptable liquid. These preparations can be manufactured by mixing the peptide of the invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™, HCO-50, etc.), or the like. Examples of the oily medium include sesame oil and soybean oil, which may also be used in combination with a dissolution aid such as benzyl benzoate and benzyl alcohol. The may further be formulated with a buffer (e.g., phosphate buffer, sodium acetate buffer, etc.), a soothing agent (e.g., benzalkonium chloride, procaine hydrochloride, etc.), a stabilizer (e;g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to mammalian animal (e.g., human, rat, mouse, guinea pig, rabbit, sheep, swine, bovine, horse, cat, dog, monkey, etc.).

The dose of the peptide of the invention varies depending on target disease, subject to be administered, route for administration, etc.; for example, in oral administration of the peptide of the invention for the treatment of a digestive disease, the dose is normally about 1 mg to about 1000 mg, preferably about 10 to about 500 mg, and more preferably about 10 to about 200 mg per day for adult (as 60 kg body weight). In parenteral administration, the single dose varies depending on subject to be administered, target disease, etc. but it is advantageous for the treatment of a digestive disease to administer the active ingredient intravenously at a daily dose of about 1 to about 1000 mg, preferably about 1 to about 200 mg, and more preferably about 10 to about 100 mg for adult (as 60 kg body weight). For other animal species, the corresponding dose as converted per 60 kg body weight can be administered.

(2) Screening of a Compound or its Salt that Alters the Binding Property Between the Peptide of the Invention and the Protein of the Invention The method of screening a compound or its salt that alters the binding property between the peptide of the invention and the protein of the invention, which comprises using the peptide of the invention and the protein as well as the partial peptide of the invention, or the kit for screening a compound or its salt that alters the binding property between the peptide of the invention and the protein of the invention, which comprises using the peptide of the invention and the protein of the invention (hereinafter merely referred to as the screening method of the invention, or the screening kit of the invention) is described below in detail.

By using the protein of the invention, or by constructing the expression system of a recombinant form of the protein of the invention and using the binding assay system to the peptide of the invention (ligand-receptor assay system) through the expression system, the compound or salts thereof that alter the binding property between the peptide of the invention and the protein of the invention (e.g., peptide, protein, a non-peptide compound, a synthetic compound, fermentation product, etc.) can be screened.

Such compounds include compounds (ZAQ agonists) that have a cell-stimulating activity mediated by the protein of the invention (e.g., the activity that promotes or inhibit arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.), compounds that do not have the cell-stimulating activity (ZAQ antagonists), and the like. The term "alters the binding property between the peptide of the invention and the protein of the invention" is used to include both cases where binding of the peptide of the invention to the protein of the invention is inhibited and promoted.

Thus, the present invention provides the method of screening a compound or its salt that alters the binding property between the peptide of the invention and the peptide of the invention, which comprises comparing (i) the case wherein the peptide of the invention is brought in contact with the protein of the invention and (ii) the case wherein the peptide of the invention and a test compound are brought in contact with the protein of the invention.

According to the screening method of the invention, the method comprises assaying, for example, the binding amount of the peptide of the invention to the protein of the invention, the cell-stimulating activity, or the like, (i) when the peptide of the invention is brought in contact with the protein of the invention described above and (ii) when the peptide of the invention and a test compound are brought in contact with the protein of the invention described above, and comparing (i) and (ii).

Specifically, the screening method of the invention includes:

(1) a method of screening a compound or its salt that alters the binding property between the peptide of the invention and the protein of the invention, which comprises assaying the binding amount of a labeled form of the peptide of the invention to the protein of the invention, in the case wherein a labeled form of the peptide of the invention is brought in contact with the protein of the invention above and in the case wherein a labeled form of the peptide of the invention and a test compound are brought in contact with the protein of the invention, and comparing them;

(2) a method of screening a compound or its salt that alters the binding property between the peptide of the invention and the protein of the invention, which comprises assaying the binding amount of a labeled form of the peptide of the invention to a cell containing the protein of the invention or its cell membrane, in the case wherein a labeled form of the peptide of the invention is brought in contact with the cell containing the protein of the invention or its cell membrane and in the case wherein a labeled form of the peptide of the invention and a test compound are brought in contact with the cell containing the protein of the invention or its cell membrane, and comparing them;

(3) a method of screening a compound or its salt that alters the binding property between the peptide of the invention and the protein of the invention, which comprises assaying the binding amount of a labeled form of the peptide of the invention to the protein of the invention, in the case wherein a labeled form of the peptide of the invention is brought in contact with the protein of the invention expressed in a cell membrane by culturing a transformant containing a DNA encoding the protein of the invention and in the case wherein a labeled form of the peptide of the invention and a test compound are brought in contact with the protein of the invention expressed in a cell membrane by culturing a transformant containing a DNA encoding the protein of the invention, and comparing them;

(4) a method of screening a compound or its salt that alters the binding property between the peptide of the invention and the protein of the invention, which comprises assaying the cell-stimulating activity mediated by the protein of the invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.), when the peptide of the invention is brought in contact with a cell containing the protein of the invention and when the peptide of the invention and a test compound are brought in contact with a cell containing the protein of the invention, and comparing the activity; and, (5) a method of screening a compound or its salt that alters the binding property between the peptide of the invention and the protein of the invention, which comprises assaying the cell-stimulating activity mediated by the protein of the invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.), when the peptide of the invention is brought in contact with the protein of the invention expressed in a cell membrane by culturing a transformant containing a DNA encoding the protein of the invention and when the peptide of the invention and a test compound are brought in contact with the protein of the invention expressed on a cell membrane by culturing a transformant containing a DNA encoding the protein of the invention, and comparing the activity; and the like.

The screening method of the invention will be described below more specifically.

First, the protein of the invention, which is used for the screening method of the invention, may be any protein, so long as it contains the protein of the invention described above. However, since it is very difficult to obtain human-derived organs especially, the protein of the invention, etc. expressed abundantly by use of recombinants is suitable for use in the screening.

In the manufacture of the protein of the invention, the methods described above may be used.

When the cell containing the protein of the invention or its cell membrane fraction is used in the screening method of the invention, the procedures later described apply to the method.

When the cell containing the protein of the invention is used, the cell may be fixed with glutaraldehyde, formalin, etc. The fixation may be carried out by a publicly known method.

The cell containing the protein of the invention refers to a host cell expressing the protein of the invention. Examples of such a host cell include Escherichia coli, Bacillus subtilis, yeast, insect cells, animal cells, etc.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or Polytron (manufactured by Kinematica Inc.), disruption by ultrasonication, disruption by cell spraying via a thin nozzle under increasing pressure using a French press, etc., and the like. Cell membranes are fractionated mainly by fractionation using a centrifugal force such as for fractionation centrifugation, density gradient centrifugation, etc. For example, cell disruption fluid is centrifuged at a low rate (500 rpm to 3,000 rpm) for a short period of time (normally-about 1 minute to about 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in the protein of the invention expressed and membrane components such as cell-derived phospholipids, membrane proteins, or the like.

The amount of the protein of the invention contained in the cells containing the protein of the invention or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) for screening the compound that alters the binding property between the peptide of the invention and the protein of the invention, an appropriate fraction of the protein of the invention and a labeled form of the protein of the invention are required. The fraction of the protein of the invention is preferably a fraction of a naturally occurring form of the protein of the invention or a fraction of a recombinant type of the protein of the invention having an equivalent activity. Herein, the term equivalent activity is intended to mean a ligand binding activity, etc. As a labeled form of the peptide of the invention, there may be used the peptide of the invention, etc., which are labeled with $[^3H]$, $[^{125}I]$, $[^{14}C]$, $[^{35}S]$, etc. In particular, there may be used a labeled form of the peptide of the invention, which is prepared by publicly known methods using a Bolton-Hunter reagent.

More specifically, the compound that alters the binding property between the peptide of the invention and the protein of the invention is screened by the following procedures. First, a receptor preparation is produced by suspending cells containing the protein of the invention or the membrane fraction thereof in a buffer appropriate for use in the screening method. Any buffer can be used so long as it does not interfere the ligand-receptor binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the protein of the invention or the peptide of the invention with a protease, a protease inhibitor such as PMSF, leupeptin, E-64 (manufactured by Peptide Institute, Inc.), pepstatin, etc. may also be added. A given amount (5,000 cpm to 500,000 cpm) of the labeled peptide of the invention is added to 0.01 ml to 10 ml of the receptor solution, in which $10^{-4}$ to $10^{-1}$ μM of a test compound is co-present. To determine the amount of non-specific binding (NSB), a reaction tube charged with an unlabeled form of the peptide of the invention in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound having a competitive inhibition activity.

For assaying the binding between the protein of the invention and the peptide of the invention, BIAcore (manufactured by Amersham Pharmacia Biotech Co.) may also be employed. In this technique, the peptide of the invention is immobilized onto a sensor chip by the amino coupling method following the protocol attached to the device. A buffer such as phosphate buffer, Tris buffer, etc., which contains the protein of the invention purified from the cells containing the protein of the invention or transformants containing a DNA encoding the protein of the invention, or a membrane fraction containing the protein of the invention, or the purified protein of the invention or a membrane fraction containing the protein of the invention and a test-compound, is passed over the sensor chip at a flow rate of 2 to 20 μl/min. By monitoring that the test compound co-present alters the change in surface plasmon resonance caused by binding of the protein of the invention to the peptide of the invention on the sensor chip, the compound that alters the binding of the protein of the invention to the peptide of the invention can be screened. According to this technique, the alteration can be likewise measured by the procedure which involves immobilizing the protein of the invention onto a sensor chip and passing over the sensor chip a buffer solution such as phosphate buffer, Tris buffer, etc., which contains the peptide of the invention, or the peptide of the invention and a test compound. Examples of the test compound are the same as those given above.

The method (4) or (5) above for screening the compound that alters the binding property between the peptide of the invention and the protein of the invention can be implemented as follows. For example, the cell stimulating activity mediated by the protein of the invention (e.g., the activity that promotes or suppresses arachidonic acid release, acetylcholine release, intracellular Ca$^{2+}$ release, intracellular cAMP production, intracellular cGMP production, inositol phosphate production, change in cell membrane potential, phosphorylation of intracellular proteins, activation of c-fos, pH reduction, etc.) can be assayed by publicly known methods, or using assay kits commercially available. Specifically, the cells containing the protein of the invention are first cultured on a multiwell plate, etc. Prior to screening, the medium is replaced with fresh medium or cell with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to a degrading enzyme contained in the cells, an inhibitor against such as a degrading enzyme may be added prior to the assay. For detecting the activity such as the cAMP production suppression, the baseline production in the cells is increased by forskolin or the like and the suppressing effecton the increased baseline production can be detected.

For screening by assaying the cell stimulating activity, appropriate cells, in which the protein of the invention is expressed, are required. Preferred examples of the cells, in which the protein of the invention is expressed, are the aforesaid cell line in which the protein of the invention is expressed, and the like. The protein of the invention-expressed cell, which is a transformant, may be either a stably expressed strain or a temporarily expressed strain. For animal cells, the aforesaid cells of the same kind are employed as well.

Examples of the test compounds include peptides, proteins, non-peptide compounds, synthetic compounds, fermentation products, cell extracts, plant extracts, animal tissue extracts, etc.

In more detail, the following assay systems (1) through (12) employed for the ligand-receptor assay system supra are described below.

(1) When a receptor expression cell is stimulated by a receptor agonist, G protein in the cell is activated and GTP is bound thereto. This phenomenon is observed also in a membrane fraction of the receptor expression cell. Usually, GTP is hydrolyzed into GDP. However, when GTPγS is previously added to the reaction solution, GTPγS is bound to G protein as in GTP but is not hydrolyzed so that a state of GTPγS bound to the G protein-containing cell membrane is maintained. When labeled GTPγS is used, the residual radioactivity on the cell membrane is measured, whereby the receptor expression cell stimulating activity of a receptor agonist can be assayed. Using this reaction, the stimulating activity of the peptide of the invention on the cells in which the protein of the invention has been expressed can be assayed. This is an assay method using the membrane fraction containing the protein of the invention as described in (1) through (3), not using cells containing the protein of the invention as in (4) and (5) described above. According to this method, however, the cell stimulating activity is assayed as in (4) and (5). In this assay system, the substance showing the activity of promoting the binding of GTPγS to the membrane fraction containing the protein of the invention is an agonist. Herein, the compound that alters the binding property between the peptide of the invention and the protein of the invention can be screened by adding the peptide of the invention or the peptide of the invention and a test compound and monitoring a change occurred on the GTPγS binding promoting activity to the membrane fraction containing the protein of the invention, as compared to administration of the peptide of the invention alone. In this case, the compound that shows suppression of the GTPγS binding promoting activity of the peptide of the invention on the membrane fraction containing the protein of the invention can be selected as a candidate substance having a competitive inhibition activity. On the other hand, an agonist can be screened by administering a test compound alone and monitoring the GTPγS binding promoting activity in the cell membrane fraction containing the protein of the invention.

An example of the screening method is specifically described below. The cell membrane fraction containing the protein of the invention is diluted with a buffer for membrane dilution (50 mM Tris, 5 mM MgCl$_2$, 150 mM NaCl, 1 μM GDP, 0.1% BSA, pH 7.4). A degree of dilution varies depending upon the amount of the protein of the invention expressed. The dilution is dispensed by 0.2 ml each in Falcon 2053, to which the peptide of the invention or the peptide of the invention and a test compound are added. [$^{35}$S] GTPγS is added to the mixture to a final concentration of 200 pM. After maintaining at 25° C. for an hour, ice-cooled wash buffer (50 mM Tris, 5 mM MgCl$_2$, 150 mM NaCl, 0.1% BSA, 0.05% CHAPS, pH 7.4, 1.5 ml) is added to the mixture followed by filtration through a glass fiber filter paper GF/F. After keeping at 65° C. for 30 minutes, the mixture is dried and the radioactivity of [$^{35}$S] GTPγS bound to the membrane fraction remaining on the filter paper is measured with a liquid scintillation counter. When the radioactivity in the experimental group added with the peptide of the invention alone is defined as 100% and the radioactivity in the experimental group not added with the peptide of the invention is defined as 0%, an effect of the test compound on the GTPγS binding promoting activity by the peptide of the invention is worked out. The test compound showing the GTPγS binding promoting activity of, for example, 50% or less can be selected as a candidate compound having a competitive inhibition activity.

(2) In the cells in which the protein of the invention has been expressed, an amount of intracellular cAMP decreases by stimulation with the peptide of the invention. Utilizing this reaction, the stimulating activity of the peptide of the invention on the cells in which the protein of the invention has been expressed can be assayed.

The amount of cAMP production in various animal cells in which the protein of the invention has been expressed can be assayed by RIA using an anti-cAMP antibody, whose antibody is obtained from immunized mouse, rat, rabbit, goat, bovine, etc., and $^{125}$I-labeled cAMP (both commercially available) or by other EIA system using an anti-cAMP antibody and labeled cAMP in combination. Quantification by the SPA technique is also possible, in which beads containing scintillants bearing anti-cAMP antibodies immobilized using protein A or antibodies to IgG, etc. of animal used to produce the anti-cAMP antibodies and $^{125}$I-labeled cAMP are used (a kit manufactured by Amersham Pharmacia Biotech is used).

In this system, the compound that alters binding of the protein of the invention to the peptide of the invention can be screened by increasing the amount of intracellular cAMP by a ligand such as forskolin, calcitonin or the like capable of increasing the amount of intracellular cAMP and monitoring that suppression of the intracellular cAMP production by administration of the peptide of the invention alone is altered by adding the peptide of the invention or the peptide of the invention and a test compound. In this case, the compound that shows an activity of inhibiting the cAMP production inhibitory activity of the protein of the invention has been expressed by the peptide of the invention can be selected as a candidate substance having a competitive inhibition activity. On the other hand, a compound showing an agonist activity can be screened by monitoring the cAMP production inhibition activity when a test compound alone is added.

The screening method is described below more specifically. CHO cells wherein the protein of the invention is expressed (ZAQC-B1 cell; EXAMPLE 3 (3-5) later described) are inoculated on a 24 well plate in $5\times10^4$ cells/well followed by cultivation for 48 hours. The cells are washed with Hanks' buffer (pH 7.4) containing 0.2 mM 3-isobutylmethylxanthine, 0.05% BSA and 20 mM HEPES (hereinafter Hanks' buffer (pH 7.4) containing 0.2 mM 3-isobutylmethylxanthine, 0.05% BSA and 20 mM HEPES is referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 nM of the peptide of the invention, or 1 nM of the peptide of the invention and a test compound is/are added to 0.25 ml of the reaction buffer containing 2 μM forskolin. The mixture is added to the cells followed by reacting at 37° C. for 24 minutes. The reaction is terminated by adding 100 μl of 20% perchloric acid. The reaction mixture is then put on ice for an hour to extract intracellular cAMP. The amount of cAMP in the extract is measured using a cAMP EIA kit (Amersham Pharmacia Biotech). Taking the amount of cAMP produced by forskolin stimulation as 100% and the amount of cAMP inhibited by the addition of 1 nM the peptide of the invention as 0%, an effect of the test compound on the cAMP production inhibitory activity by the peptide of the invention is calculated. A test compound that inhibits the activity of the peptide of the invention to reduce the cAMP production activity, e.g., to 50% or more can be selected as a candidate substance having a competitive inhibition activity.

To determine the cAMP production promoting activity, the amount of cAMP produced by adding a test compound to CHO cells wherein the protein of the invention is expressed, without adding forskolin is quantified by the procedure described above.

(3) A DNA containing CRE (cAMP response element) is inserted into a multicloning site upstream a luciferase gene in a PicaGene Basic Vector or a PicaGene Enhancer Vector (Toyo Ink Mfg. Co., Ltd.), which is made a CRE-reporter gene vector. In a CRE-reporter gene vector-transfected cell, stimulation associated with increase cAMP induces expression of CRE-mediated luciferase gene and luciferase protein production subsequent thereto. That is, by assaying the luciferase activity, a change in amount of cAMP in the CRE-reporter gene vector transfected cell can be detected. Utilizing the cells wherein the protein of the invention is expressed, to which the CRE-reporter gene vector is transfected, a compound that alters the binding of the peptide of the invention to the protein of the invention can be screened. The screening method is specifically described below.

The CRE-reporter gene transfected the cells in which the protein of the invention has been expressed are inoculated on a 24-well plate in $5\times10^3$ cells/well followed by cultivation for 48 hours. The cells are washed with Hanks' buffer (pH 7.4) containing 0.2 mM 3isobutylmethylxanthine, 0.05% BSA and 20 mM HEPES (hereinafter Hanks' buffer (pH 7.4) containing 0.2 mM 3-isobutylmethylxanthine, 0.05% BSA and 20 mM HEPES is referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 nM the peptide of the invention or 1 nM the peptide of the invention and a test compound as well as 0.25 ml of the reaction buffer containing 2 μM forskolin are added to the cells followed by reacting at 37° C. for 24 minutes. The cells are dissolved in a cell lysis agent for PicaGene (Toyo Ink Mfg. Co., Ltd.) and a luminescence substrate (Toyo Ink Mfg. Co., Ltd.) is added to the lysate. Luminescence emitted by luciferase is measured by a luminometer, a liquid scintillation counter or a top counter. An effect of the compound that alters the binding of the peptide of the invention to the protein of the invention can be assayed by comparing the luminescence amounts of luciferase with the case where the peptide of the invention is administered solely. In this case, an increase of the luminescence amount by forskolin stimulation is suppressed by administration of the peptide of the invention. The compound that can retrieve the inhibition can be selected as a candidate substance having a competitive inhibition activity. On the other hand, an agonist can be screened as well by administering a test compound alone and monitoring suppression of the luminescence amount intensified by forskolin stimulation in the same way as in the peptide of the invention.

In addition to luciferase, alkaline phosphatase, chloramphenicol acetyltransferase or β-galactosidase may be employed as the reporter gene. The enzymatic activity of gene products from these reporter genes can be readily assayed using assay kits commercially available. The alkaline phosphatase activity, the chloramphenicol acetyltransferase activity and the β-galactosidase activity can be assayed using, e.g., Lumi-Phos 530 manufactured by Wako Pure Chemical Industries, Ltd., FAST CAT chloramphenicol Acetyltransferase Assay Kit manufactured by Wako Pure Chemical Industries, Ltd. and Aurora Gal-XE manufactured by Wako Pure Chemical Industries, Ltd., respectively.

(4) The cells, in which the protein of the invention has been expressed, extracellularly release arachidonic acid metabolites as a result of stimulation by the peptide of the invention. By previously incorporating radioactive arachidonic acid into the cells, the activity can be assayed by measuring the radioactivity released outside the cells. In this case, the compound that affects the binding of the peptide of the invention to the protein of the invention by the peptide of the invention can be screened by adding the peptide of the invention or the peptide of the invention and a test compound and monitoring an effect of the peptide of the invention on the arachidonic acid metabolite releasing activity. In this case, the compound that inhibits the arachidonic acid metabolite releasing activity by the peptide of the invention can be selected as a candidate substance having a competitive inhibition activity. On the other hand, a compound showing an agonist activity can be screened similarly by administering a test compound alone and monitoring the arachidonic acid metabolite releasing activity by the cells in which the protein of the invention has been expressed. The method of screening a compound that affects the binding of the peptide of the invention to the protein of the invention is described below more specifically.

CHO cells in which the protein of the invention is expressed are inoculated on a 24-well plate in $5\times10^4$ cells/well. After cultivation for 24 hours, [$^3$H] arachidonic acid is added to the cells in 0.25 μCi/well. Sixteen hours after the addition of [$^3$H] arachidonic acid, the cells are washed with Hanks' buffer (pH 7.4) containing 0.05% BSA and 20 mM HEPES. To each well is added 500 μl of a solution obtained by dissolving a 10 nM final concentration of the peptide of the invention or a 10 nM final concentration of the peptide of the invention and a test compound in Hanks' balanced salt solution (pH 7.4) containing 0.05% BSA and 20 mM HEPES. Hereinafter Hanks' buffer (pH 7.4) containing 0.05% BSA and 20 mM HEPES is referred to as a reaction buffer. After incubating 37° C. for 60 minutes, 400 μl of the reaction solution is charged in a scintillator and the amount of [$^3$H] arachidonic acid metabolites released in the reaction solution is measured using a scintillation counter. When the amount of [$^3$H] arachidonic acid metabolites in the medium of the reaction buffer not added with the protein of the invention is taken as 0% and the amount of [$^3$H] arachidonic acid metabolites in the medium added with 10 nM of the peptide of the invention is taken as 100%, an effect of the test compound on the binding of the peptide of the invention to the protein of the invention is calculated. The test compound that reduces the arachidonic acid metabolite producing activity, e.g., to 50% or less can be selected as a candidate substance having a competitive inhibition activity.

(5) When the cells in which the protein of the invention has been expressed are stimulated by the peptide of the invention, an intracellular $Ca^{2+}$ ion concentration increases. Utilizing this, an effect of a test compound on the binding of the peptide of the invention to the protein of the invention can be monitored. Specifically, the effect can be monitored in accordance with the procedures in EXAMPLES 3 (3-5) and 5 (5-3-4) later described.

The cells in which the protein of the invention has been expressed are inoculated on a sterilized cover glass for microscopy. Two days after, the culture medium is replaced by HBSS in which 4 mM Fura-2 AM (Dojin Kagaku Kenkyusho) is suspended, followed by standing at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when the peptide of the invention or the peptide of the invention and a test compound is/are added. In this case, the compound that affects the binding of the peptide of the invention to the protein of the invention can be screened by measuring a change in fluorescence intensity caused by addition of the test compound, as compared to the case where the peptide of the invention is administered solely.

Also, FLIPR (manufactured by Molecular Device Co.) may be used as described below. That is, Fluo-3 AM (manufactured by Dojin Kagaku Kenkyusho) is added to a cell suspension to incorporate Fluo-3 AM into the cells. The supernatant is washed several times through centrifugation and the cells are inoculated on a 96-well plate. After setting in the FLIPR device, the peptide of the invention or the peptide of the invention and a test compound is/are added as in Fura-2. The compound that affects the binding of the peptide of the invention to the protein of the invention can be screened by measuring a change in fluorescence intensity caused by addition of the test compound, as compared to the case where the peptide of the invention is administered solely.

In these cases, the compound that inhibits an increase of fluorescence intensity by the peptide of the invention can be selected as a candidate substance having a competitive inhibition activity. On the other hand, an agonist may also be screened by monitoring an increase of the fluorescence intensity when the test compound alone is added.

In the cells in which the protein of the invention has been expressed, when a protein gene (e.g., aequorin, etc.) that emits light in association with an increase of intracellular $Ca^{2+}$ ions is co-expressed and that gene (e.g., aequorin, etc.) changes to $Ca^{2+}$-bound aequorin by an increase of intracellular $Ca^{2+}$ ion concentration to emit light. Utilizing this light emission, the compound that affects the binding of the peptide of the invention to the protein of the invention can be screened by adding the peptide of the invention or the peptide of the invention and a test compound and, monitoring that light emission observed by addition of the test compound changes, as compared to the case where the peptide of the invention alone is administered. The method is the same as described above, except that the fluorescent substance is not incorporated into the cells.

(6) It is known that when a receptor agonist is added to a receptor-expressing cell, a level of intracellular inositol triphosphate increases. By monitoring the reaction in the protein cells of the present invention induced by the peptide of the invention, the compound that affects the binding of the peptide of the invention to the protein of the invention can be screened. On one day after inoculation of the cells on a 24-well plate, myo-[2-$^3$H]inositol (2.5 microCi/well) is added to each well. In this medium the cells are cultivated for one day. After thoroughly washing, the peptide of the invention or the peptide of the invention and a test compound is/are added to the cells. The reaction is then terminated by adding 10% perchloric acid. The reaction mixture is neutralized with 1.5 M KOH and 60 mM HEPES solution and then passed through a column packed with 0.5 ml of Ag1×8 resin (Bio-Rad). After washing with 5 mM $Na_2BO_3$ and 60 mM $HCOONH_4$, the radioactivity eluted with 1M $HCOONH_4$ and 0.1M HCOOH is measured with a liquid scintillation counter. When the radioactivity in the medium of the reaction buffer without adding the peptide of the invention is made 0% and the radioactivity in the medium added with the peptide of the invention is made 100%, an effect of the test compound on the binding of the peptide of the invention to the protein of the invention is calculated. The test compound that inhibits the inositol triphosphate production activity, e.g., to 50% or less can be selected as a candidate substance having a competitive inhibition activity. On the other hand, an agonist can be screened similarly by monitoring an increase of the inositol triphosphate production activity when the test compound alone is added.

(7) A DNA containing TRE (TPA response element) is inserted into a multicloning site upstream a luciferase gene in a PicaGene Basic Vector or a PicaGene Enhancer Vector (Toyo Ink Mfg. Co., Ltd.), which is made a TRE-reporter gene vector. In a TRE-reporter gene vector-transfected cell, stimulation accompanied by an increase of intracellular $Ca^{2+}$ ion concentration induces TRE-mediated luciferase gene expression and luciferase protein production subsequent thereto. That is, by assaying the luciferase activity, a change in the amount of calcium ions in the TRE-reporter gene vector transfected cell can be detected. Utilizing the TRE-reporter gene vector-transfected the cells in which the protein of the invention has been expressed, a compound that alters the binding of the peptide of the invention to the protein of the invention can be screened. The screening method is specifically described below.

The TRE-reporter gene-transfected cells in which the protein of the invention has been expressed are inoculated on a 24-well plate in 5×10$^3$ cells/well followed by cultivation for 48 hours. After the cells are washed with Hanks' buffer (pH 7.4) containing 0.05% BSA and 20 mM HEPES, 10 nM of the peptide of the invention or 10 nM of the peptide of the invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured by a luminometer, a liquid scintillation counter or a top counter. An effect of the compound that alters the binding of the peptide of the invention to the protein of the invention can be measured by comparing the luminescence amount by luciferase with the case when the peptide of the invention alone is added. In this case, the amount of luminescence increases with an increase in intracellular $Ca^{2+}$ ion concentration by administration of the peptide of the invention and the compound that suppresses the increase can be selected as a candidate substance having a competitive inhibition activity. On the other hand, an agonist can be screened as well by monitoring an increase of luminescence in the same way as in the peptide of the invention, when the test compound alone is administered.

In addition to luciferase, alkaline phosphatase, chloramphenicol acetyltransferase or β-galactosidase may be employed as the reporter gene. The enzymatic activity of gene products from these reporter genes can easily be assayed as described below, using assay kits commercially available. The alkaline phosphatase activity, the chloramphenicol acetyltransferase activity and the β-galactosidase activity can be assayed using, e.g., Lumi-Phos 530 manufactured by Wako Pure Chemical Industries, Ltd., FAST CAT chloramphenicol Acetyltransferase Assay Kit manufactured by Wako Pure Chemical Industries, Ltd. and Aurora Gal-XE manufactured by Wako Pure Chemical Industries, Ltd., respectively.

(8) In the cells in which the protein of the invention has been expressed in response to the peptide of the invention, growth is observed by MAP kinase activation. This growth can be assayed by the MAP kinase activity, thymidine uptake or cell counting (MTT, etc.). Utilizing such, the compound that alters the binding of the peptide of the invention to the protein of the invention can be screened.

The MAP kinase activity can be readily assayed by adding the peptide of the invention or the peptide of the invention and a test compound to the cells, obtaining a MAP kinase fraction from a cell lysate by immunoprecipitation using an anti-MAP kinase antibody and then using, e.g., a MAP Kinase Assay Kit manufactured by Wako Pure Chemical Industries, Ltd. and γ-$[^{32}P]$-ATP. The thymidine uptake activity can be assayed by inoculating the cells in which the protein of the invention has been expressed, adding the peptide of the invention or the peptide of the invention and a test compound to the cells, further adding [methyl-$^3$H]-thymidine, causing cell lysis and then counting the radioactivity of the labeled thymidine taken up into the cells with a liquid scintillation counter.

The growth of the cells in which the protein of the invention has been expressed can be determined as well by inoculating the expression cells, adding the peptide of the invention or the peptide of the invention and a test compound, further adding MTT (3-(4,5-dimethyl-2-thiazolyl)-2, 5-diphenyl-2H-tetrazolium bromide), taking MTT up into the cells thereby to convert into MTT formazan, causing cell lysis with isopropanol which is rendered acidic with hydrochloric acid, and then measuring absorption at 570 nm.

The method of screening the compound that alters the binding of the peptide of the invention to the protein of the invention utilizing the labeled thymidine uptake activity is described below specifically.

The cells in which the protein of the invention has been expressed are inoculated on a 24-well plate in 5000 cells/well followed by incubation for one day. Next, the cells are incubated in a serum-free medium for 2 days to bring the cells under starvation. The peptide of the invention or the peptide of the invention and a test compound is/are added to-the cells. After incubation for 24 hours, [methyl-$^3$H] thymidine is added in 0.015 MBq/well followed by incubation for 6 hours. After washing the cells with PBS, methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with a 0.3 N sodium hydroxide solution, the radioactivity in the lysate is measured with a liquid scintillation counter. An effect of the compound that alters the binding of the peptide of the invention to the protein of the invention can be determined by comparing with an increase of the radioactivity by thymidine uptake when the peptide of the invention alone is administered. In this case, the compound that suppresses an increase of the radioactivity by administering the peptide of the invention can be selected as a candidate substance having a competitive inhibition activity. On the other hand, an agonist can be screened by monitoring an increase of the radioactivity in the same way as in the peptide of the invention when the test compound alone is administered.

(9) When the peptide of the invention is added to the cells in which the protein of the invention has been expressed, K channel is activated so that $K^+$ ions present within the cells are effluxed extracellularly. Since $Rb^+$ ions in the related elements to $K^+$ ions flow out of the cells through the K channel without being distinguished from K+ions, labeled Rb ($[^{86}Rb]$) is added to the cells to permit intracellular uptake of the isotope. Then, the efflux of $[^{86}Rb]$ that flows out by the peptide of the invention stimulation is measured to assay the action of the peptide of the invention. The method for screening the compound that alters the binding of the peptide of the invention to the protein of the invention utilizing $[^{86}Rb]$ efflux activity is described below specifically.

Two days after inoculation on 24 wells the cells in which the protein of the invention has been expressed are kept warm for 2 hours in a medium containing 1 mCi/ml of $^{86}RbCl$. The medium is thoroughly washed to completely remove $^{86}RbCl$ in the outer liquid. The peptide of the invention or the peptide of the invention and a test compound is/are added to the cells. The outer liquid is recovered 30 minutes later and the radioactivity is counted with a γ counter. An effect of the compound that alters the binding of the peptide of the invention to the protein of the invention can be assayed by comparing an increase of the radioactivity by $[^{86}Rb]$ efflux with the case when the peptide of the invention alone is administered. In this case, the compound that suppresses an increase of the radioactivity by administration of the peptide of the invention can be selected as a candidate substance having a competitive inhibition activity. On the other hand, an agonist can be screened as well by monitoring an increase of the radioactivity in the same way as in the peptide of the invention when the test compound alone is administered.

(10) The protein of the invention activity can be assayed by measuring extracellular pH (acidification rate) that the cells in which the protein of the invention has been expressed changes in response to the peptide of the invention, using a Cytosensor device (Molecular Device Co.). The method for screening the compound that alters the binding of the peptide of the invention to the protein of the invention through the extracellular pH measurement using the Cytosensor device is specifically described below.

The cells in which the protein of the invention has been expressed are incubated overnight in a capsule for the Cytosensor device, which is set in a chamber of the device to reflux 0.1% BSA-containing RPMI 1640 medium (manufactured by Molecular Device Co.) until the extracellular pH becomes stable 約2時間. After the pH becomes stable, a medium containing the peptide of the invention or the peptide of the invention and a test compound is refluxed on the cells to measure a change in pH caused thereby. An effect of the compound that alters the binding of the peptide of the invention to the protein of the invention can be assayed by comparing a change of extracellular pH in the cells in which the protein of the invention has been expressed with the case when the peptide of the invention is administered solely. In this case, the compound that suppresses a change of extracellular pH the protein of the invention by administering the peptide of the invention can be selected as a candidate substance having a competitive inhibition activity. On the other hand, an agonist can be screened by monitoring a change of extracellular pH in the same way as in the peptide of the invention when the test compound alone is administered.

(11) In *Saccharomyces Cerevisiae*, sex pheromone receptor STe2 of haploid α-mating type (MATα) is coupled to G protein Gpal to activate MAP kinase in response to sex pheromone α-mating factor, whereby Far1 (cell-cycle arrest) and transcription activator Ste12 are activated. Ste12 stimulates expression of a wide variety of genes, including FUS1 which is associated with mating. On the other hand, regulator Sst2 functions to inhibit the foregoing process. In this system, an attempt has been made on an assay system for the receptor agonist/receptor reaction, which involves producing receptor gene-integrated yeast, activating the signal transduction system in yeast cells by receptor agonist stimulation and using the resulting growth, etc. as an index (Pausch, M. H., Trends in Biotechnology, 15, 487–494 (1997)). Utilizing this receptor gene-integrated yeast system, the compound that alters the binding of the peptide of the invention to the protein of the invention can be screened.

Ste2 in MATα yeast and a gene encoding Gpal are removed and instead, a gene from the protein of the invention and a gene encoding Gpal-Gai2 fused protein are introduced. A gene encoding Far is removed to cause no cell-cycle arrest and a gene encoding Sst is removed to increase the sensitivity in response to the peptide of the invention. Furthermore, FUS1-HIS3 gene, which is FUS1 ligated with histidine biosynthesis gene HIS3, is introduced. The foregoing genetic recombinant engineering can easily be performed, e.g., by the method reported by Price et al. (Price, L. A. et al., Molecular and Cellular Biology, 15, 6188–6195 (1995)), using the protein of the invention in place of somatostatin receptor type 2 (SSTR2) gene. The thus constructed transformant yeast is responsive to the peptide of the invention as a ligand to the protein of the invention in a high sensitivity so that MAP kinase is activated and a histidine biosynthesis enzyme is synthesized. Thus, the transformant becomes capable of growing in a histidine-deficient medium. Utilizing such, response of the yeast wherein the protein of the invention is expressed can be monitored using as an index growth of the yeast in a histidine-deficient medium. The method for screening the compound that alters the binding of the peptide of the invention to the protein of the invention is described below.

The thus produced transformant yeast is incubated overnight in complete synthesis liquid medium and added to a histidine-free agar medium in $2\times10^4$ cells/ml, followed by inoculation on a square Petri dish of 9×9 cm. After the agar is solidified, a sterilized filter paper impregnated with the peptide of the invention or the peptide of the invention and a test compound is put on the agar surface, followed by incubating at 30° C. for 3 days. An effect of the compound that alters the binding of the peptide of the invention to the protein of the invention can be assayed by comparing growth of yeast around the filter paper with the case when the peptide of the invention alone is administered. In this case, the compound that suppresses the growth of yeast by administration of the peptide of the invention can be selected as a candidate substance having a competitive inhibition activity. On the other hand, an agonist can be screened as well by monitoring the growth of yeast in the same way as in the peptide of the invention when the test compound alone is administered. Also, the compound that alters the binding of the peptide of the invention to the protein of the invention can also be assayed by previously adding the peptide of the invention to the agar medium, impregnating a sterilized filter paper with a test compound alone, incubating and monitoring that the growth of yeast over the entire surface of the Petri dish is affected at the periphery of the filter paper.

(12) When the protein of the invention gene RNA is injected into *Xenopus laevis* oocytes are stimulated by the peptide of the invention, an intracellular Ca ion concentration increases to cause a calcium-activated chloride current, which can be grasped as fluctuation in membrane potential (same as in the case where fluctuation occurs in a K ion level gradient). By monitoring the above reaction in the *Xenopus laevis* oocytes, wherein the protein of the invention is introduced, caused by the peptide of the invention, the compound that affects the binding of the peptide of the invention to the protein of the invention can be screened.

A female individual of *Xenopus laevis* is anesthetized by immersing in ice water and anatomized for taking out oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES, pH 7.4) at 19° C. for 1 to 6 hours at 150 rpm, until the oocytes are separated one from another. Washing is performed 3 times by replacing the outer liquid by the MBS solution followed by microinjection of poly(A)$^+$ SLT cRNA (50 ng/50 nl) with a micromanipulator. The mRNA for the protein of the invention may be prepared from tissues or cells or transcribed from plasmids in vitro. The oocytes are incubated in the MBS solution at 20° C. for 3 days. The oocytes are placed in a hole of a voltage clamp device, which is continuously perfused with Ringer's solution, and impaled with a glass microelectrode for voltage clamp and a glass microelectrodes for recording, in which (−) electrode is placed outside the oocytes. When the holding potential stabilizes, Ringer's solution containing the peptide of the invention or the peptide of the invention and a test compound is perfused to record a change in potential. An effect of the compound that alters the binding of the peptide of the invention to the protein of the invention can be measured by comparing a change in cell membrane potential of the *Xenopus laevis* oocytes, in which the protein of the invention is introduced, with the case when the peptide of the invention alone is administered. In this case, the compound that suppresses a change in cell membrane potential-caused by administration of the peptide of the invention can be selected as a candidate substance having a competitive inhibition activity. On the other hand, an agonist can be screened as well by monitoring the change in cell membrane potential in the same way as in the peptide of the invention where the test compound alone is administered.

In this system, the amount of alteration may be increased by introducing poly(A)⁺ RNAs of various G protein genes so that it becomes easier to monitor the reaction. Also, the reaction can be assayed by co-injecting poly(A)⁺ RNAs to a gene of a protein such as aequorin that emits light in the presence of Ca and monitoring the light emission, not a change in membrane potential.

The kits for screening a compound or its salts that alter the binding property between the peptide of the invention and the protein of the invention comprises the protein of the invention, cells containing the protein of the invention or cell membrane fractions containing the protein of the invention and the peptide of the invention.

The screening kits according to the present invention comprise, for example, the following:

1. Reagents for Screening (1) Assay Buffer and Wash Buffer

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Preparation of the Protein of the Invention

CHO cells on which the protein of the invention has been expressed are subcultured in a 12-well plate at the rate of $5 \times 10^5$ cells/well and then cultured at 37° C. under 5% $CO_2$ and 95% air for 2 days.

(3) Labeled Ligand

The peptide of the invention labeled with commercially available [$^3$H], [$^{125}$I], [$^{14}$C], [$^{35}$S], etc.

The labeled peptide is dissolved in a suitable solvent or buffer, and the solution is stored at 4° C. or −20° C., which is diluted to 1 μM with an assay buffer at use.

(4) Standard Ligand Solution

The peptide of the invention is dissolved in PBS supplemented with 0.1% bovine serum albumin (manufactured by Sigma, Inc.) in a concentration of 1 mM, and the solution is stored at −20° C.

2. Assay Method (1) Cells are cultured in a 12-well tissue culture plate to express the protein of the invention. After washing the cells twice with 1 ml of the assay buffer, 490 μl of the assay buffer is added to each well.

(2) After 5 μl of a test compound solution of $10^{-3}$ to $10^{-10}$ M is added, 5 μl of a labeled form of the peptide of the invention is added to the system followed by reacting at room temperature for an hour. To determine the amount of the non-specific binding, the peptide of the invention of $10^{-3}$ M is added in an amount of 5 μl, instead of the test compound.

(3) The reaction mixture is removed and washed 3 times with 1 ml each of the wash buffer. The labeled peptide of the invention bound to the cells is dissolved in 0.2N NaOH-1% SDS and mixed with 4 ml of a liquid scintillator A (manufactured by Wako Pure Chemical Industries, Ltd.).

(4) Radioactivity is measured using a liquid scintillation counter (manufactured by Beckmann) and PMB (percent of the maximum binding) is calculated in accordance with the following equation 1:

$$PMB = [(B-NSB)/(B_0-NSB)] \times 100$$

wherein:
PMB: percent of the maximum binding
B: value when a sample is added
NSB: non-specific binding
$B_0$: maximum binding The compound or its salt, which is obtainable by the screening method or the screening kit of the invention, is the compound that alters the binding property between the peptide of the invention and the peptide of the invention (that promotes or inhibits the binding). Specifically, these compounds are compounds or salts thereof that exhibit the cell stimulating activity mediated by the protein of the invention (so-called the agonist to the protein of the invention (ZAQ agonist)), or compounds that do not exhibit the cell stimulating activity (so-called antagonist to the protein of the invention (ZAQ antagonist)). Examples of such compounds include peptides, proteins, non-peptide compounds, synthetic compounds, fermentation products, and the like. These compounds may be either novel compounds or publicly known compounds.

In order to evaluate whether the compound is the agonist or antagonist to the protein of the invention described above, it is determined by (i) or (ii) below.

(i) According to the screening methods (1) to (3), binding assay is carried out to obtain the compound that alters the binding property between the peptide of the invention and the protein of the invention (especially, the compound that inhibits the binding). It is then determined if the compound has the above cell-stimulating activity mediated by the protein of the invention. The compound or its salt having the cell-stimulating activity is the agonist to the protein of the invention, whereas the compound or its salt having no such an activity is the antagonist to the protein of the invention.

(ii) (a) A test compound is brought in contact with a cell containing the protein of the invention, whereby the aforesaid cell-stimulating activity mediated by the protein of the invention is assayed. The compound having the cell-stimulating activity or its salt is the agonist to the protein of the invention.

(b) The cell-stimulating activity mediated by the protein of the invention is assayed in the case when a compound that activates the protein of the invention (e.g., the peptide of the invention or the agonist to the protein of the invention, etc.) is brought in contact with cells containing the protein of the invention and in the case when the compound that activates the protein of the invention and a test compound are brought in contact with cells containing the protein of the invention, and compared these cases. The compound or its salt that can reduce the cell-stimulating activity induced by the compound that activates the protein of the invention is the antagonist to the protein of the invention.

The agonists to the protein of the invention exhibit similar physiological activity of the peptide of the invention on the protein of the invention, and are thus safe and low-toxic drugs as in the peptide of the invention.

The antagonist to the protein of the invention can suppress the physiological activity that the peptide of the invention has on the protein of the invention, and are thus useful as safe and low-toxic drugs for suppressing the receptor activity.

As stated above, the peptide of the invention has an activity of preventing contraction of intestinal tracts, etc., and thus can be used as drugs for the treatment/prevention of digestive diseases (e.g., enteritis, diarrhea, constipation, malabsorption syndrome, etc.). Thus, in the compounds obtained using the screening method or the screening kit described above, the agonists to the protein of the invention (ZAQ agonists) can be used as drugs for the treatment/prevention of digestive diseases (e.g., enteritis, diarrhea, constipation, malabsorption syndrome, etc.), etc. Also, the antagonists to the protein of the invention (ZAQ antagonists) can be used as drugs for the treatment/prevention of digestive diseases (e.g., enteritis, diarrhea, constipation, malabsorption syndrome, etc.), etc.

The compound or its salt, which is obtainable using the screening method or the screening kit of the invention, is selected from, e.g., peptides, proteins, non-peptide compounds, synthetic compounds, fermentation products, cell extracts, plant extracts, animal tissue extracts, plasma, etc., and is the compound that promotes or inhibits the function of the peptide of the invention.

Preferred examples of the salts with inorganic bases include alkali metal salts such as sodium salts, potassium salts, etc.; alkaline earth metal salts such as calcium salts, magnesium salts, etc.; aluminum salts, ammonium salts, and the like.

Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc.

Preferred examples of the salts with inorganic acids include salts with hydrochloric acid, hydrobromic acid, sulfuric acid, phosphoric acid, etc.

Preferred examples of the salts with organic acids include salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid, etc.

Preferred examples of the salts with basic amino acids include salts with arginine, lysine, ornithine, etc. Preferred examples of the salts with acidic amino acids include salts with aspartic acid, glutamic acid, etc.

Where the compound or its salts, which are obtained by the screening methods or screening kits of the present invention, are used as the pharmaceutical compositions described above, they can be formulated as in the case where the aforesaid peptide of the invention are employed.

When the compound or its salts obtained by the screening methods or screening kits of the present invention are used as the above-mentioned pharmaceutical compositions, they can be formulated in a conventional manner. For example, they can be administered orally as tablets coated with sugar or with enteric coating if necessary, capsules, elixirs, microcapsules, etc., or parenterally in the form of injections such as sterile solutions or suspensions in water or in pharmaceutically acceptable solutions other than water. For example, the compound or its salts can be mixed with carriers, flavoring agents, excipients, vehicles, preservatives, stabilizers, binders, etc. in a unit dosage form required for generally accepted pharmaceutical practice to prepare pharmaceutical preparations. The amount of active ingredients in these preparations is adjusted so as to obtain appropriate doses within specified ranges.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of a capsule, liquid carriers such as oils and fats may further be used together with the additives described above. A sterile composition for injection may be formulated in a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate, benzyl alcohol, etc.

The prophylactic/therapeutic agent may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the pharmaceutical preparation thus obtained is safe and low toxic, it can be administered to human or another mammal (e.g., mouse, rat, guinea pig, rabbit, sheep, swine, bovine, cat, dog, monkey, chimpanzee, etc.).

The dose of the compound or its salt obtained by the screening methods or screening kits of the invention varies depending on its activity, target disease, subject to be administered, route for administration, etc.; when the compound is orally administered, the dose is normally about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. When adult patient (as 60 kg body weight) with digestive disease is administered in the form of injection, it is advantageous to administer the ZAQ antagonist intravenously to the patient generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

(3) Quantification of the Peptide of the Invention or its Salt

The antibody of the invention is capable of specifically recognizing the peptide of the invention and can be used for quantification of the peptide of the invention in a sample fluid, in particular, for quantification by sandwich immunoassay.

That is, the present invention provides:

(i) a method for quantification of the peptide of the invention in a sample fluid, which comprises competitively reacting the antibody of the invention with a sample fluid and a labeled form of the peptide of the invention, and measuring the ratio of the labeled peptide of the invention bound to said antibody; and, (ii) a method for quantification of the peptide of the invention in a sample fluid, which comprises simultaneously or continuously reacting the sample fluid with the antibody of the invention and a labeled form of another antibody of the invention immobilized on an insoluble carrier, and measuring the activity of the labeling agent on the immobilized carrier.

In the method (ii) described above, it is preferred that one antibody is capable of recognizing the N-terminal region of the peptide of the invention, while another antibody is capable of recognizing the C-terminal region of the peptide of the invention.

The monoclonal antibody to the peptide of the invention may be used to quantify the peptide of the invention. Moreover, the peptide of the invention may also be detected by means of a tissue staining, etc. For these purposes, the antibody molecule per se may be used, or $F(ab')_2$, Fab' or Fab fractions of the antibody molecule may be used as well.

The method of quantifying the peptide of the invention using the antibody of the invention is not particularly limited, and any method may be used so far as it relates to a method, in which the amount of an antibody, antigen or antibody-antigen complex can be detected by a chemical or a physical means, depending on or corresponding to the amount of antigen (e.g., the amount of the peptide of the invention) in a sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same, are radioisotopes, enzymes, fluorescent substances, luminescent substances, etc. Examples of radioisotopes are $[^{125}I]$, $[^{131}I]$, $[^{3}H]$, $[^{14}C]$, etc. Preferred examples of enzymes are those that are stable and have a high specific activity, which include β-galactosidase, β-glucosidase, alkaline phosphatase, peroxidase, malate dehydrogenase, etc. Examples of fluorescent substances are fluorescanine, fluorescein isothiocyanate, etc. Examples of luminescent substances are luminol, a luminol derivative, luciferin, lucigenin, etc. Furthermore, a biotin-avidin system may be used as well for binding an antibody or antigen to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, a sample fluid is reacted with an immobilized form of the monoclonal antibody of the invention (primary reaction), then reacted with a labeled form of the monoclonal antibody of the invention (secondary reaction) and the activity of the labeling agent on the insoluble carrier is assayed; thus, the amount of peptide of the invention in a sample fluid can be determined. The primary and secondary reactions may be carried out in a reversed order, simultaneously or sequentially with intervals. The type of the labeling agent and the method of immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the assay sensitivity, etc.

In the method of assaying the peptide of the invention by the sandwich method according to the present invention, preferred monoclonal antibodies of the present invention used for the primary and the secondary reactions are antibodies, which binding sites to the peptide of the invention are different from each other. Thus, the antibodies used in the primary and secondary reactions are those wherein, when the antibody used in the secondary reaction recognizes the C-terminal region of the peptide of the invention, the antibody recognizing the site other than the C-terminal regions, e.g., recognizing the N-terminal region, is preferably used in the primary reaction.

The monoclonal antibody of the invention may be used in an assay system other than the sandwich method, such as the competitive method, the immunometric method or the nephrometry.

In the competitive method, an antigen in a sample fluid and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the sample fluid. In the reactions for such a method, there are a liquid phase method in which a soluble antibody is used as the antibody and the B/F separation is effected by polyethylene glycol, while a second antibody to the antibody is used, and a solid phase method in which an immobilized antibody is used as the first antibody or a soluble antibody is used as the first antibody, while an immobilized antibody is used as the second antibody.

In the immunometric method, an antigen in a sample fluid and an immobilized antigen are competitively reacted with a given amount of a labeled antibody followed by separating the solid phase from the liquid phase; or an antigen in a sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the sample fluid.

In the nephrometry, the amount of insoluble sediment, which is produced as a result of the antigen-antibody reaction in a gel or in a solution, is measured. Even when the amount of an antigen in a sample fluid is small and only a small amount of the sediment is obtained, a laser nephrometry utilizing laser scattering can be suitably used.

In applying each of those immunoassays to the assay method of the present invention, any special conditions, operations, etc. are not required. The assay system for the peptide of the invention may be constructed in addition to conditions or operations conventionally used for each of the methods, taking technical consideration by one skilled in the art into account. For the details of such conventional technical means, a variety of reviews, reference books, etc. may be referred to:

For example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.

As described above, the peptide of the invention can be quantified with high sensitivity, using the antibody of the invention.

Furthermore, by quantifying a level of the peptide of the invention using the antibody of the invention (1) when an increased level of the peptide of the invention is detected, it can be diagnosed that one suffers from, digestive diseases (e.g., enteritis, diarrhea, constipation, malabsorption syndrome, etc.); or it is highly likely for one to suffer from this disease in the future. Also, (2) when a reduced level of the peptide of the invention is detected, it can be diagnosed that one suffers from, digestive diseases (e.g., enteritis, diarrhea, constipation, malabsorption syndrome, etc.); or it is highly likely for one to suffer from these disease in the future.

The antibody of the invention may also be employed to detect the peptide of the invention present in a sample fluid such as body fluids, tissues, etc. The antibody may further be used for the preparation of an antibody column used to purify the peptide of the invention, detect the peptide of the invention in each fraction upon purification, analysis of the behavior of the peptide of the invention in the cells under investigation.

(4) Gene Diagnostic Agent

By using the DNA of the present invention, e.g., as a probe, abnormality (gene abnormality) of the DNA or MRNA encoding the peptide of the invention in human or other warm-blooded animal (e.g., rat, mouse, guinea pig, rabbit, chicken, sheep, swine, bovine, horse, cat, dog, monkey, etc.) can be detected. Thus, the DNA of the present invention is useful as a gene diagnostic agent for the damage to the DNA or mRNA, mutation, a decreased expression or an increased expression, or overexpression of the DNA or mRNA.

The gene diagnosis described above using the DNA of the present invention can be performed by, for example, the publicly known Northern hybridization assay or the PCR-SSCP assay (Genomics, 5, 874–879 (1989); Proceedings of the National Academy of Sciences of the USA, 86, 2766–2770 (1989)).

When a decreased expression is detected, e.g., by the Northern hybridization or DNA micro array, it can be diagnosed that one is likely to suffer from, for example, digestive diseases (e.g., enteritis, diarrhea, constipation, malabsorption syndrome, etc.).

(5) Pharmaceutical Composition Comprising Antisense DNA

Since antisense DNA that binds complementarily to the DNA of the present invention and is capable of suppressing expression of the DNA can suppress the function of the peptide of the invention or the DNA of the present invention in vivo, the antisense DNA can be used as a preventive/therapeutic agent for diseases associated with overexpression of the peptide of the invention (for example, digestive diseases (e.g., enteritis, diarrhea, constipation, malabsorption syndrome, etc.)).

The antisense DNA described above can be used as the aforesaid therapeutic/prophylactic agent, similarly to the above-described drugs comprising the DNA of the present invention for the treatment/prevention of various diseases.

The antisense DNA may be administered alone; or after the DNA is inserted into an appropriate vector such as retrovirus vector, adenovirus vector, adenovirus-associated virus vector, etc., the DNA may be administered in a conventional manner. The antisense DNA may also be administered as intact DNA, or with adjuvants to assist its uptake by gene gun or through a catheter such as a catheter with a hydrogel.

In addition, the antisense DNA may also be employed as an oligonucleotide probe for diagnosis to detect the presence of the DNA of the present invention in tissues or cells and states of its expression.

(6) Pharmaceutical Composition Comprising the Antibody of the Invention

The antibody of the invention having the effect to neutralize the peptide of the invention can be used as preventive/therapeutic agents for diseases associated with overexpression of the peptide of the invention (for example, digestive diseases (e.g., enteritis, diarrhea, constipation, malabsorption syndrome, etc.)).

The therapeutic/preventive agents for diseases described above comprising the antibody of the invention can be administered to human or other warm-blooded animal (e.g., rat, rabbit, sheep, swine, bovine, cat, dog, monkey, etc.) orally or parenterally directly as a liquid preparation, or as a pharmaceutical composition in an appropriate preparation form. The dose varies depending on subject to be administered, target disease, conditions, route for administration, etc.; when it is used for the treatment/prevention of the adult patient with, e.g., digestive disease, the antibody of the invention is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The antibody of the invention may be administered directly as it is or in the form of an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), non-ionic surfactant [e.g., polysorbate 80, HCO-50 (polyoxyethylene (50 mol)

adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(7) Preparation of Non-human Animals Carrying the DNA of the Present Invention

Using the DNA of the present invention, non-human transgenic animals expressing the protein, etc. of the invention can be prepared. Examples of the non-human animals include mammals (e.g., rats, mice, rabbits, sheep, swine, bovine, cats, dogs, monkeys, etc.) (hereinafter merely referred to as animals) can be used, with mice and rabbits being particularly appropriate.

To transfer the DNA of the present invention to target animals, it is generally advantageous to use the DNA in a gene construct ligated downstream of a promoter that can express the DNA in animal cells. For example, when the DNA of the present invention derived from rabbit is transferred, e.g., the gene construct, in which the DNA is ligated downstream of a promoter that can expresses the DNA of the present invention derived from animals comprising the DNA of the present invention highly homologous to the rabbit-derived DNA, is microinjected to rabbit fertilized ova; thus, the DNA-transferred animal, which is capable of producing a high level of the protein, etc. of the invention, can be produced. Examples of the promoters that are usable include virus-derived promoters and ubiquitous expression promoters such as a metallothionein promoter, but promoters of NGF gene and enolase that are specifically expressed in the brain are preferably used.

The transfer of the DNA of the present invention at the fertilized egg cell stage secures the presence of the DNA in all germ and somatic cells in the produced animal. The presence of the protein, etc. of the invention in the germ cells in the DNA-transferred animal means that all germ and somatic cells comprise the protein, etc. of the invention in all progenies of the animal. The progenies of the animal that took over the gene comprise the protein, etc. of the invention in all germ and somatic cells.

The DNA-transferred animals of the present invention can be maintained and bled in the conventional environment as animals carrying the DNA after confirming the stable retention of the gene in the animals through mating. Furthermore, mating male and female animals comprising the objective DNA results in acquiring homozygote animals having the transferred gene on both homologous chromosomes. By mating the male and female homozygotes, bleeding can be performed so that all progenies comprise the DNA.

Since the protein, etc. of the invention is highly expressed in the animals in which the DNA of the present invention has been transferred, the animals are useful for screening of agonists or antagonists to the protein, etc. of the invention.

The animals in which the DNA of the present invention has been transferred can also be used as cell sources for tissue culture. The protein, etc. of the invention can be analyzed by, for example, directly analyzing the DNA or RNA in tissues from the mouse in which the DNA of the present invention has been transferred, or by analyzing tissues comprising the protein expressed from the gene. Cells from tissues comprising the protein, etc. of the invention are cultured by the standard tissue culture technique. Using these cells, for example, the function of tissue cells such as cells derived from the brain or peripheral tissues, which are generally difficult to culture, can be studied. Using these cells, for example, it is possible to select pharmaceuticals that increase various tissue functions. When a highly expressing cell line is available, the protein, etc. of the invention can be isolated and purified from the cell line.

(8) Utility, etc. of the Peptide of the Invention

The method of screening the compound or its salt that alters the binding property between the peptide of the invention and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, or its salt, which comprises using the peptide of the invention and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, its partial peptide or a salt thereof, can be implemented in a manner similar to the screening method of the invention described in (2) above.

The kit for screening the compound or its salt that alters the binding property between the peptide of the invention and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, or its salt, comprising the peptide of the invention and the protein containing the same or substantially the same amino acid sequence as the amino acid sequence represented by SEQ ID NO: 36, SEQ ID NO: 40,SEQ ID NO: 47, SEQ ID NO: 48 or SEQ ID NO: 49, its partial peptide or a salt thereof, can be implemented in a manner similar to the screening kit of the invention described in (2) above.

The method of screening the compound or its salt that alters the binding property between the peptide containing the same or substantially the same amino acid sequence as the amino acid sequence represented by SEQ ID NO: 34 or its salt and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, or its salt, which comprises using the peptide of the invention and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, its partial peptide or a salt thereof, can be implemented in a manner similar to the screening method of the invention described in (2) above.

The kit for screening the compound or its salt that alters the binding property between the peptide containing the same or substantially the same amino acid sequence as the amino acid sequence represented by SEQ ID NO: 34 or its salt and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, or its salt, comprising the peptide of the invention and the protein containing the same or substantially the same amino acid sequence as the amino acid sequence represented by SEQ ID NO: 36, SEQ ID NO: 40, SEQ ID NO: 47, SEQ ID NO: 48 or SEQ ID NO: 49, its partial peptide or a salt thereof, can be implemented in a manner similar to the screening kit of the invention described in (2) above.

The compound or its salt, which is obtainable using the screening methods or screening kits described above, can be used in a manner similar to the compound or its salt, which is obtainable using the screening methods or screening kits described in (2) above.

In the specification and drawings, the codes of bases and amino acids are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA: | deoxyribonucleic acid |
| cDNA: | complementary deoxyribonucleic acid |
| A: | adenine |
| T: | thymine |
| G: | guanine |
| C: | cytosine |
| Y: | thymine or cytosine |
| N: | thymine, cytosine, adenine or guanine |
| R: | adenine or guanine |
| M: | cytosine or adenine |
| W: | thymine or adenine |
| S: | cytosine or guanine |
| RNA: | ribonucleic acid |
| mRNA: | messenger ribonucleic acid |
| dATP: | deoxyadenosine triphosphate |
| dTTP: | deoxythymidine triphosphate |
| dGTP: | deoxyguanosine triphosphate |
| dCTP: | deoxycytidine triphosphate |
| ATP: | adenosine triphosphate |
| Gly or G: | glycine |
| Ala or A: | alanine |
| Val or V: | valine |
| Leu or L: | leucine |
| Ile or I: | isoleucine |
| Ser or S: | serine |
| Thr or T: | threonine |
| Cys or C: | cysteine |
| Met or M: | methionine |
| Glu or E: | glutamic acid |
| Asp or D: | aspartic acid |
| Lys or K: | lysine |
| Arg or R: | arginine |
| His or H: | histidine |
| Phe or F: | phenylalanine |
| Tyr or Y: | tyrosine |
| Trp or W: | tryptophan |
| Pro or P: | proline |
| Asn or N: | asparagine |
| Gln or Q: | glutamine |
| pGlu: | pyroglutamic acid |
| Xaa: | unidentified amino acid residue |

Also, the substituents, protecting groups, reagents, etc. frequently employed in the specification are designated by the following symbols.

| | |
|---|---|
| Me: | methyl group |
| Et: | ethyl group |
| Bu: | butyl group |
| Ph: | phenyl group |
| TC: | thiazolidine-4(R)-carboxamide group |
| Bom: | benzyloxymethyl |
| Bzl: | benzyl |
| Z: | benzyloxycarbonyl |
| Br-Z: | 2-bromobenzyloxycarbonyl |
| Cl-Z: | 2-chlorobenzyloxycarbonyl |
| $Cl_2Bzl$: | 2,6-dichlorobenzyl |
| Boc: | t-butyloxycarbonyl |
| HOBt: | 1-hydroxybenztriazole |
| HOOBt: | 3,4-dihydro-3-hydroxy-4-oxo-1,2,3-benzotriazine |
| PAM: | phenylacetamidomethyl |
| Tos: | p-toluenesulfonyl |
| Fmoc: | N-9-fluorenylmethoxycarbonyl |
| DNP: | dinitrophenyl |
| Bum: | tertiary-butoxymethyl |
| Trt: | trityl |
| Bom: | benzyloxymethyl |
| Z: | benzyloxycarbonyl |
| MeBzl: | 4-methylbenzyl |
| DCC: | N,N'-dicyclohexylcarbodiimide |
| HONB: | 1-hydroxy-5-norbornene-2,3-dicarboxyimide |
| NMP: | N-methylpyrrolidone |
| HONB: | N-hydroxy-5-norbornene-2,3-dicarboxyimide |
| NMP: | N-methylpyrrolidone |
| TFA: | trifluoroacetic acid |
| CHAPS: | 3-[(3-cholamidopropyl)dimethylammonio]-1-propanesulfonate |
| PMSF: | phenylmethylsulfonyl fluoride |
| GDP: | guanosine-5'-diphosphate |
| Fura-2AM: | pentacetoxymethyl 1-[6-amino-2-(5-carboxy-2-oxazolyl)-5-benzofuranyloxy]-(2-amino-5-methylphenoxyl)-ethane-N,N,N',N'-tetraacetate |
| Fluo-3AM: | pentacetoxymethyl 1-[2-amino-5-(2,7-dichloro-6-hydroxy-3-oxy-9-xanthenyl)phenoxy]-2-(2-amino-5-methylphenoxy)-ethane-N,N,N',N'-tetraacetate |
| HEPES: | 2-[4-(2-hydroxyethyl)-1-piperazinyl]ethanesulfonic acid |
| EDTA: | ethylenediaminetetraacetic acid |
| SDS: | sodium dodecyl sulfate |
| BSA: | bovine serum albumin |
| HBSS: | Hanks' balanced salt solution |
| EIA: | enzymeimmunoassay |

The sequence identification numbers in the sequence listing of the specification indicates the following sequences, respectively.

[SEQ ID NO: 1]

This shows the amino acid sequence of the protein of the invention derived from human brain.

[SEQ ID NO: 2]

This shows the base sequence of DNA encoding the protein of the invention derived from human brain containing the amino acid sequence represented by SEQ ID NO:1 (ZAQC).

[SEQ ID NO: 3]

This shows the base sequence of DNA encoding the protein of the invention derived from human brain containing the amino acid sequence represented by SEQ ID NO:1 (ZAQT).

[SEQ ID NO: 4]

This shows the base sequence of primer 1 used in EXAMPLE 1 later described.

[SEQ ID NO: 5]

This shows the base sequence of primer 2 used in EXAMPLE 1 later described.

[SEQ ID NO: 6]

This shows the base sequence of primer 3 used in EXAMPLE 2 later described.

[SEQ ID NO: 7]
This shows the base sequence of primer 4 used in EXAMPLE 2 later described.

[SEQ ID NO: 8]
This shows the base sequence of ZAQ probe used in EXAMPLE 2 later described.

[SEQ ID NO: 9]
This shows the base sequence of primer ZAQC Sal used in EXAMPLE 2 later described.

[SEQ ID NO: 10]
This shows the base sequence of primer ZAQC Spe used in EXAMPLE 2 later described.

[SEQ ID NO: 11]
This shows the N-terminal amino acid sequence of ZAQ activated peptide purified in EXAMPLE 3 (3–8) later described.

[SEQ ID NO: 12]
This shows the base sequence of primer ZF1 used in EXAMPLE 4 later described.

[SEQ ID NO: 13]
This shows the base sequence of primer ZF2 used in EXAMPLE 4 later described.

[SEQ ID NO: 14]
This shows the base sequence of primer ZF3 used in EXAMPLE 4 later described.

[SEQ ID NO: 15]
This shows the 3'-terminal base sequence of DNA encoding human type ZAQ ligand peptide acquired in EXAMPLE 4 later described.

[SEQ ID NO: 16]
This shows the base sequence of primer ZAQL-CF used in EXAMPLE 4 later described.

[SEQ ID NO: 17]
This shows the base sequence of primer ZAQAL-XR1 used in EXAMPLE 4 later described.

[SEQ ID NO: 18]
This shows the base sequence of the DNA fragment obtained in EXAMPLE 4 later described.

[SEQ ID NO: 19]
This shows the base sequence of the DNA fragment obtained in EXAMPLE 4 later described.

[SEQ ID NO: 20]
This shows the amino acid sequence of human type ZAQ ligand mature peptide.

[SEQ ID NO: 21]
This shows the amino acid sequence of human type ZAQ ligand mature peptide.

[SEQ ID NO: 22]
This shows the amino acid sequence of human type ZAQ ligand precursor peptide.

[SEQ ID NO: 23]
This shows the amino acid sequence of human type ZAQ ligand precursor peptide.

[SEQ ID NO: 24]
This shows the base sequence of DNA which contains the DNA encoding human type ZAQ ligand precursor peptide represented by SEQ ID NO: 28.

[SEQ ID NO: 25]
This shows the base sequence of DNA which contains the DNA encoding human type ZAQ ligand precursor peptide represented by SEQ ID NO: 29.

[SEQ ID NO: 26]
This shows the base sequence of DNA encoding human type ZAQ ligand mature peptide represented by SEQ ID NO: 20.

[SEQ ID NO: 27]
This shows the base sequence of DNA encoding human type ZAQ ligand mature peptide represented by SEQ ID NO: 21.

[SEQ ID NO: 28]
This shows the base sequence of DNA encoding human type ZAQ ligand precursor peptide represented by SEQ ID NO: 22.

[SEQ ID NO: 29]
This shows the base sequence of DNA encoding human type ZAQ ligand precursor peptide represented by SEQ ID NO: 23.

[SEQ ID NO: 30]
This shows the base sequence of DNA fragment obtained in EXAMPLE 5 (5–1) later described.

[SEQ ID NO: 31]
This shows the N-terminal amino acid sequence of human type ZAQ ligand peptide analyzed in EXAMPLE 6 (6–2) later described.

[SEQ ID NO: 32]
This shows the base sequence of the primer used in EXAMPLE 7 later described.

[SEQ ID NO: 33]
This shows the base sequence of the primer used in EXAMPLE 7 later described.

[SEQ ID NO: 34]
This shows the amino acid sequence of snake venom MIT1 purified in EXAMPLE 8 later described.

[SEQ ID NO: 35]
This shows the base sequence of cDNA encoding human type I5E receptor protein.

[SEQ ID NO: 36]
This shows the amino acid sequence of human type I5E receptor protein.

[SEQ ID NO: 37]
This shows the base sequence of the primer used in EXAMPLE 9 later described.

[SEQ ID NO: 38]
This shows the base sequence of the primer used in EXAMPLE 9 later described.

[SEQ ID NO: 39]
This shows the base sequence of cDNA encoding novel G protein-coupled receptor protein (rZAQ1).

[SEQ ID NO: 40]
This shows the amino acid sequence of novel G protein-coupled receptor protein (rZAQ 1).

[SEQ ID NO: 41]
This shows the base sequence of the primer used in EXAMPLE 10 later described.

[SEQ ID NO: 42]

This shows the base sequence of the primer used in EXAMPLE 10 later described.

[SEQ ID NO: 43]
This shows the base sequence of the primer used in EXAMPLE 10 later described.

[SEQ ID NO: 44]
This shows the base sequence of the primer used in EXAMPLE 10 later described.

[SEQ ID NO: 45]
This shows the base sequence of the primer used in EXAMPLE 10 later described.

[SEQ ID NO: 46]
This shows the base sequence of cDNA encoding the novel G protein-coupled receptor protein (rZAQ2).

[SEQ ID NO: 47]
This shows the amino acid sequence of the novel G protein-coupled receptor protein (rZAQ2).

[SEQ ID NO: 48]
This shows the amino acid sequence of mouse-derived G protein-coupled receptor protein (GPR73).

[SEQ ID NO: 49]
This shows the amino acid sequence of mouse-derived G protein-coupled receptor protein (mI5E).

[SEQ ID NO: 50]
This shows the base sequence of cDNA encoding mouse-derived G protein-coupled receptor protein (GPR73).

[SEQ ID NO: 51]
This shows the base sequence of cDNA encoding mouse-derived G protein-coupled receptor protein (mI5E).

[SEQ ID NO: 52]
This shows the base sequence of DNA fragment #1 used in REFERENCE EXAMPLE 1.

[SEQ ID NO: 53]
This shows the base sequence of DNA fragment #2 used in REFERENCE EXAMPLE 1.

[SEQ ID NO: 54]
This shows the base sequence of DNA fragment #3 used in REFERENCE EXAMPLE 1.

[SEQ ID NO: 55]
This shows the base sequence of DNA fragment #4 used in REFERENCE EXAMPLE 1.

[SEQ ID NO: 56]
This shows the base sequence of DNA fragment #5 used in REFERENCE EXAMPLE 1.

[SEQ ID NO: 57]
This shows the base sequence of DNA fragment #6 used in REFERENCE EXAMPLE 1.

[SEQ ID NO: 58]
This shows the base sequence of synthetic DNA encoding human type ZAQ ligand represented by SEQ ID NO: 21.

Transformant *Escherichia coli* DH5α/pCR2.1-ZAQC obtained in EXAMPLE 1 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)), located at Central 6, 1-1-1 Higashi, Tsukuba, Ibaraki, Japan, under the Accession Number FERM BP-6855 since Aug. 23, 1999 and with the Institute for Fermentation, Osaka (IFO), located at 2-17-85, Juso-honmachi, Yodogawa-ku, Osaka-shi, Osaka, Japan, under the Accession Number IFO 16301 since Aug. 4, 1999.

Transformant *Escherichia coli* DH5α/pCR2.1-ZAQT obtained in EXAMPLE 1 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)) under the Accession Number FERM BP-6856 since Aug. 23, 1999 and with Institute for Fermentation, Osaka (IFO) under the Accession Number IFO 16302 since Aug. 4, 1999.

Transformant *Escherichia coli* TOP10/pHMITA obtained in EXAMPLE 4 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)) under the Accession Number FERM BP-7219 since Jul. 13, 2000 and with Institute for Fermentation, Osaka (IFO) under the Accession Number IFO 16440 since May 26, 2000.

Transformant *Escherichia coli* TOP10/pHMITG obtained in EXAMPLE 4 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)) under the Accession Number FERM BP-7220 since Jul. 13, 2000 and with Institute for Fermentation, Osaka (IFO) under the Accession Number IFO 16441 since May 26, 2000.

Transformant *Escherichia coli* DH5α/pCR2.1-rZAQ1 obtained in EXAMPLE 9 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)) under the Accession Number FERM BP-7275 since Aug. 21, 2000 and with Institute for Fermentation, Osaka (IFO) under the Accession Number IFO 16459 since Aug. 1, 2000.

Transformant *Escherichia coli* DH10B/pCMV-rZAQ2 obtained in EXAMPLE 10 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)) under the Accession Number FERM BP-7276 since Aug. 21, 2000 and with Institute for Fermentation, Osaka (IFO) under the Accession Number IFO 16460 since Aug. 1, 2000.

Transformant *Escherichia coli* MM294 (DE3)/pTCh1ZAQ obtained in REFERENCE EXAMPLE 1 later described has been on deposit with National Institute of Advanced Industrial Science and Technology, International Patent Organism Depositary under the Accession Number FERM BP-7571 since Apr. 27, 2001 and with Institute for Fermentation, Osaka (IFO) under the Accession Number IFO 16527 since Jan. 16, 2001.

EXAMPLES

Hereinafter, the present invention is described in detail with reference to EXAMPLES and REFERENCE EXAMPLES, but is not deemed to limit the scope of the present invention thereto. The gene manipulation procedures using *Escherichia coli* were performed according to the methods described in the Molecular Cloning.

Example 1

Cloning of cDNA Encoding the G Protein-coupled Receptor Protein ZAQ and Determination of the Base Sequence Using human pituitary cDNA (CLONTECH Laboratories, Inc.) as a template and two primers, namely, primer 1 (5'-GTC GAC ATG GAG ACC ACC ATG GGG TTC ATG G- 3'; SEQ ID NO:4) and primer 2 (5'-ACT AGT TTA TTT TAG TCT GAT GCA GTC CAC CTC TTC -3'; SEQ ID NO:5), PCR was carried out. The reaction solution in the above reaction was composed of 1/10 volume of the cDNA described above, 1/50 volume of Advantage 2 Polymerase Mix (CLONTECH Laboratories, Inc.), 0.2 µM of primer 1, 0.2 µM of primer 2, 200 µM dNTPs and a buffer supplied with the enzyme to make the final volume 25 µl. In the PCR, after the reaction solution was heated at 94° C. for 2 minute, a cycle set at 94° C. for 20 seconds followed by 72° C. for 100 seconds was repeated 3 times, a cycle set at 94° C. for 20 seconds and at 68° C. for 100 seconds was repeated 3 times, a cycle set at 94° C. for 20 seconds; at 64° C. for 20 seconds and at 68° C. for 100 seconds was repeated 38 times, and finally, an extension reaction was carried out at 68° C. for 7 minutes. After completion of the PCR, the reaction product was subcloned to plasmid vector pCR2.1 (Invitrogen, Inc.) according to the instructions attached to the TA cloning kit (Invitrogen, Inc.). Then, it was introduced into *Escherichia coli* DH5α, and the clones bearing the cDNA were selected in LB agar medium containing ampicillin. The sequence of each clone was analyzed to give two cDNA sequences encoding novel G protein-coupled receptor protein, i.e., ZAQC (SEQ ID NO: 2) and ZAQT (SEQ ID NO: 3). The proteins having the amino acid sequence deduced from this cDNA were designated ZAQ since they all have the same amino acid sequence (SEQ ID NO:1). The transformant bearing the DNA represented by SEQ ID NO: 2 was named *Escherichia coli* DH5α/pCR2.1-ZAQC, and the transformant bearing the DNA represented by SEQ ID NO: 3 was named Escherichia coli DH5α/pCR2.1-ZAQT.

Example 2

Analysis of Expression Distribution of ZAQ by Taqman PCR

Primers and a probe to be used in Taqman PCR were surveyed using Primer Express Ver.1.0 (PE Biosystems Japan), and primer 3 (5'-TCATGTTGCTCCACTG-GAAGG-3' (SEQ ID (NO: 6)), primer 4 (5'-CCAAT-TGTCTTGAGGTCCAGG-3'(SEQ ID NO: 7)) and ZAQ probe (5'-TTCTTACAATGGCGGTAAGTCCAGTGCAG-3' (SEQ ID NO: 8)) were selected. FAM (6-carboxyfluorescein) was added as a reporter dye for the probe.

The PCR fragment, which was amplified using pAK-ZAQC as a template, and primer ZAQC Sal (5'-GTCGA-CATGGAGACCACCATGGGGTTCATGG -3' (SEQ ID NO: 9)) and primer ZAQC Spe (5'-ACTAGTTTATTT-TAGTCTGATGCAGTCCACCTCTTC-3' (SEQ ID NO: 10)), was purified with CHROMA SPIN200 (CLONTECH Laboratories, Inc. (CA,USA)), and then adjusted to have a concentration of $10^0$–$10^6$ copies/µl for usage as a standard DNA. Human Multiple Tissue cDNA Panel I and Panel II (CLONTECH Laboratories', Inc.) were used as the cDNA source for each tissue. To the primers, probe and template, Taqman Universal PCR Master Mix (PE Biosystems Japan) was added in the amount given by the attached instructions, and then PCR and analysis were performed with ABI PRISM 7700 Sequence Detection System (PE Biosystems Japan).

Figure 8:
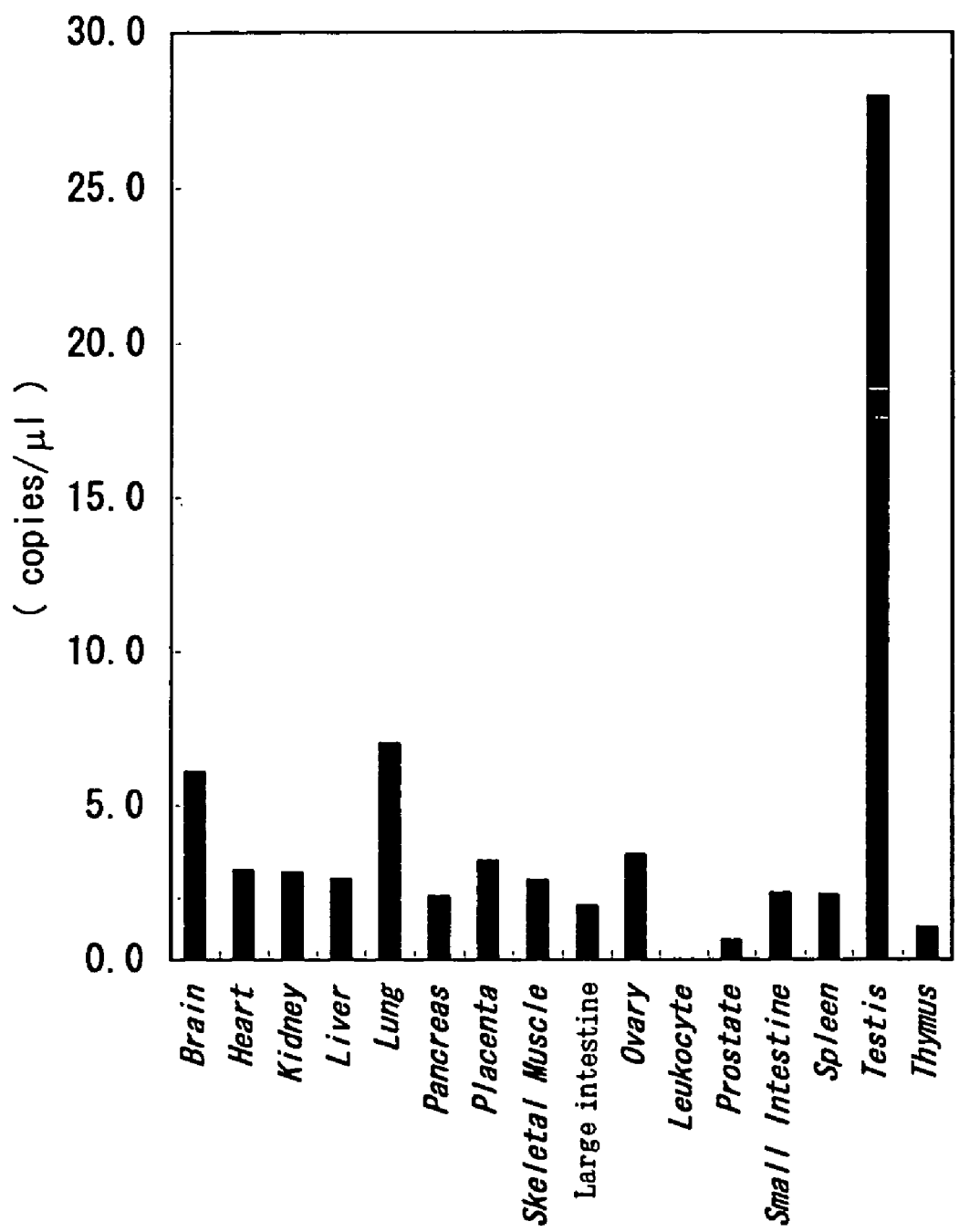
FIG. 8 shows the results of expression distribution analysis of ZAQ, which was carried out in EXAMPLE 2.

The results are shown in FIG. 8 and TABLE 1. The expression of ZAQ was found mainly in the testis, and next in the sites such as lung, brain and others.

TABLE 1

| Tissue | ZAQ (copies µl) |
| --- | --- |
| Brain | 6.1 |
| Heart | 2.9 |
| Kidney | 2.8 |
| Liver | 2.6 |
| Lung | 7.0 |
| Pancreas | 2.1 |
| Placenta | 3.2 |
| Skeletal muscle | 2.6 |
| Large intestine | 1.8 |
| Ovary | 3.4 |
| Leukocyte | 0.0 |
| Prostate | 0.7 |
| Small intestine | 2.2 |
| Spleen | 2.1 |
| Testis | 28.0 |
| Thymus | 1.1 |

Example 3

Isolation of ZAQ-activating Peptide (3–1) Preparation of Milk Extract Solution

Using commercially available milk, which was pasteurized at a low temperature, the following procedures were performed to prepare an extract solution. Two litters of milk were centrifuged at 10,000 rpm for 15 minutes at 4° C. with a high-speed centrifuge (CR26H, R10A rotor: Hitachi, Ltd.). The obtained supernatant was filtered through gauze to remove lipids. Acetic acid was added to the supernatant to adjust the concentration at final concentration of IM, and the mixture was agitated for 30 minutes at 4° C. Then, the mixture was centrifuged at 10,000 rpm for 15 minutes with a high-speed centrifuge (CR26H R10A rotor: Hitachi System Engineering Co., Ltd.). The obtained supernatant was filtered to remove insoluble matters. While agitating, acetone was added thereto as twice as much volume of the supernatant. Agitation was continued at 4° C. for 3 hours. Next, the mixture was centrifuged at 10,000 rpm for 15 minutes with a high-speed centrifuge (CR26H R10A rotor: Hitachi, Ltd.). The obtained supernatant was filtered to remove insoluble matters. The obtained supernatant was applied to a rotary evaporator to remove acetone and concentrated into 1350 ml at final volume. Then, 675 ml each of the resulting concentrate was mixed with 338 ml of diethyl ether and the mixture was vigorously shaken in a separatory funnel to separate into two phases to collect the aqueous phase. The same procedure was repeated once with respect to the aqueous phase obtained to give a clear aqueous solution. The aqueous solution obtained was concentrated to 800 ml using a rotary evaporator to give a final extract.

(3-2) Rough Fractionation of the Milk Extract Solution Using C18 Reversed Phase Chromatography Methanol was added into 10 g of a Sep-Pak C18 (Waters) column packed with octadecyl group-fixed silica gel to swell the gel. The column was then equilibrated with 1 M acetic acid. The extract solution prepared in (3-1) (the extract solution from 2-litter of milk) was loaded onto the column. Then, 100 ml of 1 M acetic acid was passed through the column to wash the gel. Next, the column was eluted with 200 ml of 60% acetonitrile/0.1% trifluoroacetic acid to elute the desired crude peptide component. After the obtained eluate was concentrated using a rotary evaporator, the concentrate was lyophilized with a freeze dryer (12EL; VirTis).

(3-3) Crude Fractionation of the Milk Extract Solution by Sulfopropyl Ion Exchange Chromatography SP Sephadex C-25 (Amersham Pharmacia Biotech) swollen in 100 mM HCl, was loaded onto a polypropylene-made column in a volume of 2 ml. The column was washed with distilled water and ammonium formate (pH 4.0) and equilibrated with eluent I (2 M ammonium formate:acetonitrile:water=1:25:74). The lyophilized product obtained in (3-2) was dissolved in 20 ml of eluent I. The resulting solution was loaded onto 2 ml of SP Sephadex C-25. After the column was washed with 10 ml of eluent I, the peptide was eluted with 10 ml each of eluent II (2 M ammonium formate:acetonitrile:water=1:2.5:6.5), eluent III (2M ammonium formate:acetonitrile:water=1:1:2) and eluent IV (2M ammonium formate:acetonitrile water=1:0.5:0.5) in this order. Each of Eluates I through IV was lyophilized with a freeze dryer (12EL; VirTis).

(3-4) Fractionation of the Milk Extract by TSKgel ODS80Ts Reversed Phase High Performance Liquid Chromatography By passing 91.7 vol % of eluent A (0.1% trifluoroacetic acid/distilled water) and 8.3 vol % of eluent B (0.1% trifluoroacetic acid/60% acetonitrile) through a column for TSKgel ODS80Ts reversed phase high performance liquid chromatography (Toso Co., Ltd., 4.6 mm×25 cm) at a flow rate of 1 ml/min at 40° C., the column was equilibrated. The lyophilized products of Eluates I through IV obtained in (3–3) were dissolved in 4 ml of 1 M acetic acid, and then subjected to chromatography treatment. That is, 4 ml of the solution of the lyophilized product was loaded onto the said column, and the concentration of eluent B was increased to 67 vol % of eluent A/33 vol % of eluent B over 1 minute and then increased with a linear gradient from 67 vol % of eluent A/33 vol % of eluent B to 0 vol % of eluent A/100 vol % of eluent B over next 40 minutes, at a flow rate of 1 ml/min.

The eluate was taken out by 1 ml each, giving a fraction number to each fraction, and 2 µl of each fraction was mixed with 150 µl of 0.2% bovine serum albumin (BSA)/distilled water, followed by lyophilization. The lyophilized product was used as an assay sample for measuring the intracellular $Ca^{2+}$ ion concentration increasing activity later described in (3-5).

(3-5) Measurement of the Intracellular $Ca^{2+}$ Ion Concentration Increasing Activity Using FLIPR The cell line capable of stably expressing ZAQ was prepared as follows. That is, one clone of DH5α/pCR2.1-ZAQC obtained in EXAMPLE 1 was incubated in LB medium supplemented with ampicillin while vigorously shaking to give plasmid pCR2.1-ZAQC. The plasmid was digested with restriction enzymes Sal I and Spe I to excise the insert part encoding ZAQC. Then, pAKKO-1.11H (Biochemica et Biophysica Acta, 1219 (1994) 251–259) similarly digested with restriction enzymes Sal I and Spe I was ligated with the insert part using Ligation Express Kit (CLONTECH Laboratories, Inc. (CA, USA)), which was transfected to E. coli DH10B by the electroporation method. The structure of the plasmid contained in the obtained clone was analyzed by restriction enzyme treatment and sequencing analysis. The plasmid correctly constructed was used as plasmid pAK-ZAQC for CHO cell expression.

This plasmid pAK-ZAQC was transfected to CHO/dhfr⁻ cell (American Type Culture Collection) using CellPhect Transfection Kit (Amersham Pharmacia Biotech). First, 120 µl of Buffer A (CellPhect Transfection Kit) was added to a solution of 4 µg of plasmid DNA in 120 µl of distilled water and the mixture was agitated. After allowing to stand for 10 minutes, 240 µl of Buffer B (CellPhect Transfection Kit) was added to the mixture. The mixture was vigorously agitated to form the DNA-calcium phosphate complex containing the said DNA. CHO/dhfr⁻ cells of $5 \times 10^5$ were inoculated on a 60 mm Petri dish. After incubation in Ham's F-12 medium (Nissui Pharmaceutical Co., Ltd.) supplemented with 10% fetal bovine serum (BIO WHITTAKER, Inc.) at 37° C. under 5% $CO_2$ for one day, 480 µl of a suspension of the DNA-calcium phosphate complex was dropwise added to the cells on the Petri dish. After incubation at 37° C. under 5% $CO_2$ for 6 hours, the cells were washed twice with serum-free Ham's F-12 medium, and 1.2 ml of buffer (140 mM NaCl, 25 mM HEPES, 1.4 mM $Na_2HPO_4$, pH7.1) supplemented with 15% glycerol was added to the cells on the dish to treat the cells for 2 minutes. The cells were again washed twice with serum-free Ham's F-12 medium, followed by incubation in Ham's F-12 medium containing 10% fetal bovine serum at 37° C. under 5% $CO_2$ overnight. The cells were treated with trypsin for dispersion, recovered from the dish, and were inoculated by $2 \times 10^4$ each in a 6-well plate. Incubation was initiated in Dulbecco's Modified Eagle Medium (DMEM) supplemented with 10% dialyzed fetal bovine serum (JRH BIOSCIENCES), 1 mM of MEM non-essential amino acid solution (Dainippon Pharmaceutical Co., Ltd.), 100 units/ml of penicillin and 100 µg/ml of streptomycin at 37° C. under 5% $CO_2$. The transformed CHO cells, into which the plasmid was introduced, were able to survive in the medium but non-tranfected cells died gradually. Thus, the medium was exchanged to remove the dead cells every 2 other days after the initiation of incubation. About 21 colonies of the transformed CHO cells grown after 8 to 10 days of the incubation were selected. RNA was recovered from each of the selected cells using a commercially available RNA isolation kit, followed by the RT-PCR method publicly known to select ZAQ expression CHO cell B-1 clone (hereinafter merely referred to as ZAQC-B1 cell), showing high expression of ZAQ.

For control, ETA (endothelin A receptor)-expressing CHO cell No. 24 clone (hereinafter simply referred to as ETA24 cell; see Journal of Pharmacology and Experimental Therapeutics, 279, 675–685,1996) was used.

The intracellular $Ca^{2+}$ ion concentration increasing activity of ZAQC-B1 cells or ETA24 cells was assayed for the samples obtained in (3-4) above using the FLIPR (Molecular Devices, Inc.). The ZAQC-B1 cells and ETA24 cells, which were both subcultured in DMEM medium supplemented with 10% dialyzed fetal bovine serum (hereinafter referred to as dFBS), were used. The ZAQC-B1 cells and ETA24 cells were suspended, respectively, in the medium (10% dFBS-DMEM) to adjust the concentration to $15 \times 10^4$ cells/ml. A 200 µl aliquot of each cell suspension was inoculated onto each well ($3.0 \times 10^4$ cells /200 µl/well) in a 96-well plate for FLIPR (Black Plate Clear Bottom, Coster), which was incubated in an incubator at 37° C. under 5% $CO_2$ overnight, and the cells thus obtained were used (hereinafter referred as to the cell plate). Twenty milliliters of H/HBS (9.8 g of Nissui Hanks 2 (Nissui Pharmaceutical Co., Ltd., 0.35 g of sodium hydrogencarbobonate, 4.77 g of HEPES, adjusted to pH 7.4 with a sodium hydroxide solution followed by sterilization through a sterilizing filter), 200 µl of 250 mM Probenecid, and 200 µl of fetal bovine serum (FBS) were mixed. Also, 2 vials (50 pg) of Fluo 3-AM (Dojin Chemical Research Institute) were dissolved in 40 µl of dimethylsulfoxide and 40 µl of 20% Pluronic acid (Molecular Probes, Inc.), and the resulting solution was added to the above H/HBSS-Probenecid-FBS mixture. After mixing, the medium was removed from the cell plate, and 100 µl each of the mixture was dispensed into each well of the cell plate using an 8-channel pipette. The cell plate was then incubated at 37° C. under 5% $CO_2$ for an hour (dye loading). For the assay samples obtained in EXAMPLE (3-4) described above, 150 µl of H/HBSS containing 2.5 mM Probenecid and 0.1% CHAPS was added to each fraction for dilution. The dilution was transferred to a 96-well plate for FLIPR (V-Bottom Plate, Coster, hereinafter referred as to the sample plate). After completion of the dye loading onto the cell plate, the cell plate was washed 4 times with the wash buffer composed of H/HBSS supplemented with 2.5 mM Probenedid, using a plate washer (Molecular Devices, Inc.). After washing, 100 µl of the wash buffer was saved for further procedures. This cell plate and the sample plate were set on FLIPR to conduct an assay (by FLIPR, 50 µl of the sample was transferred from the sample plate to the cell plate).

As a result, the intracellular $Ca^{2+}$ ion concentration increasing activity specific to ZAQC-B1 cells was found in fraction No. 53 that was fractionated by applying eluent IV (3-3) described above to the reversed phase high performance liquid chromatography in (34) above.

(3-6) Purification Using TSKgel Super-Phenyl Reversed Phase High Performance Liquid Chromatography (1) By passing 91.7 vol % of eluent A (0.1% trifluoroacetic acid/distilled water)/8.3 vol % of eluent B (0.1% trifluoroacetic acid/60% acetonitrile) through a column for TSKgel Super-Phenyl reversed phase high performance liquid chromatography (Toso Co., Ltd., 0.46 cm×10 cm) at a flow rate of 1 ml/min at 40° C., the column was equilibrated. Fraction No. 53 obtained in (3-4) described above was subjected to chromatography. That is, 1 ml of fraction No. 53 was loaded onto the column, and the concentration of eluent B was increased to 75 vol % of eluent A/25 vol % of eluent B over 1 minute and then increased with a linear gradient to 67 vol % of eluent A/33 vol % of eluent B over 75 minutes, at a flow rate of 1 ml/min.

The eluate was taken out by 500 µl each, giving a fraction number to each fraction, and 25 µl of each fraction fractionated was mixed with 150 µl of 0.2% BSA, followed by lyophilization with a freeze dryer (12EL; VirTis). The lyophilized product was added with 150 µl of H/HBS S containing 2.5 mM Probenecid and 0.1% CHAPS to dissolve the lyophilized product. By using 50 µl of the resulting solution, the intracellular $Ca^{2+}$ ion concentration increasing activity was measured by the method described in (3-5) above, thereby to assay the effect of activating the receptor to ZAQC-B1 cells. The result revealed that the component having the effect of activating the receptor to the objective ZAQC-B1 cells, i.e., the ZAQ activating component, was eluted mainly in fraction Nos. 103–105.

(3-7) Purification Using µRPC C2/C18 ST4.6/100 Reversed Phase High Performance Liquid Chromatography By passing 95 vol % of eluent A (heptafluorobytyric acid/distilled water)/5 vol % of eluent B (0.1% heptafluorobutyric acid/100% acetonitrile) through a column for µRPC C2/C18 ST4.6/100 reversed high performance liquid chromatography (Amersham Pharmacia Biotech, 0.46 cm×10 cm) at a flow rate of 1 ml/min at 40° C., the column was equilibrated.

After Fractions Nos. 103–105 selected from the fractions obtained in (3-6) above by TSKgel Super-Phenyl reversed phase high performance liquid chromatography were directly loaded onto µRPC C2/C18 ST4.6/100 reversed phase column, elution was conducted by quickly increasing from 95 vol % of eluent A (0.1% heptafluorobutyric acid/distilled water)/5 vol % of eluent B (0.1% heptafluorobutyric acid/100% acetonitrile) to 65 vol % of eluent A/35 vol % of eluent B at a flow rate of 1 ml/min over 1 minute, and then by increasing with a linear gradient to 50 vol % of eluent A/50 vol % of eluent B over next 60 minutes, thereby to recover the eluate. The eluate was detected as a single peak at 210 nm by ultraviolet absorption.

The eluate was taken out by 500 µl each, giving a fraction number to each fraction, and 25 µl each from the fractions obtained was mixed with 150 µl of 0.2% BSA, followed by lyophilization with a freeze dryer (12EL; VirTis). The lyophilized product was added with 150 µl of H/HBSS containing 2.5 mM Probenecid and 0.1% CHAPS to dissolve the lyophilized product. By using 50 µl of the solution, the receptor activation activity on the ZAQ C-B1 cells was assayed by the test method described in (3-5) above. The result revealed that the component having the receptor activation activity on the objective ZAQ C-B1 cells, namely, the ZAQ activating component, was eluted mainly in fraction Nos. 82–84. This activation peak completely coincided with the ultraviolet absorption peak at 210 nm, leading to the conclusion that the product was purified enough to give the single peptide.

(3-8) Analysis of the Structure of Purified ZAQ Activating Peptide

The following procedure was used to determine the structure of ZAQ-activating component obtained in EXAMPLE (3-7) described above. The purified ZAQ activating component was lyophilized, and the lyophilized product was dissolved in solvent DMSO (dimethylsulfoxide). An aliquot of the solution was provided for the N-terminal amino acid sequencing, using a protein sequencer (Perkin-Elmer, Inc., PE Biosystems Procise 491cLC). As a result, 14 residues out of the amino acid residues from the N-terminus to the 16th amino acid residue could be identified (Ala Val Ile Thr Gly Ala Xaa Glu Arg Asp Val Gln Xaa Arg Ala Gly (SEQ ID NO:11; Xaa is an unidentified residue)).

Example 4

Cloning of cDNA for Human type ZAQ Ligand Peptide

A Blast search was made on database using as a query the N-terminal amino acid sequence (SEQ ID NO: 11) of the purified ZAQ activating peptide extracted from milk in EXAMPLE 3. Thus, human EST (X40467) was discovered, which has the same base sequence as that of DNA encoding the peptide having the amino acid sequence represented by SEQ ID NO:. 11. Since this sequence did not have a complete open reading frame, the unidentified sequence was identified by the RACE method, and continuously the cDNA clone having the complete open reading frame was acquired.

Based on the information from EST (X40467), primers ZF1 (SEQ ID NO: 12), ZF2 (SEQ ID NO: 13) and ZF3 (SEQ ID NO: 14) were designed, and the 3' RACE experiment was carried out, using human testis Marathon-Ready cDNA (CLONTECH Laboratories, Inc.) as a template. ZF1:5'-GGTGCCACGCGAGTCTCAATCATGCTCC-3' (SEQ ID NO: 12) ZF2:5'-GGGGCCTGTGAGCGGGATGTCCAGT-GTG-3' (SEQ ID. NO: 13) ZF3:5'-CTTCTTCAG-GAAACGCAAGCACCACACC-3' (SEQ ID NO: 14)

A PCR reaction solution for 3' RACE was prepared by mixing 1 µl of 50× Advantage 2 Polymerase Mix (CLONTECH Laboratories, Inc.), 5 µl of 10× Advantage 2 PCR buffer attached (400 mM Tricine-KOH, 150 mM KOAc, 35 mM Mg(OAc)$_2$, 37.5 µg/ml BSA, 0.05% Tween-20, 0.05% Nonidet-P40), 4 µl of dNTP mixture (2.5 mM each, TaKaRa Shuzo Co., Ltd.), 1 µl of 10 µM primer ZF1, 1 µl of 10 µM primer AP1 (primer AP1 was supplied with the human testis Marathon-Ready cDNA Kit by CLONTECH Laboratories, Inc.), 5 pl of template cDNA (CLONTECH Laboratories, Inc., human testis Marathon-Ready cDNA) and 33 µl distilled water. The reaction was carried out under the conditions: after primary denaturation at 94° C. for 60 seconds, a cycle set at 94° C. for 30 seconds and then at 72° C. for 4 minutes was repeated 5 times, a cycle set at 94° C. for 30 seconds and then at 70° C. for 4 minutes was repeated 5 times, and a cycle set at 94° C. for 30 seconds and then at 68° C. for 44 minutes was repeated 25 times.

Then, nested PCR was conducted using the reaction mixture of the PCR as a template. The reaction solution was prepared by mixing 1 µl of 50× Advantage 2 Polymerase Mix (CLONTECH), 5 µl of 10× Advantage 2 PCR buffer attached (400 mM Tricine-KOH, 150 mM KOAc, 35 mM Mg(OAc)$_2$, 37.5 µ/ml BSA, 0.05% Tween-20, 0.05% Nonidet-P40), 4 µl of dNTP mixture (2.5 nM each, TaKaRa Shuzo Co., Ltd.), 1 µl of 10 µM primer ZF2, 1 µl of 10 µM primer AP2 (primer AP2 was supplied with human testis Marathon-Ready cDNA Kit by CLONTECH Laboratories, Inc.), 5 µl of template DNA (50-fold dilution of the PCR reaction mixture) and 33 µl distilled water. The reaction was carried out under the conditions: after primary denaturation at 94° C. for 60 seconds, a cycle set at 94° C. for 30 seconds and then at 72° C. for 4 minutes was repeated 5 times, a cycle set at 94° C. for 30 seconds and then at 70° C. for 4 minutes was repeated 5 times, and a cycle set at 94° C. for 30 seconds and then at 68° C. for 44 minutes was repeated 25 times.

Furthermore, second nested PCR was conducted using the reaction solution of the PCR as a template. The reaction solution was prepared by mixing 1 µl of 50× Advantage 2 Polymerase Mix (CLONTECH Laboratories, Inc.), 5 µl of 10× Advantage 2 PCR buffer attached (400 mM Tricine-KOH, 150 mM KOAc, 35 mM Mg(OAc)$_2$, 37.5 µg/ml BSA, 0.05% Tween-20, 0.05% Nonidet-P40), 4 µl of dNTP mixture (2.5 mM each, TaKaRa Shuzo Co., Ltd.), 1 µl of 10 pM primer ZF3, 1 µl of 10 µM primer AP2 (primer AP2 was supplied with human testis Marathon-Ready DNA Kit by CLONTECH Laboratories, Inc.), 5 µl of template cDNA (50-fold dilution of the PCR reaction mixture) and 33 µl distilled water. The reaction was carried out under the conditions: after primary denaturation at 94° C. for 60 seconds, a cycle set at 94° C. for 30 seconds and then at 72° C. for 4 minutes was repeated 5 times, a cycle set at 94° C. for 30 seconds and then at 70° C. for 4 minutes was repeated 5 times, and a cycle set at 94° C. for 30 seconds and then at 68° C. for 44 minutes was repeated 25 times. The obtained DNA fragment was cloned using TOPO TA Cloning Kit (Invitrogen, Inc.) in accordance with the protocol described in the manual attached thereto. The base sequence of the cloned DNA was decoded using ABI377DNA sequencer to identify the 3' end sequence (SEQ ID NO: 15).

Based on the base sequence represented by SEQ ID NO: 15 and the information from EST (X40467), primer ZAQL-CF (SEQ ID NO: 16) and primer ZAQL-XR1 (SEQ ID NO: 17) were prepared. Using as a template human testis Marathon-Ready cDNA (CLONTECH Laboratories, Inc.), PCR was carried out using primers ZAQL-CF and ZQAL-XR1. ZAQL-CF: 5'-CCACCATGAGAGGTGCCACG-3' (SEQ ID NO: 16) ZAQL-XR1: 5'-CTCGAGCTCAGGAAAAG-GATGGTG-3' (SEQ ID NO: 17)

The reaction solution was prepared by mixing 1 µl of PfuTurbo DNA polymerase (Stratagene, Inc.), 5 µl of 10×PCR buffer attached, 4 µl of 2.5 mM dNTP mixture, 2.5 µl each of 10 µM primers ZAQL-CF and ZAQL-XR1, 5 µl of template DNA and 30 µl distilled water. The reaction was carried out under the conditions: after primary denaturation at 95° C. for 1 minute, a cycle set at 95° C. for 1 minute and then at 72° C. for 1 minute 94° C. was repeated 40 times, and a final extension reaction was conducted at 72° C. for 10 minutes. The obtained DNA fragment was cloned using TOPO TA Cloning Kit (Invitrogen) in accordance with the protocol described in the manual attached thereto. As a result of decoding the base sequences of the cloned DNA fragments using ABI377DNA sequencer, it was found that the fragments had 371 bp sequences represented by SEQ ID NO: 18 and SEQ ID NO: 19, respectively. The plasmid bearing the DNA fragment containing the base sequence represented by SEQ ID NO:18 was named pHMITA, and the plasmid bearing the DNA fragment containing the base sequence represented SEQ ID NO:19 was named pHMITG.

*Escherichia coli* was transformed using plasmids pHMITA and pHMITG, and the transformants obtained were named *Escherichia coli* TOP10/pHMITA and *Escherichia coli* TOP10/pHMITG, respectively.

Analysis of the base sequences of the DNA fragments revealed that the DNA fragment represented by SEQ ID NO: 18 had the DNA (SEQ ID NO: 28) encoding human type ZAQ ligand precursor peptide (type A, 105 amino acid residues) represented by SEQ ID NO: 22, and that the DNA fragment represented by SEQ ID NO: 19 had the DNA (SEQ ID NO: 29) encoding human type ZAQ ligand precursor peptide (type G, 105 amino acid residues) represented by SEQ ID NO: 23.

It was further found that the base sequences represented by SEQ ID NO: 28 and represented by SEQ ID NO: 29 had a typical signal sequence; the DNA having the base sequence represented by SEQ ID NO: 28 had the DNA (SEQ ID NO: 26) consisting of 258 base pairs and encoding human type ZAQ ligand mature peptide (type A, 86 amino acid residues) represented by SEQ ID NO: 20; the DNA having the base sequence represented by SEQ ID NO: 29 had the DNA (SEQ ID NO: 27) consisting of 258 base pairs and encoding human type ZAQ ligand mature peptide (type G, 86 amino acid residues) represented by SEQ ID NO: 21.

Example 5

Production of Human Type ZAQ Ligand Peptide in Mammalian Cells (1)

(5–1) Construction of the Mammalian Expression Vector for Human Type ZAQ Ligand Precursor Peptide The plasmid pHMITG acquired in EXAMPLE 4 was digested with restriction enzymes EcoRI and XhoI to excise the 382 bp DNA fragment (SEQ ID NO: 30) containing cDNA encoding human type ZAQ ligand precursor peptide.

Figure 11:
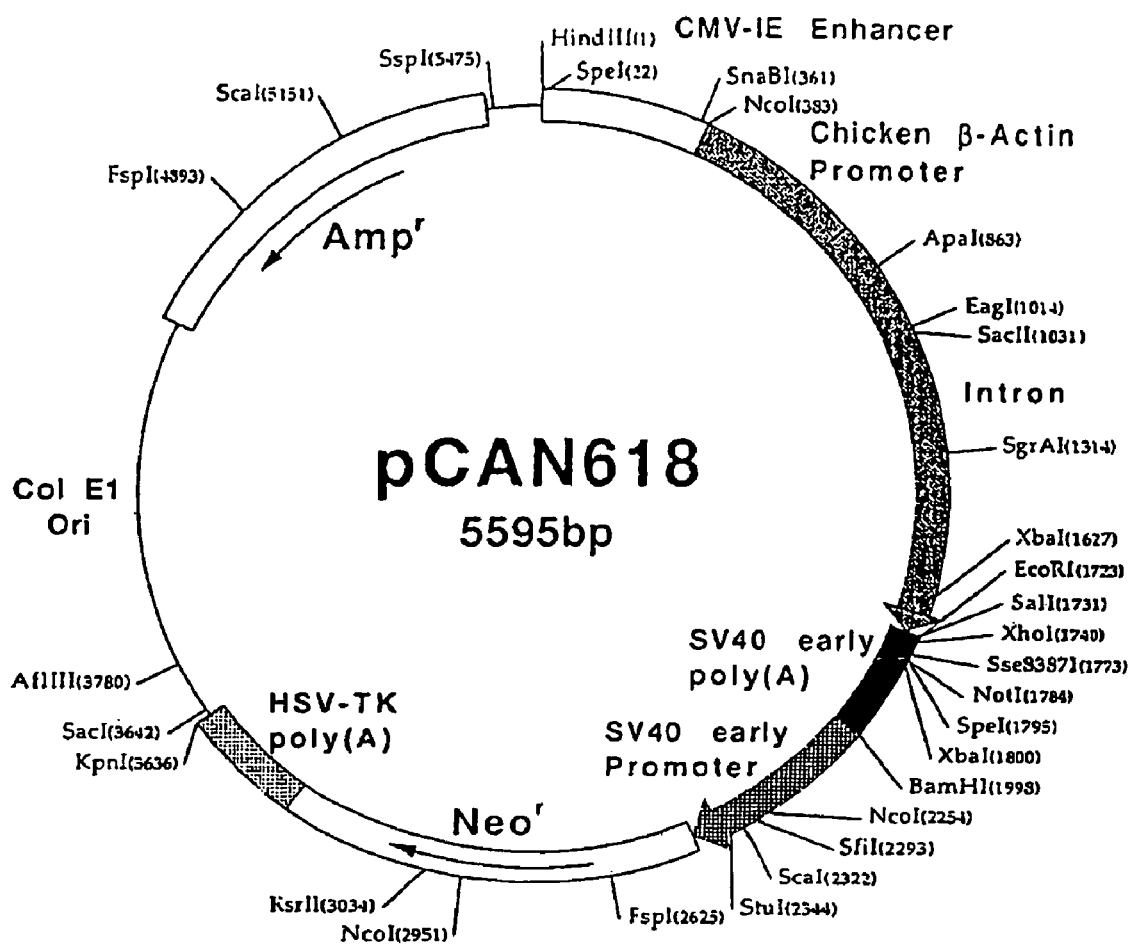
FIG. 11 shows a restriction enzyme map of plasmid pCAN618 used in EXAMPLE 5 (5-11).

That is, plasmid pHMITG was digested with EcoRI and XhoI, and the obtained DNA fragment was electrophoresed on 1.5% agarose gel. The gel segment of the 382 bp band stained with cyber green was cut out with a razor blade. From the above gel segment, the DNA fragment was recovered using Gene Clean Spin DNA Extraction Kit (BIO 101, Inc.). According to the standard method, the acquired DNA fragment was cloned into the mammalian cell expression vector pCAN618 (FIG. 11) bearing CMV-IE enhancer and chicken beta-actin promoter as an expression promoter at the cleavage site by restriction enzymes EcoRI and XhoI. The base sequence of the cloned DNA fragment was decoded by to the above method. Thus, the DNA fragment was identified to have the base sequence represented by SEQ ID NO: 30. This mammalian cell expression vector having the DNA encoding human type ZAQ ligand precursor peptide was named pCANZAQLg2.

(5-2) Introduction of Expression Vector into COS7 Cells

COS7 cells were purchased from ATCC, and the cells subcultured by DMEM medium (supplemented with 10% FBS) were used. Using DMEM medium, COS7 cells were inoculated at a population of $1.5 \times 10^6$ cells/dish on 10 cm Petri dish, followed by incubation at 37° C. under 5% $CO_2$ overnight. To 2 μg of the expression plasmid of human type ZAQ ligand precursor peptide (dissolved in 2 μl of TE buffer) (pCANZAQLg2) was added 298 μl of Buffer EC (Effectene transfection reagent, QIAGEN) and, 16 μl of Enhancer was further added to the mixture. After mixing for one second, the mixture was allowed to stand at a room temperature for 3 minutes. Then, 60 μl of Effectene Trasfection Reagent was further added to the mixture. After mixing for 10 seconds, the mixture was allowed to stand at room temperature for 10 minutes. After the supernatant was removed from the cells inoculated the day before, the cells were washed once with 10 ml of DMEM medium and 9 ml of DMEM medium was added thereto. One milliliter of DMEM medium was added to the plasmid solution, and after mixing, the mixture was dropwise added to the cells. After mixing the whole mixture, the cells were cultured at 37° C. under 5% $CO_2$ overnight. The cells were washed twice with 10 ml of DMEM medium, and 10 ml of DMEM medium was added thereto. The cells were cultured in an incubator at 37° C. under 5% $CO_2$ overnight. After 2 days, the culture supernatant was recovered.

(5-3) Partial Purification of Human Type ZAQ Ligand Precursor Peptide from the Culture Supernatant of Expression COS7 Cells (5-3-1) Preparation of the Culture Supernatant of Human Type ZAQ Ligand Precursor Peptide Expressing COS7 Cells The culture supernatant of human type ZAQ ligand precursor peptide expressing COS7 cells was recovered, and the extract was prepared by the following procedure. First, 1.1 ml of acetic acid was dropwise added to the cell culture supernatant (about 18.5 ml) to adjust the final concentration to 1 M, and the mixture was agitated for an hour. Acetone was added thereto in 2wo-fold volume of the mixture, which was then agitated for 30 minutes at 4° C. Next, the mixture was centrifuged at 15,000 rpm for 30 minutes using a high speed centrifuge (CR26H, Model 23 Rotor: Hitachi, Ltd) to obtain the supernatant. The supernatant obtained was set in an evaporator to remove acetone, and then lyophilized with a freeze dryer (12EL; VirTis).

(5-3-2) Sephadex G50 Gel Chromatography and SepPak Column Chromatography of the Culture Supernatant of Human Type ZAQ Ligand Precursor Peptide Expressing COS7 Cells The lyophilized powders obtained in (5-3-1) above were dissolved in 2 ml of 1 M acetic acid, and the solution was adsorbed onto Sephadex G15 column (3 cm×35 ml, Pharmacia Biotech), which was equilibrated with 1 M acetic acid. Then, I M acetic acid was passed through the column, and 5 ml each of the eluate was taken out, giving a fraction number to each fraction. Each fraction was lyophilized with a freeze dryer (12EL; VirTis).

SepPak C18–5g column (10 ml) was swollen with methanol, and equilibrated with 0.1% of trifluoroacetic acid/distilled water. The lyophilized products of fraction Nos. 1 through 16 taken from the fractions obtained by Sephadex G50 gel chromatography were pooled and dissolved in 3 nl of trifluoroacetic acid/distilled water, and the solution was loaded onto SepPak C18-5 g column. After washing with 24 ml of 0.1% trifluoroacetic acid/distilled water, the column was washed and eluted with 20 ml of 0.1% trifluoroacetic acid/60% acetonitrile. The eluate obtained was applied to Savant.

(5–3–3) Purification of Super ODS Reversed Phase High Performance Liquid Chromatography Eluent A (0.1% trifluoroacetic acid/distilled water) was passed through the column for TSKgel Super ODS reversed phase high performance liquid chromatography (Toso, 0.46 cm×10 cm) at a flow rate of 1 ml/min at 40° C. to equilibrate the column. After the SepPak C18-5g column fraction obtained in (5-3-2) was applied to Savant, the fraction was loaded onto Super ODS reversed phase high performance liquid chromatography. Then, elution was carried out by increasing with a linear gradient from 100 vol % of eluent A (0.1% trifluoroacetic acid/distilled water)/0 vol % of eluent B (0.1% trifluoroacetic acid/100% acetonitrile) to 0 vol % of eluent A/100 vol % of eluent B at a flow rate of 1 ml/min over 60 minutes, thereby to recover the eluate.

The eluate was fractionated by 1 ml each, giving a fraction number to each fraction. The whole amount of the fractionated fractions was lyophilized with a freeze dryer (12EL; VirTis). The lyophilized products were dissolved in 150 μl of H/HBSS supplemented with 2.5 mM Probenecid and 0.2% BSA. Using this solution, the effect of activating the receptor to ZAQC-B1 cells was assayed by the testing method (5-3-4) described below.

(5-3-4) Measurement of the Intracellular $Ca^{2+}$ Ion Concentration Increasing Activity by FLIPR Using FLIPR, the samples obtained in (5-3-4) above were assayed for the intracellular $Ca^{2+}$ ion concentration increasing activity in ZAQ expression cells (ZAQC-B1) obtained in EXAMPLE 3 (3-5). For control, hOT7T175 expression cells (hOT7T175-16; described in WO 00/24890) were used.

The ZAQC-B1 cells and hOT7T175 cells were subcultured in DMEM supplemented with 10% dialyzed fetal bovine serum (hereinafter referred to as dFBS) and provided for use. The ZAQC-B1 cells and h0T7T175 cells were suspended, respectively, in the medium (10% dFBS-DMEM) to adjust their concentration to $15\times10^4$ cells/ml. Using a dispensing pipette, 200 µl each of the cell suspension were inoculated ($3.0\times10^4$ cells/200 µl/well) in each well (Black Plate Clear Bottom, Coster). After incubation at 37° C. under 5% $CO_2$ for one day, the cells were used (hereinafter referred to as the cell plate). Twenty-one milliliter of H/HBSS (9.8 g of HANKS', 0.35 g of sodium hydrogencarbonate and 4.77 g of HEPES; adjusted to pH 7.4 with sodium hydroxide followed by sterilization through a sterilizing filter), 210 µl of 250 mM Probenecid and 210 µl of fetal bovine serum (FBS) were mixed. Also, 2 vials (50 µg) of Fluo 3-AM were dissolved in 42 µl of dimethylsulfoxide and 42 µl of 20% Pluronic acid, and the resulting solution was added to the above H/HBSS-Probenecid-FBS mixture. After mixing, the medium was removed from the cell plate, and 100 µl each of the mixture was dispensed into each well of the cell plate using an 8-channel pipette. The cell plate was then incubated at 37° C. under 5% $CO_2$ for an hour (dye loading). For the assay samples obtained in EXAMPLE (5-3-3) described above, 150 µl of H/HBSS containing 2.5 mM Probenecid and 0.2% FBS was added to each fraction for dissolution. The solution was then transferred to a 96-well plate (V-Bottom Plate, Coster) for FLIPR (hereinafter referred as to the sample plate). After completion of the dye loading, the cell plate was washed four times with the wash buffer or H/HBSS supplemented with 2.5 mM Probenecid, using a plate washer (Molecular Devices). After washing, 100 µl of the wash buffer was saved. This cell plate and the sample plate were loaded onto FLIPR to conduct the assay (0.05 ml of sample was transferred from the sample plate to the cell plate by FLIPR). The intracellular $Ca^{2+}$ ion concentration increasing activity specific to ZAQ-B 1 cells was observed in fraction Nos.48 to 68. From this, it was found that the target component having the function of activating the receptor to ZAQC-B1 cells, i.e., the ZAQ activating component, was eluted in fraction Nos. 48 to 68.

Example 6

Production of Human Type ZAQ Ligand Peptide in Mamalian Cells (2)

(6-1) Preparation of the Culture Supernatant

As described in EXAMPLE 5, the expression plasmid of human type ZAQ ligand precursor peptide (pCANZAQLg2) was introduced into COS7 cells. That is, COS7 cells were inoculated at a population of $3.0\times10^6$ cells/dish on a 15 cm Petri dish, followed by incubation at 37° C. under 5% $CO_2$ overnight. After 600 µl of Buffer EC (Effectene transfection reagent, QIAGEN) was added to 4 µg of the human type ZAQ ligand precursor peptide expression plasmid (pCAN-ZAQLg2) (dissolved in 4 µl of TE buffer), 32 µl of Enhancer was further added thereto. After mixing for one second, the mixture was allowed to stand for 3 minutes at room temperature. Further, 120 µl of Effectene Transfection Reagent was added to the mixture. After mixing for 10 seconds, the mixture was allowed to stand for 10 minutes at room temperature. The supernatant was removed from the cells inoculated the day before, and the cells were washed once with 10 ml of DMEM and 30 ml of DMEM was added thereto. To the plasmid solution, 1 ml of DMEM was added, and after mixing, the mixture was dropwise added to the cells. After mixing the whole mixture, the cells were cultured at 37° C. under 5% $CO_2$ overnight. The cells were washed once with 10 ml of DMEM, and 20 ml of DMEM was added thereto. The cells were cultured in an incubator at 37° C. under 5% $CO_2$ overnight. The next day, the culture supernatant was collected, and 20 ml of DMEM was added to the system. The mixture was cultured in an incubator at 37° C. under 5% $CO_2$ overnight to recover the culture supernatant.

(6-2) Purification of Human Type ZAQ Ligand Peptide from the Culture Supernatant Using the procedure described in (6-1) above, the culture medium was recovered from 80 Petri dishes of 15 cm. Acetic acid was added to the medium to adjust the final concentration to become 1 M. After 1 hour of agitation, acetone was added in a 2-fold volume of the solution to precipitate proteins. The solution was agitated for 30 minutes at 4° C. Then, the solution was centrifuged at 10,000 rpm for 30 minutes with a high-speed centrifuge (CR26H RR10A type rotor: Hitachi System Engineering Co., Ltd.) to obtain a supernatant. The supernatant obtained was applied to an evaporator to remove acetone, and passed through a reversed phase column (Waters C18, 100 g), which had previously been equilibrated with 0.1% trifluoroacetic acid/distilled water. After the column was washed with 1,000 ml of 0.1% trifluoroacetic acid/distilled water and then with 1,000 ml of 0.1% trifuluoroacetic acid/20% acetonitrile, the peptide was eluted with 1,000 ml of 0.1% trifluoroacetic acid/60% acetonitrile. The eluate obtained was applied to an evaporator, and lyophilized with a freeze dryer (12EL; Vir Tis).

Eluent A (0.1% trifluoroacetic acid/distilled water) was passed through the column for TSKgel ODS80TM reversed phase high performance liquid chromatography (Toso, 21.5 mm×30 cm) at a flow rate of 4 ml/min at 40° C. to equilibrate the column. After the lyophilized powders obtained were dissolved in eluent A, the solution was loaded onto the ODS80TM column, the peptide was eluted by increasing with a linear gradient from 60 vol % of eluent A (0.1% trifluoroacetic acid/distilled water)/40 vol % of eluent B (0.1% trifluoroacetic acid/60% acetonitrile) to 0 vol % of eluent A/100 vol % of eluent B at a flow rate of 1 ml/min over 120 minutes.

The eluate was fractionated by 8 ml each, giving a fraction number to each fraction. From the fractions obtained, 50 µl each was taken out and lyophilized with a freeze dryer (12EL; VirTis). The lyophilized products were dissolved in 200 µl of H/HBSS supplemented with 2.5 mM Probenecid and 0.2% BSA. Using this solution, the effect of activating the receptor to ZAQC-B1 cells was assayed by the testing method (5-3-4) described below. The results revealed that the target component having the effect of activating the receptor to ZAQC-B 1 cells, i.e., the ZAQ activating component, was eluted in fraction No. 32.

Eluent A (10 mM ammonium formate/10% acetonitrile) was passed through the column for TSKgel CM-2SW ion exchange high performance liquid chromatography (Toso, 4.6 mm×25 cm) at a flow rate of 1 ml/min at 25° C. to equilibrate the column. Fraction No. 32 described above was loaded onto the CM-2SW column, and the peptide was eluted with a linear gradient, by increasing from 100 vol % of eluent A (10 mM ammonium formate/10% acetonitrile)/0 vol % of eluent B (1000 mM ammonium formate/10% acetonitrile) to 0 vol % of eluent A/100 vol % of eluent B at a flow rate of 1 ml/min over 60 minutes.

The eluate was fractionated by 1 ml each, giving a fraction number to each fraction. From the fractions obtained, 1.5 µl was taken and diluted with 200 µl of H/HBSS supplemented with 2.5 mM Probenecid and 0.2% BSA. This solution was used to assay the function of activating the receptor to ZAQC-B1 cells by the testing method (5-3-4) described above. The results revealed that the target component having the function of activating the receptor to ZAQC-B1 cells, i.e., the ZAQ activating component, was eluted in fraction Nos. 56 and 57.

Eluent A (0.1% trifluoroacetic acid/distilled water) was passed through the column for TSKgel Super phenyl reversed phase high performance liquid chromatography (Toso, 4.6 mm×10 cm) at a flow rate of 1 ml/min at 40° C. to equilibrate the column. Fraction Nos. 56 and 57 above were loaded onto said Super phenyl column, and the peptide was eluted by increasing with a linear gradient from 70 vol % of eluent A (0.1% trifluoroacetic acid/distilled water)/30 vol % of eluent B (0.1% trifuluoroacetic acid/60% acetonitrile) to 50 vol % of eluent A/50 vol % of eluent B over 60 minutes at a flow rate of 1 ml/min.

The eluate was fractionated by 1 ml each, giving a fraction number to each fraction, and 1.5 μl of the eluate was taken from the fractions obtained. The eluate was and diluted with 200 μl of H/HBSS supplemented with 2.5 mM Probenecid and 0.2% BSA. This solution was used to assay for the function of activating the receptor to ZAQC-B1 cells by the testing method (5-3-4) described above. The results revealed that the target component having the function of activating the receptor to ZAQC-B1 cells, namely, the ZAQ activating component, was eluted in fraction Nos. 54, 55 and 56. The activity was coincident with the single ultraviolet absorption peak, which was interpreted that the activating component was purified enough to homogeneity.

The purified ZAQ activating component was lyophilized, and the lyophilized product was dissolved in solvent DMSO (dimethylsulfoxide). An aliquot of the solution was provided for the N-terminal amino acid sequencing, using a protein sequencer (Perkin-Elmer, Inc., PE Biosystems Procise 491cLC). As a result, 9 residues out of the amino acid residues from the N-terminus to the 10th amino acid residue could be identified (Ala Val Ile Thr Gly Ala Xaa Glu Arg Asp (SEQ ID NO: 31; Xaa is an unidentified residue)). The obtained amino acid sequence was coincident with the N-terminal amino acid sequence of the predicted human type ZAQ ligand mature peptide. Also, mass spectrometry was conducted for the purified sample of ZAQ activating component, using Finnigan LCQ LC/MC apparatus (Thermoquest, San Jose, Calif.) in accordance with the electrospray ionization method so that the molecular weight was found to be 9657.6. This result was well coincident with the calculated value of 9657.3 for human type ZAQ ligand mature peptide of 86 residues, in which all of 10 cystein residues formed disulfide bonds. It was thus confirmed that the purified sample of ZAQ activating component had human type ZAQ ligand mature peptide having the amino acid sequence represented by SEQ ID NO: 21.

Figure 10:
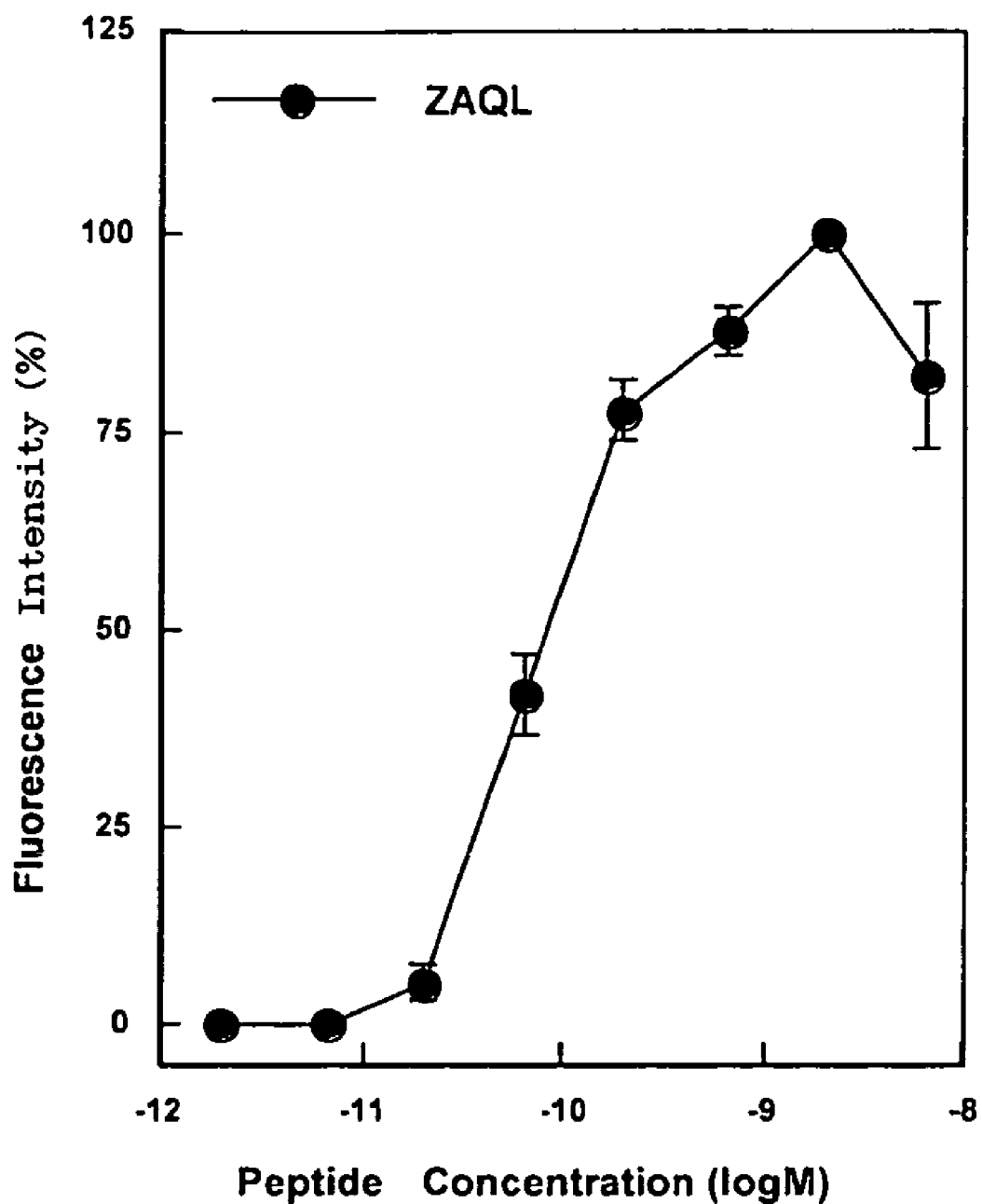
FIG. 10 shows the results of the analysis for ZAQ activating effect by the ZAQ ligand peptide purified in EXAMPLE 6 (6-3).

(6-3) Assay for the ZAQ Activating Function of Purified Human Type ZAQ Ligand Peptide The function of activating the receptor to ZAQC-B1 cells by the human type ZAQ ligand mature peptide purified in (6-2) above was assayed by the testing method described in (5-3-4) above. The results revealed that the human type ZAQ ligand mature peptide induced an increase of the intracellular calcium ion concentration in the ZAQ-expressed CHO cells (ZAQC-B1 cells) concentration-dependently. The $EC_{50}$ value was 96 pM, and it was discovered that human type ZAQ ligand mature peptide exhibited a very potent agonist activity. The results are shown in FIG. 10.

Example 7

Production of Human Type ZAQ Ligand Peptide in Mammalian Cells (3)

(7-1) Establishment of CHO Cell Line Capable of Stably Expressing the Human Type ZAQ Ligand Peptide Using as a template plasmid pHMITG described in EXAMPLE 4, human type ZAQ ligand cDNA was amplified by PCR using the following primers: 5' GTCGACCACCAT-GAGAGGTGCCACGC 3' (SEQ ID NO: 32) 5' ACT-AGTCGCAGAACTGGTAGGTATGG 3' (SEQ ID NO: 33) and cloned onto pCR Blunt II vector (Invitrogen, Inc.). The insert cDNA was excised from the obtained clone having a correct sequence, using restriction enzymes SalI and SpeI, and incorporated into pAKKO1.1H expression vector. The plasmid was transfected to CHO/dhFr⁻ cells (American Type Culture Collection) by the procedure described in (3-5) above using CellPhect Transfection Kit (Amersham Pharmacia Biotech). The culture supernatant was recovered from several clones of the transfected strain, and the ZAQ ligand activity capable of increasing the intracellular $Ca^{2+}$ ion concentration in the ZAQC-B1 cells was assayed by the testing method described in (3-5). Thus, ZAQL-expressed CHO cell clone No. 4 capable of highly expressing the ZAQ ligand was screened.

(7–2) Preparation of Serum-free Culture Supernatant of Human Type ZAQ Ligand (ZAQL-1)

In Dulbecco's Modified Eagle Medium (DMEM) (Nissui Pharmaceutical Co., Ltd.) supplemented with 10% dialyzed fetal bovine serum (JRH BIOSCIENCES), 1 mM of MEM non-essential amino acid solution, 100 units/ml of penicillin and 100 μg/ml of streptomycin, ZAQL-1-expressed CHO cell clone No. 4 was cultivated to become confluent using 4 Single Trays (Nunc), and treated with trypsin for dispersion. The dispersion was centrifuged to recover the clone. The cells corresponding to one of the Single Tray above were suspended in 1.5 L of the medium, and inoculated into Cell Factories 10 (Nunc), followed by incubating 4 Cell Factories 10 at 37° C. for 3 days under 5% $CO_2$. After the culture supernatant was removed, the cells in one of Cell Factories 10 were washed with 1 L of the H/HBSS described above. After the H/HBSS was removed, serum-free medium (Dulbecco's Modified Eagle Medium supplemented with 1 mM non-essential amino acid solution, 100 units/ml Penicillin and 100 μg/ml Streptomycin) was added in 2 L per one Cell Factories 10, followed by incubation for further 2 days. The recovered culture supernatant was centrifuged at 1,000 rpm for 10 minutes using Hitachi high speed centrifuge, and filtrated through a gauze to give a clear supernatant. Acetic acid was added to the supernatant in a final concentration of 1 M.

(7–3) Crude Fractionation of ZAQL-1 Expression CHO Cell Serum-free Culture Supernatant by Wakosil-II5C18HG Prep Reversed Phase High Performance Liquid Chromatography PrepC18 (Waters) packed with octadecyl-fixed silica gel was swollen in methanol, which was packed into a glassmade column (50 mm×100 mm). Then, the extract prepared in (6-2) was loaded onto a column, which had been equilibrated with 1 M acetic acid. Next, the column was :washed with 800 ml of 1 M acetic acid. Then, 1000 ml of 60% acetonitrile/0.1% trifluoroacetic acid was passed through the column to elute the objective crude peptide component. The eluate obtained was concentrated using an evaporator and lyophilized with a freeze dryer (12EL; VirTis).

(7–4) Separation by Wakosil-II5C18HG Prep Reversed Phase High Performance Liquid Chromatography By passing 91.7 vol % of eluent A (0.1% trifluoroacetic acid/distilled water)/8.3 vol % of eluent B (0.1% trifluoroacetic acid/60% acetonitrile) through a column for Wakosil-II 5C18HG Prep reversed phase high performance liquid chromatography (Wako Pure Chemical Industries, 20 mm×250 mm) at 40° C. at a flow rate of 5 ml/min, the column was equilibrated. The lyophilized product obtained in (7-3) above was subjected to chromatography procedure. That is, 36 ml of 1M acetic acid was added to dissolve the lyophilized product. After the solution was centrifuged, a ⅓ aliquot was loaded onto the column, and the concentration of eluent B was increased to 66.7 vol % of eluent A/33.3 vol % of eluent B over a minute and then increased with a linear gradient to 16.7 vol % of eluent A/83.3 vol % of eluent B over next 120 minutes, at a flow rate of 5 ml/ml. The eluate was fractionated by 5 ml each, giving a fraction number to each fraction, and 3 μl each from the fractions obtained was mixed with 150 μl of 0.2% BSA, followed by lyophilization with a freeze dryer (12EL; VirTis). The lyophilized product was added with 150 μl of assay buffer [H/HBSS (9.8 g of Nissui HANKS 2 (Nissui Pharmaceutical Co., Ltd.), 0.35 g of sodium hydrogencarbonate and 4.77 g of HEPES; adjusted to pH 7.4 with sodium hydroxide followed by sterilization through a sterilizing filter) supplemented with 2.5 mM Probenecid and 0.1% CHAPS] to dissolve the lyophilized product. By using 50 μl of the solution, the ZAQ-B 1 receptor activating function was assayed by the testing method described in (3-5) above. The results revealed that the component having the objective ZAQ-B1 receptor activating function was eluted mainly in fraction Nos. 73–75.

(7–5) Separation by TSKgel CM-2SW Ion exchange High Performance Liquid Chromatography By passing 100 vol % of eluent A (4 M ammonium formate: distilled water:acetonitrile=1:299:100) and 0 vol % of eluent B (4 M ammonium formate:distilled water:acetonitrile=1:2:1) through a column for TSKgel CM-2SW ion exchange high performance liquid chromatography (Toso, 7.8 mm×300 mm) at a flow rate of 2 ml/min at 25° C., the column was equilibrated. In the fractions obtained in (7-4) by Wakosil-II5C18HG Prep reversed phase high performance liquid chromatography, fraction Nos. 73–75 were lyophilized, and the lyophilized products were dissolved in 4 ml of eluent A. After the solution was loaded onto the TSKgel CM-2SW ion exchange column, the eluate was recovered by increasing with a linear gradient to 25 vol % of eluent A/75 vol % of eluent B over 120 minutes at a flow rate of 1 ml/min. The eluate was fractionated by 2 ml each, giving a fraction number to each fraction, and 10 μl each from the fractions obtained was mixed with 100 μl of 0.2% BSA, followed by lyophilization with a freeze dryer (12EL; VirTis). The lyophilized product was added with 100 μl of the assay buffer described above to dissolve. After the solution was diluted to 100-fold with the same buffer, the ZAQ receptor activating function was assayed by the testing method described in (3-5) above. The results revealed that the component having the objective ZAQ receptor activating function was eluted mainly in fraction Nos. 95–100.

(7-6) Purification by TSKgel ODS-80Ts Reversed Phase High Performance Liquid Chromatography By passing 91.7 vol % of eluent A (0.1% trifluoroacetic acid/distilled water) and 8.3 vol % of eluent B (0.1% trifluoroacetic acid/60% acetonitrile) the column for TSKgel ODS-80Ts reversed phase high performance liquid chromatography (Toso Co., Ltd., 4.6 mm×25 cm) at a flow rate of 1 ml/min at 40° C., the column was equilibrated. The lyophilized products of fraction Nos. 95–100 obtained in (7-5) above were subjected to chromatography treatment. That is, the lyophilized products were dissolved in 4 ml of 1 M acetic acid, and the solution was loaded onto the column. The concentration of eluent B was increased to 75 vol % of eluent A/25 vol % of eluent B over 1 minute and then increased with a linear gradient to 25 vol % of eluent A/75 vol % of eluent B over next 60 minutes at a flow rate of 1 ml/min, thereby to recover the eluate. The eluate was fractionated by 1 ml each, giving a fraction number to each fraction. The ZAQ ligand activity was assayed in accordance with the testing method described in (3-5), and it was confirmed that the activity was eluted in the fraction coincident with the single ultraviolet absorption peak. From this it was interpreted that the ZAQ ligand was purified enough to homogeneity.

(7-7) Analysis of the Structure of Purified ZAQ Ligand Peptide

The following procedure was used to determine the structure of ZAQ ligand peptide obtained in (7-6) described above. The purified main ZAQ activating component was lyophilized with a freeze dryer (12EL; VirTis). The lyophilized product was dissolved in solvent DMSO (dimethylsulfoxide). An aliquot of the solution was provided for the N-terminal amino acid sequencing, using a protein sequencer (Perkin-Elmer, Inc., PE Biosystems Procise 491cLC). As a result, the N-terminal amino acid sequence coincident with the predicted human type ZAQ ligand peptide mature form (SEQ ID NO: 21) was obtained. Also, mass spectrometry was conducted in accordance with the electron spray ionization method, using Finnigan LCQ LC/MC apparatus, and the molecular weight was found to be 9658.0. This value found was well coincident with the calculated value of 9657.3 for human type ZAQ ligand mature peptide (SEQ ID NO: 21). It was thus confirmed that the objective peptide having the amino acid sequence represented by SEQ ID NO: 21 was acquired.

Example 8

Reactivity of Snake Venom MIT1 and Human Type ZAQ Ligand with ZAQ and 15E (8-1) Isolation of Snake Venom MIT1

(8-1-1) Separation by Wakosil-II 5C18HG Prep Reversed Phase High Performance Liquid Chromatography By passing 91.7 vol % of eluent A (0.1% trifluoroacetic acid/distilled water)/8.3 vol % of eluent B (0.1% trifluoroacetic acid/60% acetonitrile) through a column for Wakosil-II 5C18HG Prep reversed phase high performance liquid chromatography (Wako Pure Chemical Industries, 20 mm×250 mm) at 40° C. at a flow rate of 5 ml/min, the column was equilibrated. To 50 mg of the lyophilized product of Black Mamba venome (Sigma) was added 4 ml of 1M acetic acid to dissolve the lyophilized product. The solution was centrifuged at 15,000 rpm for 10 minutes, and the supernatant was subjected to chromatography. After the sample was loaded onto the column, the concentration of eluent B was increased to 91.7 vol % of eluent A/8.3 vol % of eluent B over 1 minute and then increased with a linear gradient to 33.4 vol % of eluent A and 66.6 vol % of eluent B over 120 minutes, at a flow rate of 5 ml/min. The eluate was fractionated by 10 ml each 20 minutes after, giving a fraction number to each fraction. From each fraction 1 μl was taken out and after diluting to 10,000-fold with the assay buffer described above, the ZAQ-B1 receptor activating function was assayed in accordance with the testing method described in (3-5) above. The results revealed that the component having the objective ZAQ-B1 receptor activating function was eluted mainly in fraction Nos. 21–23.

(8-1-2) Separation by TSKgel CM-2SW Ion Exchange High Performance Liquid Chromatography By passing 100 vol % of eluent A (4 M ammonium formate: distilled water: acetonitrile=1:299:100) and 0 vol % of eluent B (4 M ammonium formate:distilled water: acetonitrile=1:2:1) through a column for TSKgel CM-2SW ion exchange high performance liquid chromatography (Toso, 4.6 mm×250 mm) at a flow rate of 1 ml/min at 25° C., the column was equilibrated. In the fractions obtained in (7-1) by Wakosil-II 5C18HG Prep reversed phase high performance liquid chromatography, fraction Nos. 21–23 were lyophilized, and the lyophilized products were dissolved in 4 ml of eluent A. After the solution was loaded onto the TSKgel CM-2SW ion exchange column, the eluate was recovered by increasing with a linear gradient to 0 vol % of eluent A/100 vol % of eluent B over 90 minutes at a flow rate of 1 ml/min. The eluate was fractionated by 1 ml each, giving a fraction number to each fraction. From each fraction 1 µl was taken out and after diluting to 10,000-fold with the assay buffer described above, the ZAQ-B1 receptor activating function was assayed in accordance with the testing method described in (3-5) above. The results revealed that the component having the objective ZAQ-B1 receptor activating function was eluted mainly in fraction Nos. 50–51.

(8-1-3) Separation by Vydac238TP3410 Ion Exchange High Performance Liquid Chromatography By passing 91.7 vol % of eluent A (0.1% trifluoroacetic acid/distilled water)/8.3 vol % of eluent B (0.1% trifluoroacetic acid/60% acetonitrile) through a column for Vydac238TP3410 ion exchange high performance liquid chromatography (Toso, 4.6 mm×100 mm) at a flow rate of 1 ml/min at 40° C., the column was equilibrated. In the fractions obtained in (8-1-2) by TSKgel CM-2SW ion exchange high performance liquid chromatography, fraction Nos. 50–51 were directly loaded onto the said column, the concentration of eluent B was increased to 75 vol % of eluent A/25 vol % of eluent B over 1 minute and then increased with a linear gradient 41.7 vol % of eluent A and 58.3 vol % of eluent B over 75 minutes, at a flow rate of 1 ml/min. The eluate was fractionated by 0.5 ml each, giving a fraction number to each fraction. From each fraction 1 µl was taken out and after diluting to 10,000-fold with the assay buffer described above, the ZAQ-B1 receptor activating function was assayed in accordance with the testing method described in (3-5) above. The results revealed that the component having the objective ZAQ-B1 receptor activating function was eluted mainly in fraction Nos. 108–115.

(8-1-4) Analysis of the Structure of Purified Snake Venom MIT1

The following procedure was used to determine the structure of snake venom MIT1 obtained in (8-1-3) described above. The purified main MIT1 was lyophilized with a freeze dryer (12EL; VirTis). The lyophilized product was dissolved in solvent DMSO (dimethylsulfoxide). An aliquot of the solution was provided for the N-terminal amino acid sequencing, using a protein sequencer (Perkin-Elmer, Inc., PE Biosystems Procise 491cLC). As a result, the N-terminal amino acid sequence coincident with the predicted snake venom MIT1 (SEQ ID NO: 34) was obtained. Also, mass spectrometry was conducted in accordance with the electron spray ionization method, using Finnigan LCQ LC/MC apparatus, and the molecular weight was found to be 8506.8. This value found was well coincident with the calculated value of 8506.4 for snake venom MIT1. It was thus confirmed that the objective peptide having the amino acid sequence represented by SEQ ID NO: 34 was acquired.

(8-2) Establishment of Cell Line Capable of Stably Expressing I5E

Human type I5E receptor cDNA (SEQ ID NO: 35) was cloned by known PCR, and incorporated into pAKKO1.1H expression vector. The expression vector was transfected to CHO/dhFr⁻ cells (American Type Culture Collection) by the procedure described in (3-5) above. About 20 colonies of the transformant CHO cells grown 10 to 14 days after the initiation of incubation were selected. The selected transformants were inoculated into a 96-well plate in $3\times10^4$ cells/well, and the reactivity with MIT1 was examined in accordance with the testing method described in (3-5). I5E-expressed CHO cell No. 4 clone (referred to as I5E-4 cell) having a good reactivity was screened. The amino acid sequence encoded by the base sequence represented by SEQ ID NO: 35 is shown by SEQ ID NO: 36.

(8-3) Assay for the ZAQ Receptor and I5E Receptor Activating Function of Human Type ZAQ Ligand Peptide and MIT1

Figure 12:
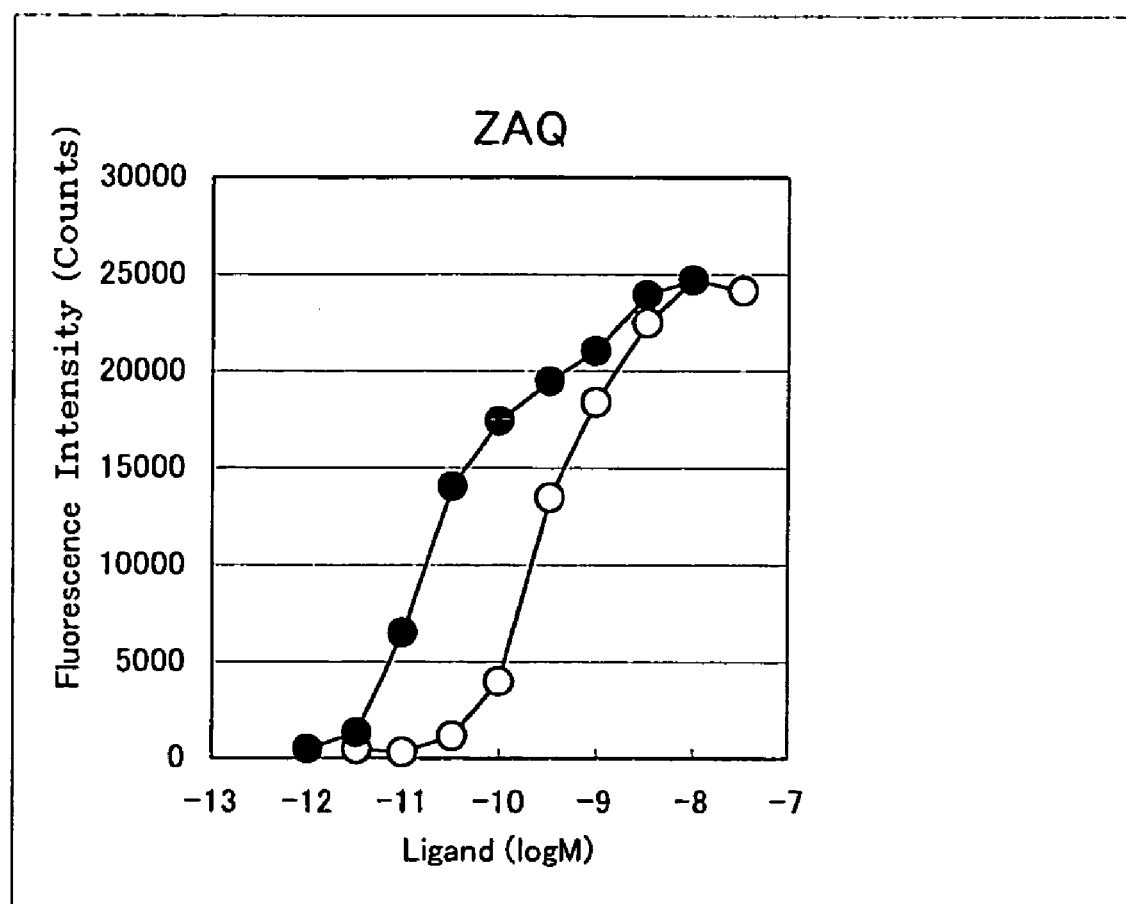
FIG. 12 shows the results of the measurement for ZAQ receptor activating effects by human type ZAQ ligand peptide and MIT1 assayed in EXAMPLE 8 (8-3), wherein -o- and -•- represent human type ZAQ ligand peptide and MIT1, respectively.
Figure 13:
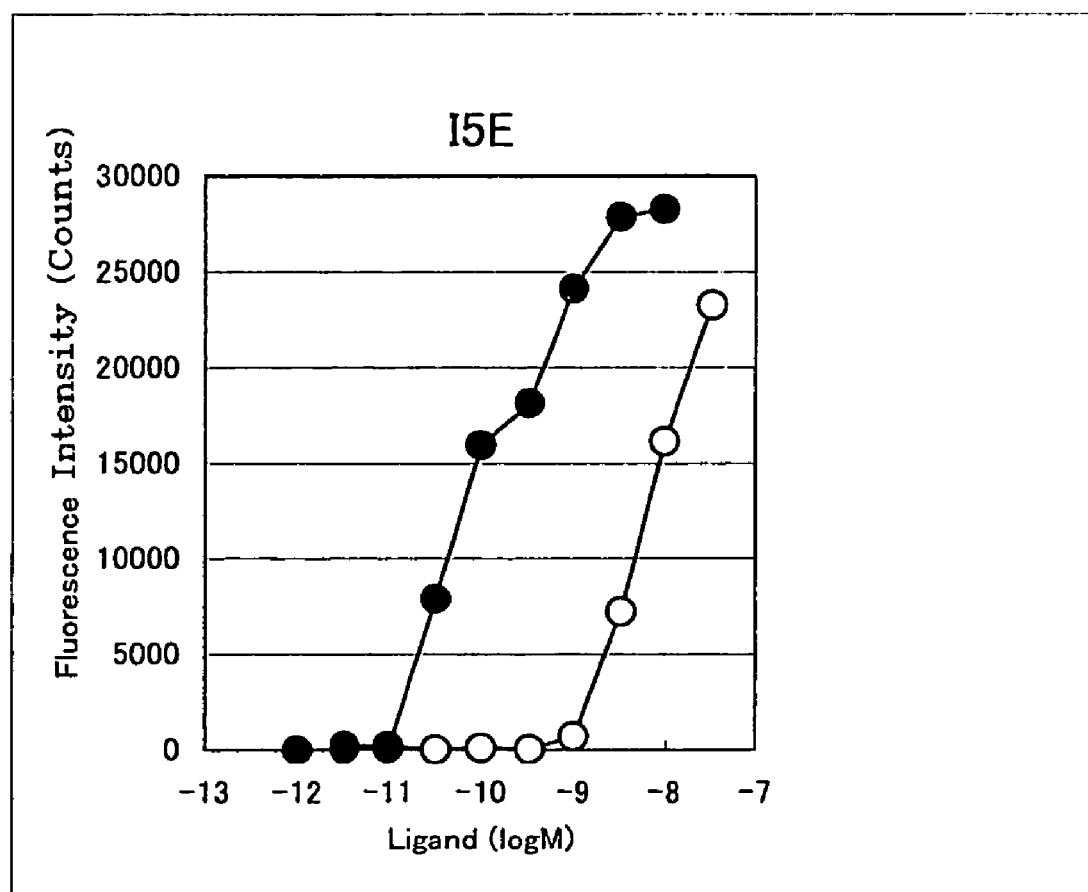
FIG. 13 shows the results of the measurement for I5E receptor activating effects by human type ZAQ ligand peptide and MIT1 assayed in EXAMPLE 8 (8-3), wherein -o- and -•- represent of human type ZAQ ligand peptide and MIT1, respectively.

The human type ZAQ ligand peptide purified by the procedure described in EXAMPLE 7 and the snake venom MIT1 purified by the procedure described in (8-1) above were assayed for the ZAQ receptor activating function and the I5E receptor activating function by the testing method described in (3-5). The results are shown in FIG. 12 and FIG. 13.

As a result, the human type ZAQ ligand peptide and snake venom MIT1 induced an increase of the intracellular calcium ion concentration concentration-dependently. The ZAQ receptor activating function of snake venom MIT1 was more potent by 10 times than that of human type ZAQ ligand peptide. Also, the human type I5E receptor activating function of snake venom MIT1 was more potent by about 100 times than that of human type ZAQ ligand peptide.

Example 9

Cloning of cDNA Encoding rat Brain-derived Novel G Protein-coupled Receptor Protein (rZAQ1) and Determination of the Base Sequence Using whole rat brain cDNA library (CLONTECH Laboratories, Inc.) as a template and two primers (SEQ ID NO: 37 and SEQ ID NO: 38), PCR was carried out. The reaction solution in the above reaction was composed of the above cDNA used as a 1/10 volume template, 1/50 volume of Advantage 2 cDNA Polymerase Mix (CLONTECH Laboratories, Inc.), 0.2 µM each of the respective primers, 200 µM dNTPs and a buffer supplied with the enzyme to make the final volume 25 µl. In the PCR, (1) after reacting at 94° C. for 2 minute, (2) a cycle set at 94° C. for 20 seconds followed by 72° C. for 1 minute and 30 seconds was repeated 3 times, (3) a cycle set at 94° C. for 20 seconds and at 68° C. for 1 minute and 30 seconds was repeated 3 times, (4) a cycle set at 94° C. for 20 seconds, at 62° C. for 20 seconds and at 68° C. for 1 minute was repeated 36 times, and finally, an extension reaction was carried out at 68° C.

for 7 minutes. After completion of the PCR, the reaction product was subcloned to plasmid vector pCR2.1-TOPO (Invitrogen, Inc.) according to the instructions attached to the TA cloning kit (Invitrogen, Inc.), which was then introduced into *Escherichia coli* DH5α, and the clones bearing the cDNA were selected in LB agar medium containing ampicillin. The sequence of each clone was analyzed to give cDNA encoding novel G protein-coupled receptor protein (SEQ ID NO: 39). In the amino acid sequence deduced from the base sequence of this cDNA, homology of 83.7% to the amino acid sequence represented by SEQ ID NO: 1 was observed. Novel G protein-coupled receptor protein containing this amino acid sequence was named r ZAQ1. Transformant (*E. coli*) bearing the DNA containing the base sequence represented by SEQ ID NO: 39 was named *Escherichia coli* DH5α/pCR2.1-rZAQ1.

Example 10

Cloning of cDNA Encoding Rat Brain-derived Novel G Protein-coupled Receptor Protein (rZAQ2) and Determination of the Base Sequence The clone encoding rZAQ2 was acquired by the gene trapper method. That is, probes (SEQ ID NO: 41 and SEQ ID NO: 42) were biotinated, and hybridized to single-stranded whole rat brain cDNA library (GIBCO-BRL). The single stranded gene obtained was repaired to double strand. This gene was electroporated to *Escherichia coli* DH10B, and transformants were obtained using ampicillin resistance as an indicator. According to the colony PCR using a probe (SEQ ID NO: 41) and a primer (SEQ ID NO: 45), a clone encoding the target base sequence was selected. The amino acid sequence (SEQ ID NO: 47) deduced from the base sequence (SEQ ID NO: 46) of ORF (open reading frame) predicted from the base sequence of this clone had homology of 80.6% to rZAQ1. Novel G protein-coupled receptor protein containing this amino acid sequence was named rZAQ2. Transformant (*E. coli*) acquired by the gene trapper method was named *Escherichia coli* DH10B/pCMV-rZAQ2.

Example 11

Contraction Test Using a Sample Preparation of the Ileum Extracted from Guinea Pig Guinea pig (std: Hartley, 7–8 weeks old, male weighing about 450 g) was bled to death by cutting the carotid artery with scissors and the abdomen was opened to remove the ileum. The ileum was placed in a glass petri dish charged with Tyrode's solution (composition: 138 mM NaCl, 2.7 mM KCl, 1.8 mM $CaCl_2$, 0.5 MM $MgCl_2$, 1.1 mM $NaH_2PO_4$, 11.9 mM $NaHCO_3$, 5.6 mM glucose), and fat debris and connective tissues adhered to the ileum were trimmed away with surgical scissors and forceps. The ileum was then cut into pieces of about 1.5 cm long and provided as a sample preparation. This preparation was suspended in an organ bath (20 ml) filled with the Tyrode's solution warmed to 37° C., and a load of 0.5 g was applied to stabilize over 30 minutes or more.

A contraction response of the ileum preparation was measured using AMPLIFIER CASE 7747 manufactured by NEC San-Ei Co., Ltd.

After 1 μM acetylcholine was given to determine the maximum contraction response, the human type ZAQ ligand peptide (ZAQL-1) obtained in accordance with the procedure of REFERENCE EXAMPLE 1 or snake venom MIT1 obtained in (8-1-3) above was administered cumulatively to assay the contraction response. For dilution of ZAQL-1 and MIT1, physiological saline containing 0.05% bovine serum albumin was used.

Figure 14:
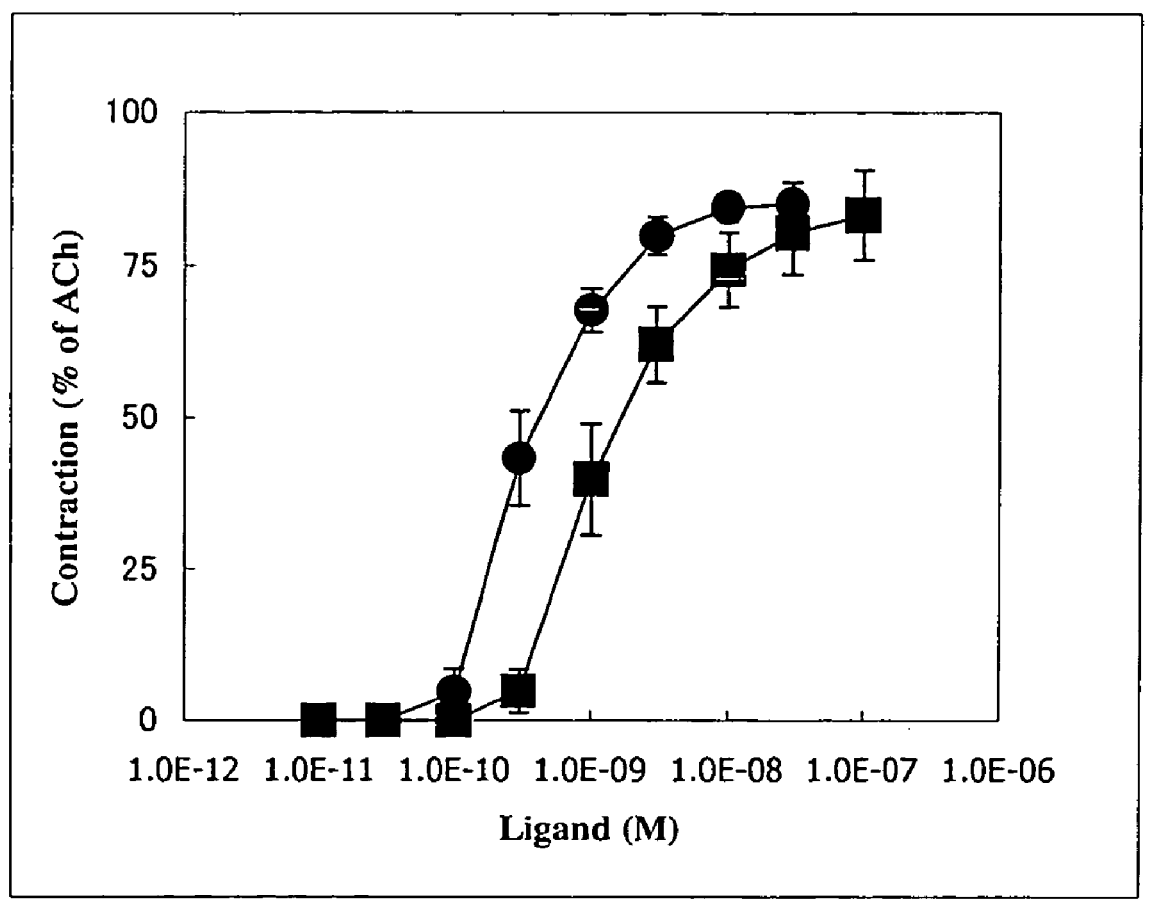
FIG. 14 shows the results of the measurement for contractile activity assayed in EXAMPLE 11, wherein -■- and -•- represent human type ZAQ ligand peptide and MIT1, respectively.

The results are shown in FIG. 14. The contraction response induced by ZAQL-1 and MIT1 is expressed by percentage when the contraction response induced by 1 μM acetylcholine is made 100%.

As a result, ZAQL-1 and MIT1 induced a potent contraction response dose-dependently. The $EC_{50}$ values of ZAQL-1 and MIT1 calculated from the dose-response curve were 1.79 nM and 0.40 nM, respectively.

Example 12

Binding Assay Using the ZAQ- and I5E-expressed CHO Cell Membrane Fractions (12–1) Preparation of $^{125}$I-MIT1

Benzene containing in [$^{125}$I]-Bolton-Hunter Reagent (monoiodinated, 37 MBq, NEN Co., NEX 120) was removed by nitrogen gas, 20 μl of DMSO was added thereto, and the evaporated matters were dissolved by pipetting. To the solution, 80 μl of the solution containing 4 nmol of MIT1 diluted with Borate buffer (composition: 100 mM $H_3BO_3$, pH 8.5) was added and immediately thereafter they were mixed, followed by incubation at room temperature for 2 hours. Then, 200 μl of 10% acetonitrile-0.1% trifluoroacetic acid was added and the mixture was provided as a sample for HPLC fractionation. The sample was loaded onto a column (Toso, Co., Ltd., 0.46 cm×10 cm) for TSKgel Super-ODS reversed phase high performance liquid chromatography, which had been equilibrated by passing 100 vol % eluent A (10% acetonitrile/0.1% trifluoroacetic acid)/0 vol % of eluent B (0.1% trifluoroacetic acid/40% acetonitrile) at room temperature at a flow rate of 1 ml/min. Thereafter, the concentration of eluent B was increased to 60 vol % of eluent A/40 vol % of eluent B over 1 minute and then increased with a linear gradient 40 vol % of eluent A/60 vol % of eluent B over 60 minutes, at a flow rate of 1 ml/min. The [$^{125}$I]-Bolton-Hunter Reagent-introduced MIT1 eluted was manually fractionated and diluted with a buffer (composition: 20 mM Tris, 1 mM EDTA, 0.2% BSA, 0.1% CHAPS, 0.03% NaN3, pH 7.4). The dilution was dispensed and stored at −80° C.

(12–2) Preparation of Cell Membrane Fractions

Cell membrane fractions were prepared in accordance with the method described in Journal of Pharmacology and Experimental Therapeutics, 279, 675–685, 1996. In Dulbecco's Modified Eagle Medium (DMEM) (Nissui Pharmaceutical Co., Ltd.) supplemented with 10% dialyzed fetal bovine serum (JRH BIOSCIENCES), 1 mM of MEM non-essential amino acid solution, 100 units/ml of penicillin and 100 μg/ml of streptomycin, the receptor-expressed CHO cells, namely, ZAQC-B1 cells or I5E4 cells were cultivated in Single Tray (Nunc). When the cells reached a cell density of 80–90%, the culture supernatant was discarded, and 30 ml of PBS (TaKaRa Shuzo Co., Ltd.) containing 1 g/l EDTA was added to the tray to wash the cells. Then, the culture supernatant was discarded, and 30 ml of the PBS-EDTA described above was added thereto, which was allowed to stand at room temperature. The tray was shaken to detach the cells, and the cell suspension was recovered. Again, 10 ml of the PBS-EDTA described above was added to the tray for washing and the cells remained on the tray were detached and mixed with the cells in the cell suspension recovered before. The mixed cell suspension was centrifuged at 1,000 rpm for 5 minutes using a high speed centrifuge (TOMY RL601). The culture supernatant was discarded, and the precipitated cells were stored at −80° C. After 4 ml of a homogenate buffer (composition: 10 mM NaHCO$_3$, 5 mM EDTA, 0.5 mM phenylmethylsulfonyl fluoride (PMSF), 5 μg/ml pepstatin-A, 20 μg/ml leupeptin, 10 μg/ml E-64) was added to the precipitates (corresponding to one Single Tray), the precipitates were suspended by pipetting and the suspension was homogenized under conditions at scale 4 for 20 seconds, using Polytron (blade type PTA7), which was repeated 3 times. Next, the homogenate was centrifuged at 2,500 rpm for 10 minutes using No. 26 Rotor of Hitachi high speed cooling centrifuge CR26H. The supernatant obtained was further centrifuged at 35,000 rpm for an hour using SRP70AT Rotor of ultracentrifuge (Hitachi Koki, SCP70H). To the precipitates obtained was added 5 ml of a binding assay buffer (composition: 20 mM Tris, 1 mM EDTA, 0.5 mM PMSF, 10 μg/ml pepstatin-A, 40 μpg/ml leupeptin, 10 μg/ml E-64, 0.03% NaN$_3$, pH 7.4) to suspend them. The suspension was filtrated through Cell Strainer (FALCON 2350) to give ZAQC-B1 cell membrane fraction (i.e., the ZAQ membrane fraction) or I5E-4 cell membrane fraction (i.e., the I5E membrane fraction). Each of the membrane fractions was assayed for its protein level using Coomassie Protein Assay Reagent (PIERCE), and 100 μl each was dispensed and stored at −80° C.

(12–3) Binding Assay

The ZAQ membrane fraction and the I5E membrane fraction were diluted with 0.1% BSA-containing binding assay buffer described in (12-2) above to 10 μg/ml and 20 μg/l, respectively, and 200 μl each was dispensed in tubes (FALCON 2053). To each dilution of the membrane fractions, 2 μl of a test compound and 2 μl of 10 nM $^{125}$I-MIT1 were added, respectively, followed by incubation at 25° C. for an hour. As the test compound, human type ZAQ ligand peptide (ZAQL-1) acquired in accordance with the procedure of REFERENCE EXAMPLE 1 or snake venom MIT1 (non-labeled MIT1) obtained in (8-1-3) above was used.

Next, 1.5 ml of a filtrating buffer (composition: 20 mM Tris, EDTA, 0.1% BSA, 0.05% CHAPS, 0.03% NaN$_3$, pH 7.4) was added to the reaction solution. The mixture was immediately filtrated through a glass fiber filter paper GF/F (Whatman), which had previously treated with a buffer (composition: 20 mM Tris, 0.3% polyethyleneimine, pH 7.4), 1.5 ml of the filtrating buffer was again added to the reaction tubes, and the mixture was similarly filtered. The radioactivity on the glass fiber filter paper was measured using a γ counter (COBRA, Packard) to determine the binding amount of $^{125}$I-MIT1. The $^{125}$I-MIT1 binding amount when non-labeled MIT1 (final concentration of 1 μM) was used as a test compound was made a non-specific binding amount (NSB), the $^{125}$I-MIT1 binding amount when no test compound was used was made a total binding amount (TB), and the maximum binding amount (TB−NSB) was calculated. Also, with respect to the binding amount (B) obtained when a test compound was added, the binding amount in the presence of a test compound was expressed by percentage of a specific binding amount (B−NSB) calculated to the total specific binding {%SPB=(B−NSB)/(TB−NSB)×100}.

Figure 15:
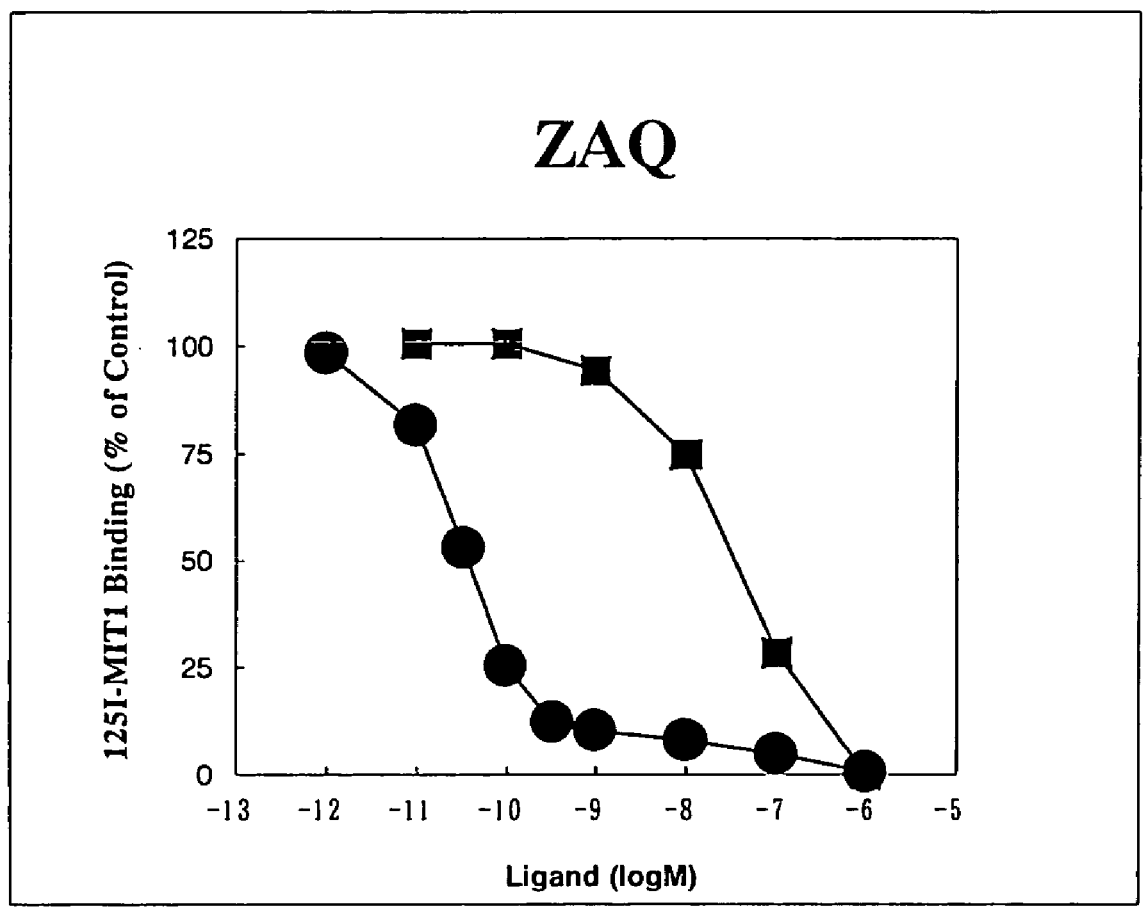
FIG. 15 shows the results of the measurement for binding assay performed in EXAMPLE 12 using the membrane fraction of ZAQ, wherein -■- represents $^{125}$I-MIT1 specific binding amount when human type ZAQ ligand peptide in variable concentrations (as given on the abscissa) was added as a test compound, and -•- represents $^{125}$I-MIT1 specific binding amount when MIT1was similarly added as a test compound.
Figure 16:
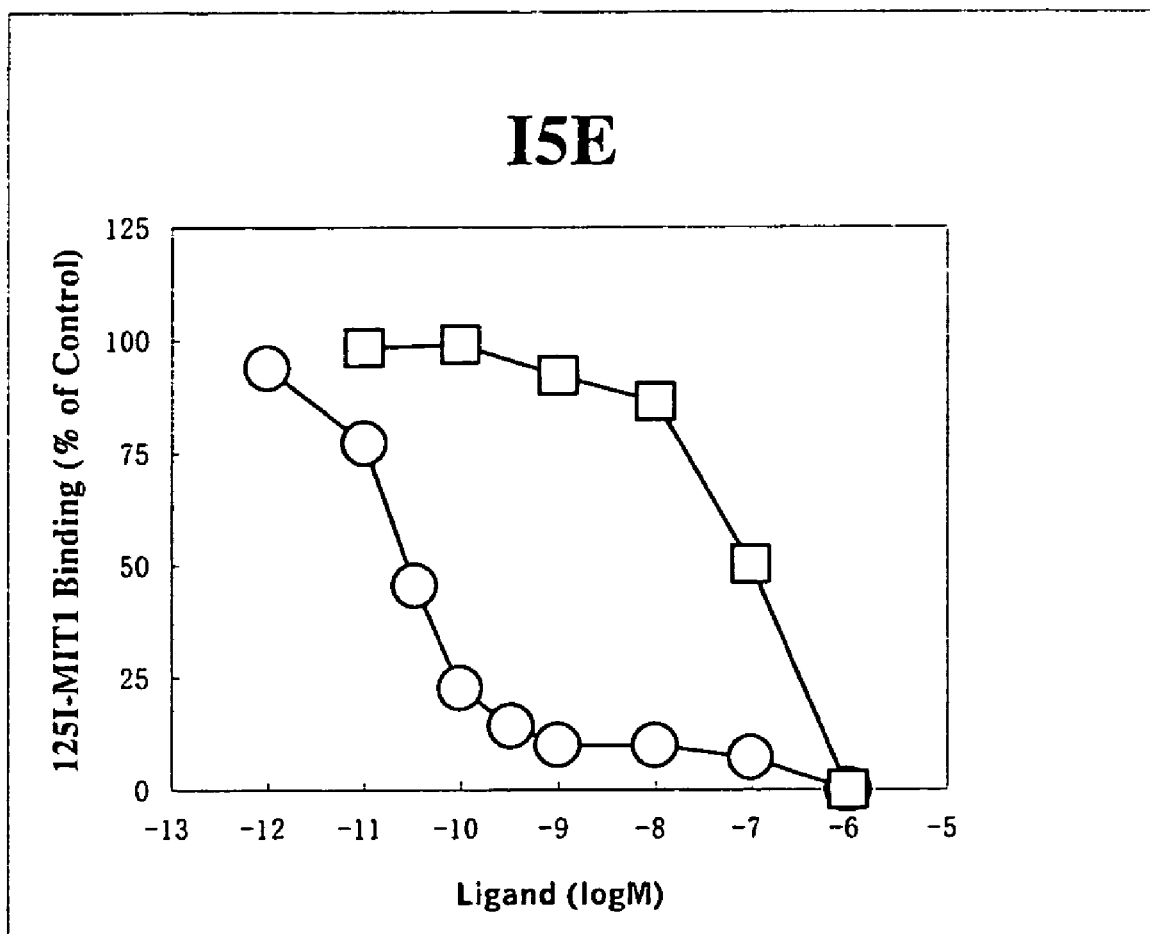
FIG. 16 shows the results of the measurement for binding assay performed in EXAMPLE 12 using the membrane fraction of I5E, wherein -□- represents $^{125}$I-MIT1 specific binding amount when human type ZAQ ligand peptide in variable concentrations (as given on the abscissa) was added as a test compound, and -o- represents $^{125}$-MIT1 specific binding amount when MIT1 in variable concentrations (as given on the abscissa) was added as a test compound.

The results obtained using the ZAQ membrane fraction and the I5E membrane fraction are shown in FIG. 15 and FIG. 16, respectively.

The IC$_{50}$ values of non-labeled MIT1 calculated by this binding assay system were 38 pM (ZAQ membrane fraction) and 32 pM (I5E membrane fraction). The IC$_{50}$ values of ZAQL-1 were 35 pM (ZAQ membrane fraction) and 93 pM (I5E membrane fraction).

Reference Example 1

Production of Human Type ZAQ Ligand (SEQ ID NO: 21) in *Escherichia coli*

(Reference Example 1-1)

Construction of Human Type ZAQ Ligand Expressing Plasmid in *Escherichia Coli*

(a) Using the Following Six DNA Fragments #1 Through #6, the Structural DNA of ZAQ Ligand Was Prepared.

```
#1:
5'-TATGGCGGTGATTACCGGTGCGTGCGAACGTGATGTGCAGTGCGGTGCG      (SEQ ID NO: 52)
GGTACCTGCTGCGCGATTAGCCTGTGGCTGCGTGGTCTG-3'

#2:
5'-CGTATGTGCACCCCGCTGGGTCGTGAAGGTGAAGAATGCCATCCGGGTA      (SEQ ID NO: 53)
GCCATAAAGTGCCGTTCTTCCGTAAACGTAAACATCATACCTG-3'

#3:
5'-CCCGTGCCTGCCGAACCTGCTGTGCAGCCGTTTCCCGGATGGTCGTTAT      (SEQ ID NO: 54
CGTTGCAGCATGGATCTGAAAAACATTAACTTTTAGG-3'

#4:
5'-CACATACGCAGACCACGCAGCCACAGGCTAATCGCGCAGCAGGTACC       (SEQ ID NO: 55)
CGCACCGCACTGCACATCACGTTCGCACGCACCGGTAATCACCGCCA-3'

#5:
5'-AGGCACGGGCAGGTATGATGTTTACGTTTACGGAAGAACGGCACTTTAT     (SEQ ID NO: 56)
GGCTACCCGGATGGCATTCTTCACCTITCACGACCCAGCGGGGTG-3'

#6:
5'-GATCCCTAAAAGTTAATGTTTTTCAGATCCATGCTGCAACGATAACGACC    (SEQ ID NO: 57)
ATCCGGGAAACGGCTGCACAGCAGGTTCGGC-3'
```

(b) Phosphorylation of DNA Oligomer

Each of the four DNA oligomers (#2 through #5) except for #1 and #6, which should form the 5' end, was reacted at 37° C. for an hour in 25 μl of reaction solution for phosphorylation [10 μg of DNA oligomer, 50 mM Tris-HCl, pH.7.6, 10 mM MgC12, 1 mM sperimidine, 10 mM dithiothreitol (hereinafter abbreviated as DTT), 0.1 mg/ml bovine serum albumin (hereinafter abbreviated as BSA), 1 mM ATP, 10 units of T4 polynucleotide kinase (TaKaRa Shuzo Co., Ltd.)] to phosphorylate the 5' end of each oligomer. After phenol treatment followed by addition of 2-fold volume of ethanol, the mixture was cooled to −70° C. and centrifuged to precipitate DNA.

(c) Ligation of DNA Fragment

The DNA fragment obtained in (b) above was combined with #1 and #6 above to make the volume 120 μl. The mixture was kept at 90° C. for 10 minutes and cooled gradually to room temperature for annealing. Using TaKaRa DNA Ligation Kit ver. 2 (TaKaRa Shuzo Co., Ltd.), ligation was carried out. After 30 μl of solution II supplied with the kit was added to 30 μl of the annealing solution to thoroughly mix them, 60 μl of solution I supplied with the kit was added to the mixture and the mixture was reacted at 37° C. for an hour for ligation, followed by phenol treatment. The aqueous phase was recovered and 2 volume of ethanol was added thereto. The mixture was cooled to −70° C. and then centrifuged to precipitate the DNA. The DNA fragment thus obtained was phosphorylated using T4 polynucleotide kinase (TaKaRa Shuzo Co., Ltd.), and then provided for the following step (d).

(d) Construction of ZAQ Ligand Expression Vector

After pTCII (described in Japanese Patent Application Laid-Open No. 2000–178297) was digested with NdeI and BanHI (TaKaRa Shuzo Co., Ltd.) at 37° C. for 2 hours, the DNA fragment of 4.3 kb, which was separated by 1% agarose gel electrophoresis, was extracted using QLAquick Gel Extraction Kit (QIAGEN) and dissolved in 25 μl of TE buffer. The NdeI and BamHI fractions of this pTCII were ligated with the structural gene (SEQ ID NO: 58) of ZAQ ligand prepared above, using TaKaRa DNA Ligation Kit ver. 2 (TaKaRa Shuzo Co., Ltd.) to prepare the expression vector. Using 10 μl of the reaction solution, E. coli JM109 competent cells (TOYOBO) was transformed and inoculated onto LB agar medium containing 10 μg/ml of tetracycline, followed by incubation at 37° C. overnight. Tetracycline-resistant colony formed was selected. The transformant was incubated in LB medium overnight, and plasmid pTCh1ZAQ was prepared using QIAprep8 Miniprep Kit (QIAGEN). The base sequence of this ZAQ ligand DNA was identified using Model 377 DNA sequencer from Applied Biosystems, Inc. Plasmid pTCh1ZAQ was transfected to Escherichia coli MM294 (DE3) to acquire ZAQ ligand expression strain, Escherichia coli MM294 (DE3)/pTCh1ZAQ.

(Reference Example 1-2)

Preparation of ZAQ Ligand

In a 2 liter flask, Escherichia coli MM294 (DE3)/pTCh1ZAQ described above was cultured with shaking in 1 liter of LB medium (1% peptone, 0.5% yeast extract and 0.5% sodium chloride) supplemented with 5.0 mg/L tetracycline at 37° C. for 8 hours. The cultured medium obtained was transferred to a fermentation tank of 50 L volume charged with 19 L of main fermentation medium (1.68% sodium monohydrogenphosphate, 0.3% potassium dihydrogenphosphate, 0.1% ammonium chloride, 0.05% sodium chloride, 0.05% magnesium sulfate, 0.02% anti-foam agent, 0.00025% ferrous sulfate, 0.0005% thiamine hydrochloride, 1.5% glucose, 1.5% Hy-Case Amino), and aerial agitation was initiated at 30° C. When turbidity of the cultured medium reached 500 Klett, isopropyl-β-D-thiogalactopyranoside was added in a final concentration of 12 mg/L, and incubation was continued for further 4 hours. After completion of the culture, the culture medium was centrifuged to obtain about 200 g of wet cells. The cells were stored at −80° C.

This transformant Escherichia coli MM294 (DE3)/pTCh1ZAQ has been on deposit with the Institute for Fermentation, Osaka (IFO) under the Accession Number IFO 16527.

(Reference Example 1-3)

Activation of ZAQ Ligand

By adding 400 ml of a mixture of 200 mM Tris/HCl and 7M guanidine hydrochloride (pH 8.0) to 200 g of the cells obtained in REFERENCE EXAMPLE (1-2), the cells were dissolved therein, and the solution was centrifuged (10000 rpm, 1 hour). To the supernatant, 10 L of a mixture of 0.4 M arginine, 50 mM Tris/HCl, 0.2 mM GSSG and 1 mM GSH (pH 8.0) was added, and the mixture was kept at 4° C. overnight for activation.

(Reference Example 1-4)

Purification of ZAQ Ligand

The regenerating solution after the activation in REFERENCE EXAMPLE (1-3) was adjusted to pH of 6.0 and adsorbed onto an SP-Sepharose column (11.3 cm×15 cm) equilibrated with 50 mM phosphate buffer (pH 6.0). The column was eluted with 600 mM NaCl/50 mM phosphate buffer (pH 6.0), and the fractions containing the ZAQ ligand were pooled. The fraction was passed through CM-5PW (21.5 mm×150 mmL) equilibrated with 50 mM phosphate buffer (pH 6.0) and adsorbed thereto. After washing, elution was conducted with a stepwise gradient (60 minutes) of 0–100% B (B=50 mM phosphate buffer+1M NaCl, pH 6.05) to give the ZAQ ligand fraction (elution time: ca. 40 minutes). This fraction was further passed through C4P-50 (21.5 mm ID×300 mmL, Showa Denko) equilibrated with 0.1% trifluoroacetic acid and adsorbed thereto. After washing, elution was conducted with a stepwise gradient (60 minutes) of 25–50% B (B=80% acetonitrile/0.1% trifluoroacetic acid). The ZAQ ligand fractions (elution time: ca. 40 minutes) were pooled and lyophilized to give 80 mg of the lyophilized ZAQ ligand powders.

(Reference Example 1–5)

Characterization of ZAQ Ligand (a) Analysis Using SDS Polyacrylamide Gel Electrophoresis The ZAQ ligand obtained in REFERENCE EXAMPLE (1-4) was suspended in Sample buffer [Laemmli, Nature, 227, 680 (1979)] supplemented with 100 mM DTT. The suspension was heated at 95° C. for 1 minute followed by electrophoresis on Multigel 15/25 (Daiichi Kagaku Yakuhin). After electrophoresis, the gel was stained with Coomassie brilliant blue, and a single protein band was detected at the same position as that of the COS7 cell-derived recombinant ZAQ ligand preparation obtained in EXAMPLE 5. Based on this, it was revealed that the E. coli-derived recombinant ZAQ ligand preparation obtained in REFERENCE EXAMPLE (1-4) had an extremely high purity and had the same molecular weight as that of the recombinant ZAQ ligand produced from COS7 cells.

(b) Analysis of Amino Acid Composition

The amino acid composition was determined using an amino acid analyzer (Hitachi L-8500A Amino Acid Analyzer). The results reveal that the amino acid composition coincided with the amino acid composition deduced from the base sequence of the DNA of ZAQ ligand (peptide comprising the amino acid sequence represented by SEQ ID NO: 21) (TABLE 2).

TABLE 2

| Amino acid | Number of residue per mol | Number of residue per mol predicted from the base sequence of ZAQ ligand |
|---|---|---|
| Asx | 5.7 | 6 |
| Thr[1)] | 3.3 | 4 |
| Ser[1)] | 3.4 | 4 |
| Glx | 5.0 | 5 |
| Pro | 5.6 | 6 |
| Gly | 7.7 | 8 |
| Ala | 3.9 | 4 |
| Cys[2)] | N.D. | 10 |
| Val | 2.9 | 3 |
| Met | 1.9 | 2 |
| Ile | 2.6 | 3 |
| Leu | 8 | 8 |
| Tyr | 1.0 | 1 |
| Phe | 3.7 | 4 |
| His | 3.8 | 4 |
| Lys | 3.8 | 4 |
| Arg | 8.5 | 9 |
| Trp | 0.9 | 1 |

Acid hydrolysis (mean value in hydrolysis with 6N HCl-1% phenol at 110° C. for 24 and 48 hours)
[1)]value extrapolated at 0 hour
[2)]not detected (c) Analysis of N-terminal Amino Acid Sequence The N-terminal amino acid sequence was determined using a gaseous phase protein sequencer (PE Applied Biosystems, Model 492). As a result, the amino acid sequence was coincident with the N-terminal amino acid sequence of ZAQ ligand deduced from the base sequence of ZAQ ligand DNA obtained (TABLE 3).

TABLE 3

| Residue No. | PTH-amino acid[1)] detected (pmol) | Amino acid predicted from the base sequence of ZAQ ligand |
|---|---|---|
| 1 | Ala (99) | Ala |
| 2 | Val (100) | Val |
| 3 | Ile (91) | Ile |
| 4 | Thr (57) | Thr |
| 5 | Gly (70) | Gly |
| 6 | Ala (89) | Ala |
| 7 | N.D. | Cys |
| 8 | Glu (60) | Glu |
| 9 | Arg (49) | Arg |
| 10 | Asp (54) | Asp |
| 11 | Val (79) | Val |
| 12 | Gln (67) | Gln |
| 13 | N.D. | Cys |
| 14 | Gly (54) | Gly |
| 15 | Ala (65) | Ala |
| 16 | Gly (47) | Gly |
| 17 | Thr (32) | Thr |
| 18 | N.D. | Cys |
| 19 | N.D. | Cys |
| 20 | Ala (36) | Ala |

[1)]Analysis was performed using 150 pmols of phenylthiohydantoin.
N.D. not detected (d) Analysis of C-terminal Amino Acid The C-terminal amino acid sequence was determined using an amino acid (Hitachi L-8500A Amino Acid Analyzer). The ZAQ ligand obtained was coincident with the C-terminal amino acid sequence deduced from the base sequence of DNA (TABLE 4).

TABLE 4

| C-terminal amino acid | Recovery rate (%) |
|---|---|
| Phe | 49.8 |

Gas Phase Hydrazinolysis Method (100° C., 3.5 Hours)

(e) Mass Spectrometry

Mass spectrometry was carried out using LCQ ion trap mass spectrometer (manufactured by ThermoQuest, Inc.) equipped with nano ESI ion sources. As a result, the molecular weight of 9657.55±0.89 was found and coincident well with the calculated molecular weight (9657.3) of ZAQ ligand represented by SEQ ID NO: 21, in which 10 Cys residues contained in SEQ ID NO: 21 formed 5 pairs of disulfide bonds.

(Reference Example 1–6)

Assay for ZAQ Ligand (Assay for the Intracellular Ca Ion Concentration Increasing Activity Using FLIPR)

The purified recombinant ZAQ ligand preparation derived from *Escherichia coli*, which was prepared in REFERENCE EXAMPLE (1-4), was assayed for the activity (assay for the intracellular Ca ion concentration increasing activity using FLIPR) by the method in EXAMPLE 5. As a result, this had an activity equivalent to that of the COS7-derived recombinant preparation (purified ZAQ ligand) obtained in EXAMPLE 5.

INDUSTRIAL APPLICABILITY

The peptide of the invention, the DNA encoding the peptide of the invention (hereinafter sometimes merely referred to as the DNA of the invention) and the antibody to the peptide of the invention (hereinafter sometimes merely referred to as the antibody of the invention) are useful for implementing (1) agents for the prevention/treatment of various diseases associated with the peptide of the invention; (2) screening of a compound or its salt that alters the binding property between the peptide of the invention and the protein of the invention; (3) quantification of the peptide of the invention or its salt; (4) an agent for gene diagnosis; (5) drugs comprising the antisense DNA; (6) drugs comprising the antibody of the invention; (7) preparation of non-human animals bearing the DNA of the invention; (8) drug design based on comparison between ligands and receptors that are structurally analogous, etc.

The invention claimed is:

1. A method of screening a compound or its salt that alters the binding properties between an isolated peptide containing the amino acid sequence of SEQ ID NO: 20 or SEQ ID NO: 21 or salt thereof, and a protein containing the amino acid sequence of SEQ ID NO: 1 or salt thereof, which comprises using an isolated peptide containing the amino acid sequence of SEQ ID NO: 20 or SEQ ID NO: 21 or salt thereof and a protein containing the amino acid sequence of SEQ ID NO: 1, its partial peptide, or a salt thereof in a screening assay.

2. A method of screening a compound or its salt that alters the binding properties between an isolated peptide containing the amino acid sequence of SEQ ID NO: 20 or SEQ ID NO: 21 or salt thereof, and a protein containing the amino acid sequence of SEQ ID NO: 1 or salt thereof, which comprises comparing the binding properties between an isolated peptide containing the amino acid sequence of SEQ ID NO: 20 or SEQ ID NO: 21 or salt thereof and a protein containing the amino acid sequence of SEQ ID NO: 1, its partial peptide, or a salt thereof in a screening assay in the presence of a test compound with the binding properties in the absence of a test compound.

* * * * *